US005977315A

United States Patent [19]
Chatterjee et al.

[11] Patent Number: 5,977,315
[45] Date of Patent: Nov. 2, 1999

[54] MURINE ANTI-IDIOTYPE ANTIBODY 3H1

[75] Inventors: Malaya Chatterjee; Heinz Kohler; Sunil K. Chatterjee; Kenneth A. Foon, all of Lexington, Ky.

[73] Assignee: The Board of Trustees of the University of Kentucky, Lexington, Ky.

[21] Appl. No.: 08/579,940

[22] Filed: Dec. 28, 1995

Related U.S. Application Data

[63] Continuation-in-part of application No. 08/365,484, Dec. 28, 1994, abandoned.

[51] Int. Cl.⁶ .......................... A61K 39/395; C12N 5/12
[52] U.S. Cl. .................... 530/387.2; 530/387.7; 530/388.8; 530/389.7; 424/131.1; 424/138.1; 424/155.1; 424/174.1; 435/344; 435/330; 435/327; 435/7.23
[58] Field of Search .......................... 530/387.2, 387.7, 530/388.8, 389.7; 435/344, 344.1, 440, 327, 330, 7.23, 172.2; 424/131.1, 138.1, 155.1, 174.1

[56] References Cited

U.S. PATENT DOCUMENTS

| | | |
|---|---|---|
| 3,996,345 | 12/1976 | Ullman et al. . |
| 4,436,728 | 3/1984 | Ribi et al. . |
| 4,726,947 | 2/1988 | Shimada et al. . |
| 4,828,991 | 5/1989 | Hanna, Jr. et al. . |
| 5,051,335 | 9/1991 | Yoshida et al. . |
| 5,057,540 | 10/1991 | Kensil et al. . |
| 5,077,284 | 12/1991 | Loria et al. . |
| 5,106,738 | 4/1992 | Hanna, Jr. et al. . |
| 5,160,723 | 11/1992 | Welt et al. . |
| 5,171,568 | 12/1992 | Burke et al. . |
| 5,180,814 | 1/1993 | Hanna, Jr. et al. . |
| 5,183,756 | 2/1993 | Schlom . |
| 5,200,316 | 4/1993 | Elting et al. . |
| 5,227,471 | 7/1993 | Wright, Jr. . |
| 5,244,801 | 9/1993 | Tobi . |
| 5,407,684 | 4/1995 | Loria et al. . |

FOREIGN PATENT DOCUMENTS

| | | |
|---|---|---|
| WO 91/11465 | 8/1991 | WIPO . |
| WO 91/16924 | 11/1991 | WIPO . |
| WO 92/16231 | 10/1992 | WIPO . |

OTHER PUBLICATIONS

Paul Fundamental Immunology Raven Press NY Chapter 8, p. 242, 1993.
Chatterjee et al. (1990) J. Immunol. 145:2758–65, Oct. 15, 1990.
Sambrook et al. (1989) Molecular Cloning, A Laboratory Manual. Cold Spr. Harbor Lab. Press, 1989.
Harlow & Lane (1988) Antibodies, A Laboratory Manual. Cold Spr. Harbor Lab. Press, 1988.
McBride et al., "Induction of tolerance to a murine fibrosarcoma in two zones of dosage—the involvement of suppressor cells" *Br. J. Cancer* (1986) 53:707–711.

Lindenmann, "Speculations on idiotypes and homobodies" *Annales D'Immunologie* (1973) 124C:171–184.
Jerne, "Towards a network theory of the immune system" *Ann. Immunol.* (1974) 125 C:373–389.
Herlyn et al., "Anti–idiotype immunization of cancer patients: Modulation of the immune response" *Proc. Natl. Acad. Sci. USA* (1987) 84:8055–8059.
Mittleman et al., "Human high molecular weight melanoma–associated antigen (HMW–MAA) mimicry by mouse anti–idiotypic monoclonal antibody MK2–23: Induction of humoral anti–HMW–MAA immunity and prolongation of survival in patients with stage IV melanoma" *Proc. Natl. Acad. Sci. USA* (1992) 89:466–470.
Chatterjee et al., "Antiidiotype (Ab2) vaccine therapy for cutaneous T–cell lymphoma" *Ann. N.Y. Acad. Sci.* (1993) 690:376–377.
Hansen et al., "Characterization of second–generation monoclonal antibodies against carcinoembryonic antigen" *Cancer* (1993) 71:3478–3485.
Kuroki et al., "Biochemical characterization of 25 distinct carcinoembryonic antigen (CEA) epitopes recognized by 57 monoclonal antibodies and categorized into seven groups in terms of domain structure of the CEA molecule" *Hybridoma* (1992) 11:391–407.
Goldenberg, "Monoclonal antibodies in cancer detection and therapy" *Am. J. Med.* (1993) 94:297–312.
Hinoda et al., "Internal image–bearing anti–idiotypic monoclonal antibodies" *Tumor Biol.* (1995) 16:48–55.
Losman et al., "Mimicry of a carcinoembryonic antigen epitope by a rat monoclonal anti–idiotype antibody" *Int. J. Cancer* (1994) 56:580–584.
Irvine et al., "Induction of delayed–type hypersensitivity responses by monoclonal anti–idiotypic antibodies to tumor cells expressing carcinoembryonic antigen and tumor–associated glycoprotein–72" *Cancer Immunol. Immuther.* (1993) 36:281–292.
Solin et al., "Immunoglobulin constant kappa gene alleles in twelve strains of mice" *Immunogenetics* (1993) 37:401–407.
Honjo et al., "Cloning and complete nucleotide sequence of mouse immunoglobulin γ1 chain gene" *Cell* (1979) 18:559–568.
Koprowski et al., "Colorectal carcinoma antigens detected by hybridoma antibodies" *Somatic Cell Genet.* (1979) 5:957–972.

(List continued on next page.)

*Primary Examiner*—Julie Reeves
*Attorney, Agent, or Firm*—Morrison & Foerster LLP

[57] ABSTRACT

The present invention provides a monoclonal anti-idiotype antibody 3H1 that escapes immune tolerance and elicits a specific immune response to CEA in mice, rabbits, monkeys, and patients with advanced CEA-associated disease. This invention also provides compositions which can be used in the detection or treatment of CEA-associated tumors mimics a specific epitope on carcinoembryonic antigen and a hybridoma that produces 3H1.

29 Claims, 43 Drawing Sheets

OTHER PUBLICATIONS

Mitchell, "A carcinoembryonic antigen (CEA) specific monoclonal hybridoma antibody that reacts only with high–molecular–weight CEA" *Cancer Immunol. Immunother.* (1980) 10:1–5.

Laemmli, "Cleavage of structural proteins during the assembly of the head of bacteriophage T4" *Nature* (1970) 227:680–685.

Hansen et al., "Solving the problem of antibody interference in commercial 'sandwich'–type immunoassays of carcinoembryonic antigen" *Clin. Chem.* (1989) 35:146–151.

Bhattacharya–Chatterjee et al., "Murine monoclonal anti–idiotype antibody as a potential network antigen for human carcinoembryonic antigen" *J. Immunol.* (1990) 145:2758–2765.

Hawkins et al., "Plasmid vaccination against B–cell lymphoma" *Cancer Gene Therapy.* (1994) 1:208.

Moss, "Vaccinia virus: A tool for research and vaccine development" *Science* (1991) 252:1662–1667.

Bhattacharya–Chatterjee et al., "Idiotypic antibody immunotherapy of cancer" *Cancer Immunol. Immunother.* (1994) 38:75–82.

Bhattacharya–Chatterjee et al., "Idiotype matching: A network antigen idiotype is expressed in sera of colon cancer patients" *Vaccine Res.* (1993) 2:283–290.

Bhattacharya–Chatterjee et al., "Anti–idiotype monoclonal antibodies as vaccines for human cancer" *Intern. Rev. Immunol.* (1991) 7:289–302.

Bhattacharya–Chatterjee et al., "Murine anti–idiotype (Id) monoclonal antibody (mAb) breaks tolerance and induces a specific antibody response to carcinoembryonic antigen (CEA) in colorectal cancer (CRC) patients" *FASEB J.* (1994) 8:A200 (abstract No. 1156).

Foon et al., "Anti–idiotype antibodies: Novel therapeutic approach to cancer therapy" *Tumor Immunology and Cancer Therapy*, Goldfarb, R.H. et al., eds., (1994) Marcel Dekker, Inc. pp. 281–292.

Foon et al., "Immune response to the carcinoembryonic antigen in patients treated with an anti–idiotype antibody vaccine" *J. Clin. Invest.* (1995) 96:334–342.

Kohler et al., "Idiotype manipulation in disease management" *Adv. Exp. Med. Biol.* (1995) 383:117–122.

Chakraborty et al., "Preclinical evaluation in nonhuman primates of an anti–idiotype antibody that mimicks the carcinoembryonic antigen" *J. Immunother.* (1995) 18:95–103.

Bhattacharya–Chatterjee et al., "Syngeneic monoclonal anti– idiotype antibody related to human carcinoembryonic antigen" *Proceedings of the American Association for Cancer Research, 81st Annual Meeting of Cancer Research*, (1990) 31:279 (abstract No. 1651).

Bhattacharya–Chatterjee et al., "Idiotype matching: Level of expression of a network antigen idiotype in colon cancer patients' sera" *FASEB J.* (1991) 5:A1356 (abstract No. 5713).

Bhattacharya–Chatterjee et al., "Active immunotherapy of colorectal patients with murine monoclonal anti–idiotype antibody" *XVI International Cancer Congress* (Oct. 30, to Nov. 5, 1994) pp. 495–499.

Chakaraborty et al., "Murine monoclonal anti–idiotype antibody induces a specific antibody response to human carcinoembryonic antigen (CEA) in cynomolgus monkeys" *FASEB J.* (1994) 8:A504 (abstract No. 2917).

Chatterjee et al., "Anti–idiotypic monoclonal antibodies: Novel approach to immunotherapy" *Handbook of Exp. Pharm.*, Chapter 16 (1994) 113:387–401.

Foon et al., "Murine anti–idiotype (Id) Monoclonal antibody (mAb) induces specific humoral responses to carcinoembryonic antigen (CEA) in correctal cancer (CRC) patients" *Proc. Ann. Mtg. Am. Soc. Clin. Oncol.* (ASCO) (Abstract Submission Form) (1994) 1 page total.

Mukerjee et al., Generation of monoclonal anti–anti–idiotype antibodies (Ab3) that recognize human carcinoembryonic antigen (CEA). *FASEB J.* (1990) 4:A1951 (abstract No. 1497).

Adetugbo, "Evolution of immunoglobulin subclasses" *J. Biol. Chem.* (1978) 253:6068–6075.

Hieter et al., "Cloned human and mouse kappa immunoglobulin constant and J region genes conserve homology in functional segments" *Cell* (1980) 22:197–207.

3H1L.SEQ

TCA TAT GGA TTA CTA GTC GAC
ATG GTA TCC ACA GCT CAG TTC CTT GGT ATC TTG TTG CTC TGG TTT CCA GGT
ATC AAA TCT GAC ATC AAG ATG ACC CAG TCT CCA TCT TCC ATG TAT GGA TCT
CTA GGA GAG AGA GTC ACG ATC ACT TGC AAG GCG AGT CAG GAC ATT AAT GGT
TAT TTA AAT TGG TTC CAA CAA GAA CCA GGG AAA TCT CCT AAG ACC CTG ATC
TAT CGT GCA AAT AGA TTG ATA GAT GGG GTC CCA TCA AGC AGC CTG GGC AGT
GGA TCT GGG CAA GTT TAC TCT CTC ACC ATC AGC AGC CTG GAG TTT GAA GAT
ATG GGA ACT TAT TAT TGT CTA CAG TTT GAT GAG CTT CCG TGG ATG TTC GGT
GGA GGC ACC AAG CTG GAA ATC AAA CGG GCT GAT GCT GCA CCA ACT GTC TCC
ATC TTC CCA CCA TCC AGT

FIG. 1A

3H1L.pep

MVSTAQFLGILLLWFPGIKS

DIKMTQSPSSMYASLGERVTITC

KASQDINGYLN

WFQQEPGKSPKTLIY

RANRLID

GVPSRFSGSGSGQVYSLTISSLEYEDMGTYYC

LQFDEFPWMFGGGTKLEIK

RADAAPTVSIFPPSS

FIG. 1B

3H1H.SEQ

AGTCATATGGATTGGGAATTC

ATG GAA TGG AGC TGG GTC ATT CTC TTC CTC CTG TCA GGA ACT GCA GGT
GTC CAC TCT GAG GTC CAG CTG CAA CAG TCT GGA CCT GAG CTG GTG AAG CCT
GGA GCT TCA CTG AAG ATT TCC TGC GAG GCT TCT GGT TAC TCA CTC ACT GCC
TAC ACC ATG AAC TGG GTG AAG CAG AGC CAT GGA AAG AGC CTT GAG TGG GTT
GGG CTG ATT AAT CCT TTC AGT GGT GAT ACT AAC TAC AGC CAG AAA TTC ACG
GGC AAG GCC ACA TTA ACT GTA GAC AGG TCA TCC AGC ACA GCC TAC ATG GAG
CTC CTC AGT CTG ACA TCT GAG GAC TCT GCA GTC TAT TAC TGT GTC ATT ACT
CCG GTT CCC TAC TGG TAC TTC GAT GTC TGG GGC GCA GGG ACC ACG GTC ACC
GTC TCC TCA GCC AAA ACG ACA CCC CCA TCC GTC TAT

MEWSWVILFLLSGTAGVHS

EVQLQQSGPELVKPGASLKISCEASGYSLT

AYTMN

WVKQSHGKSLEWVG

LINPFSGDTNYSQKFTG

KATLTVDRSSSTAYMELLSLTSEDSAVYYCVI

TPVPYWYFDV

WGAGTTVTVSS

AKTTPPSVY

|  | 190 |  |  |  |  | 195 |  |  |  |  | 200 |  |  |  |  | 205 |  |  |  |  |
|---|---|---|---|---|---|---|---|---|---|---|---|---|---|---|---|---|---|---|---|---|---|
| CAT | AAC | AGC | TAT | ACC | TGT | GAG | GCC | ACT | CAC | AAG | ACA | TCA | ACT | TCA | CCC | ATT | GTC | AAG | AGC | BALB/c |
| --- | --- | --- | --- | --- | --- | --- | --- | --- | --- | --- | --- | --- | --- | --- | --- | --- | --- | --- | --- | CE |
| --- | --- | --- | --- | --- | --- | --- | --- | --- | --- | --- | --- | --- | --- | --- | --- | --- | --- | --- | --- | CBA |
| --- | --- | --- | --- | --- | --- | --- | --- | --- | --- | --- | --- | --- | --- | --- | --- | --- | --- | --- | --- | RIII |
| --- | --- | --- | --- | --- | --- | --- | --- | --- | --- | --- | --- | --- | --- | --- | --- | --- | --- | --- | --- | DBA/2 |
| --- | --- | --- | --- | --- | --- | --- | --- | --- | --- | --- | --- | --- | --- | --- | --- | --- | --- | --- | --- | C57BL |
| --- | --- | --- | --- | --- | --- | --- | --- | --- | --- | --- | --- | --- | --- | --- | --- | --- | --- | --- | --- | A/J |
| --- | --- | --- | --- | --- | --- | --- | --- | --- | --- | --- | --- | --- | --- | --- | --- | --- | --- | --- | --- | NZB |
| --- | --- | --- | --- | --- | --- | --- | --- | --- | --- | --- | --- | --- | --- | --- | --- | --- | --- | --- | --- | C58 |
| --- | --- | --- | --- | --- | --- | --- | --- | --- | --- | --- | --- | --- | --- | --- | --- | --C | --- | --- | --- | AKR |
| --- | --- | --- | --- | --- | --- | --- | --- | --- | --- | --- | --- | --- | --- | --- | --- | --C | --- | --- | --- | PL |
| --- | --- | --- | --- | --- | --- | --- | --- | --- | --- | --- | --- | --- | --- | --- | --- | --C | --- | --- | --- | SJL |
| --- | --- | --- | --- | --- | --- | --- | --- | --- | --- | --- | --- | --- | --- | --- | --- | --C | --- | --- | --- | M. spretus |
| --- | -CT- | --- | --- | --- | --- | --- | -TT | GT- | --T | --- | --- | T-C | --- | --- | --- | G-C | --- | --- | --- | LOU |
| --- | -CT- | --- | --- | --- | --- | --- | -TT | GT- | --T | --- | --- | T-C | --- | --- | --- | G-C | --- | --- | --- | DA |
|  |  |  |  |  |  |  |  | <-MKC-1B |  |  |  |  |  |  |  | <-MKC-4 |  |  |  |  |
|  |  |  |  |  |  |  |  | <-MKC-1 |  |  |  |  |  |  |  |  |  |  |  |  |

```
      210             214        +10         +20        +30        +40        +50    +56
TTC   AAC AGG AAT GAG TGT   TAGAGACAAA GGTCCTGAGA CGCCACCACC AGCTCCCCAG CTCCATCCTA TCTTCC   BALB/c
---   --- --- --- --- ---   ---------- ---------- ---------- ---------- ---------- ------   CE
---   --- --- --- --- ---   ---------- ---------- ---------- ---------- ---------- ------   CBA
---   --- --- --- --- ---   ---------- ---------- ---------- ---------- ---------- ------   RIII
---   --- --- --- --- ---   ---------- ---------- ---------- ---------- ---------- ------   DBA/2
---   --- --- --- -↑- ---   ---------- ---------- ---------- ---------- ---------- ------   C57BL
---   --- --- --- --- -X-   ---------- ---------- ---------- ---------- ---------- ------   A/J
---   --- --- --- --- ---   ---------- ---------- ---------- ---------- ---------- ------   NZB
---   --- --- --- --- ---   ---------- ---------- ---------- ---------- ---------- ------   C58
---   --- --- --- --- ---   ---------- ---------- ---------- ---------- ---------- ------   AKR
---   --- --- --- --- ---   -C-------- ---------- ---------- ---------- ---------- ------   PL
---   --- --- --- --- ---   -C-------- ---------- ---------- ---------- ---------- ------   SJL
---   --- --- --- --- ---   CC-------- ------G T. ---------- ---------- ---T---A-- ------   M.spretus
---   --- --- --- --- ---   CC-------- ------G T. ---------- ---------- ---T---A-- ------   LOU
---   --- --- --- --- ---   ---------- ---------- ---------- ---------- ------------ ------   DA
```

```
                                                                                                        A
  0   TCGGGGACATGGGAAGGTGCAAAAAGTAGCGGCCTTCTAGAAGGTTTGGACCTGTCCTGTCCTGTCCGACAGTGTAATCACATATACTTTTCTTGTAGC
                                                     N   A   S   Q
           K  T  T  P  P  S  V  Y  Y  P  L  A  P  G  S  A  A  Q  T  V  S  M  V  T  L  G  C  L  V  K  G  Y  F  P
                          T
 100  CAAAACGACACCCCCATCTGTCTATCCACTGGCCCCTGGATCTGCTGCCCAAACTAACTCCATGGTGACCCTGGTGCCTGGTCAAGGGCTATTTCCCT

E  P  V  T  V  T  W  N  S  G  S  L  S  S  S  G  V  H  T  F  P  A  V  L  Q  S  D  L  Y  T  L  S  S  S
 200  GAGCCAGTGACAGTGACCTGGAACTCTGGATCCCTGTCCAGCGGTGTGCACACCTTCCCAGCTGTCCTGCAGTCTGACCTCTACACTCTGAGCAGCTCAG

T                                         A  P
           V  T  V  P  S  S  P  R  P  S  E  T  V  T  C  N  V  A  H  P  A  S  S  T  K  V  D  K  K  I
 300  TGACTGTCCCCTCCAGCCCTCGGCCCTCAGCGAGACCGTCACCTGCAACGTTGCCCACCCGGCCAGCAGCACCAAGGTGGACAAGAAAATTGGTGAGAGGAC

400  ATATAGGGAGGAGGGGGTTCACTAGAAGTGAGGCTCAAGCCATTAGCCTGCCTAAACCAACCAGGCTGGACAGCAACCAACCAGGAAATGGATCTCAGCC

500  CAGAAGATCAAAAGTTGTTCTCTCCCTTCTGGAGATTTCTATGTCCTTTACAACTCAATTGGTTAATATCCTGGGTTGGAGTCCCACACATCTTGACAA

600  ACAGAGACAAATTTGAGTATCACCAGCAAAAGTCATACCCAAAAACAGCTGGCATGACCACACCAGACTCAAACTTACCCTACCTTTATCCTGGTG

V  P  R  D  C  G  C  K  P  C  I  C  T
 700  GCTTCTCATCTCCCAGACCCCAGTAACACATAGCTTTCTCTCCACAGTGCCCAGGGATTGTGGTTGTAAGCCTTGCATATGTACAGGTAAGTCAGTGGCCT

V  P  E  V  S  S
 800  TCACCTGACCCAGATGCAACAAGTGGCAATGTTGGAGGGTGGCCAGGTATTGACCTATTTCCACCTTTCTTCTTCATCCTTAGTCCCAGAAGTATCATCT
```

FIG. 4A

```
         V  F  I  F  P  P  K  P  K  D  V  L  T  I  T  L  T  P  K  V  T  C  V  V  V  D  I  S  K  D  D  P  E
     900 GTCTTCATCTTCCCCCCAAAGCCCAAGGATGTGCTCACCATTACTCTGACTCCTAAGGTCACGTGTGTTGTGGTAGACATCAGCAAGGATGATCCCGAGG

V  Q  F  S  W  F  V  D  D  V  E  V  H  T  A  Q  T  Q  P  R  E  E  Q  F  N  S  T  F  R  S  V  S  E  L
    1000 TCCAGTTCAGCTGGTTTGTTGTAGATGATGTGGAGGTGCACACAGCTCAGACGCAACCCCGGGAGGAGCAGTTCAACAGCACTTTCCGCTCAGTCAGTGAACT

P  I  M  H  Q  D  W  L  N  G  K  E  F  K  C  R  V  N  S  A  A  F  P  A  P  I  E  K  T  I  S  K  T
    1100 TCCCATCATGCACCAGGACTGGCTCAATGGCAAGGAGTTCAAATGCAGGGTCAACAGTGCAGCAGCTTTCCCTGCCCCCATCGAGAAAACCATCTCCAAAACC

G  R  P  K  A  P  Q  V  Y  T  I  P  P  P  K  E  Q  M  A  K  D  K  V  S  L
    1200 AAAGGTGAGAGAGCTGCAGTGTGTGACATAGAAGCTGCAATAGTCAGTCCATAGACAGACCCCTGCCCTGTTCGTGACCTCTGTGCT

G  R  P  K  A  P  Q  V  Y  T  I  P  P  P  K  E  Q  M  A  K  D  K  V  S  L
    1300 GACCAATCTCTTTACCCACCCCACAGGCAGACCGAAGGCTCCACAGGTGTACACCATTCCACCTCCCAAGGAGCAGATGGCCAAGGATAAAGTCAGTCTGA

T  C  M  I  T  D  F  F  P  E  D  I  T  V  E  W  Q  W  N  G  Q  P  A  E  N  Y  K  N  T  Q  P  I  M  N
    1400 CCTGCATGATAACAGACTTCTTCCCTGAAGACATTACTGTGGAGTGGCAGTGGAATGGGCAGCCAGCGGAGAACTACAAGAACACTCAGCCCATCATGAA
```

FIG. 4B

```
     D
     T  N  G  S  Y  F  V  Y  S  K  L  N  V  Q  K  S  N  W  E  A  G  N  T  F  T  C  S  V  L  H  E  G  L
1500 CACGGAATGGCTCTTACTTCGTCTACAGCAAGCTCAATGTGCAGAAGAGCAACTGGGAGGCAGGAAATACTTTCACCTGCTCTGTGTTACATGAGGGCCTG

H  N  H  H  T  E  K  S  L  S  H  S  P  G  K term
1600 CACAACCACCATACTGAGAAGAGCCTCTCCCACTCTCCTGGTAAATGATCCCAGTGTCCTTGGAGCCCTCTGGTCCTACAGGACTCTGACACTACCTCC
                                                           .poly A
1700 ACCCCTCCCTGTATAAATAAAGCACCCAGCACTGCCTTGGGACCCTGCAATAACGTCCTGGTGATTTCTGAGATGTAGAGTCTAGCTAGGTCATGGAATG
```

FIG. 4C

MURINE ANTI-IDIOTYPE ANTIBODY 3H1

CROSS-REFERENCE TO RELATED APPLICATIONS

This application is a continuation-in-part of U.S. Ser. No. 08/364,484, filed Dec. 28, 1994, now abandoned which is incorporated by reference herein in its entirety.

STATEMENT OF RIGHTS TO INVENTIONS MADE UNDER FEDERALLY SPONSORED RESEARCH

This invention was made in part during work supported by a grant from the United States Public Health Service (CA 47860) and the National Institutes of Health (CA 57165). The government has certain rights in the invention.

FIELD OF THE INVENTION

This invention relates to anti-idiotype antibodies. More specifically, it relates to monoclonal anti-idiotype antibody 3H1 which elicits an immune response against a specific epitope of carcinoembryonic antigen (CEA).

BACKGROUND OF THE INVENTION

In spite of extensive medical research and numerous advances, cancer remains the second leading cause of death in the United States. Colorectal cancer is the third most common cancer and the second leading cause of cancer deaths. While the traditional modes of therapy, such as surgery, radiotherapy and chemotherapy, are widely used and are in many instances successful, the still existing high death rate from cancers such as colorectal compels the need for alternative modes of therapy.

The immunotherapy of human cancer using tumor cells or tumor-derived vaccines has been disappointing for several reasons. It has been consistently difficult to obtain large quantities of purified tumor-associated antigens which are often chemically ill-defined and difficult to purify. In addition, there remains the problem of the immunobiological response potential against tumor antigens, or in other words, the question of whether a cancer patient can mount effectively an immune response against his or her tumor. Tumor-associated antigens (TAA) are often a part of "self" and usually evoke a very poor immune response in a tumor-bearing host due to tolerance to the antigens, such as T cell-mediated suppression. Immunobiologists have learned that a poor antigen (in terms of eliciting an immune response) can be turned into a strong antigen by changing the molecular environment. Changes of hapten carrier allow T cell helper cells to become active, making the overall immune response stronger. Thus, changing the carrier can also turn a tolerogenic antigen into an effective antigen. McBridge et al. (1986) Br. J. Cancer 53:707. Often the immunological status of a cancer patient is suppressed such that the patient is only able to respond to certain T-dependent antigens and not to other antigen forms. From these considerations, it would make sense to introduce molecular changes into the tumor-associated antigens before using them as vaccines. Unfortunately, this is impossible to accomplish for most tumor antigens, because they are not well defined and are very hard to purify.

The network hypothesis of Lindemann ((1973) Ann. Immunol. 124:171–184) and Jerne ((1974) Ann. Immunol. 125:373–389) offers an elegant approach to transform epitope structures into idiotypic determinants expressed on the surface of antibodies. According to the network concept, immunization with a given tumor-associated antigen will generate production of antibodies against this tumor-associated antigen, termed Ab1; this Ab1 is then used to generate a series of anti-idiotype antibodies against the Ab1, termed Ab2. Some of these Ab2 molecules can effectively mimic the three-dimensional structure of the tumor-associated antigen identified by the Ab1. These particular anti-idiotypes called Ab2β fit into the paratopes of Ab 1, and express the internal image of the tumor-associated antigen. The Ab2β can induce specific immune responses similar to those induced by the original tumor-associated antigen and can, therefore, be used as surrogate tumor-associated antigens. Immunization with Ab2β can lead to the generation of anti-anti-idiotype antibodies (Ab3) that recognize the corresponding original tumor-associated antigen identified by Ab1. Because of this Ab1-like reactivity, the Ab3 is also called Ab1' to indicate that it might differ in its other idiotopes from Ab1. Anti-Id monoclonal antibodies structurally resembling tumor-associated antigens have been used as antigen substitute to induce anti-tumor immunity in cancer patients. Herlyn et al. (1987) Proc. Natl. Acad. Sci., USA 84:8055–8059; Mittleman et al. (1992 Proc. Natl. Acad. Sci., USA 89:466–470; Chatterjee et al. (1993) Ann. N.Y. Acad. Sci. 690:376–278.

A potentially promising approach to cancer treatment is immunotherapy employing anti-idiotype antibodies. In this form of therapy, an antibody mimicking an epitope of a tumor-associated protein is administered in an effort to stimulate the patient's immune system against the tumor, via the tumor-associated protein. WO 91/11465 describes methods of stimulating an immune response in a human against malignant cells or an infectious agent using primate anti-idiotype antibodies. However, not all anti-idiotype antibodies can be used in therapeutic regimens against tumors. Moreover, since different cancers have widely varying molecular and clinical characteristics, it has been suggested that anti-idiotype therapy should be evaluated on a case by case basis, in terms of tumor origin and antigens they express.

Anti-Id monoclonal antibodies structurally resembling tumor-associated antigens have been used as antigen substitutes in cancer patients. Herlyn et al. (1987); Mittleman et al. (1992); Chatterjee et al. (1993). It has been proposed that the anti-Id provides a partial analog of the tumor-associated antigen in an immunogenic context.

Carcinoembryonic antigen (CEA) is a 180,000-kiloDalton glycoprotein tumor-associated antigen present on endodermally-derived neoplasms of the gastrointestinal tract, such as colorectal and pancreatic cancer, as well as other adenocarcinomas such as breast and lung cancers. CEA is also found in the digestive organs of the human fetus. Circulating CEA can be detected in the great majority of patients with CEA-positive tumors. Specific monoclonal antibodies have been raised against CEA and some have been radiolabeled for diagnostic and clinical studies. Hansen et al. (1993) Cancer 71:3478–3485; Karoki et al. (1992) Hybridoma 11:391–407; Goldenberg (1993) Am. J. Med. 94:297–312. As with most tumor-associated antigens which are seen as self-antigens by the immune system, cancer patients are immunologically "tolerant" to CEA, possibly due to its oncofetal origin. Studies to date on patients with CEA-positive tumors have not demonstrated the ability to generate immunity to CEA. Thus, immunotherapy based on CEA has heretofore not been possible.

CEA nonetheless is an excellent tumor-associated antigen for active immunotherapy with anti-idiotype antibody. CEA is typically present at high levels on the tumor cell surface.

CEA is also one of the most well-characterized antigens, as its gene sequence is known and its three dimensional structures have been identified. CEA is a member of the immunoglobulin supergene family located on chromosome 19 which is thought to be involved in cell-cell interactions.

In as much as some of the epitopes on CEA are shared by normal tissues, immunization with intact CEA molecule might trigger potentially harmful autoimmune reactions. An immune reaction against a tumor-associated epitope, on the other hand, would be desirable. An appropriate anti-idiotype antibody would be an excellent candidate to induce anti-tumor immunity in CEA positive cancer patients. A number of investigators have generated anti-idiotype antibodies in rats, mice, baboons and humans that mimic CEA. See, e.g., Hinoda et al. (1995) Tumor Biol. 16:48–55; Losman et al. (1994) Int. J. Cancer 56:580–584; Irvine et al. (1993) Cancer Immunol. Immunother. 36:281–292. However, given the size of CEA (and likely numerous epitopes), and the fact that CEA is expressed on some normal tissues, it was not known whether anti-idiotype antibodies would be effective in eliciting an anti-CEA response that effects anti-tumor immunity.

Carcinomas of the gastrointestinal tract are often not curable by standard therapies. Thus, new therapeutic approaches for this disease are needed. The present invention overcomes the deficiencies in the prior art by providing a monoclonal anti-idiotype antibody (3H1) as an antigen (Ag) substitute to induce anti-tumor immunity in gastrointestinal cancer patients with advanced CEA-associated disease, such as colorectal cancer.

All publications cited herein are hereby incorporated by reference in their entirety.

SUMMARY OF THE INVENTION

The present invention provides a murine monoclonal anti-idiotype antibody, 3H1, which is able to elicit an immune response against carcinoembryonic antigen (CEA). The invention also provides the amino acid sequence of the variable regions of 3H1 and a polynucleotide sequence encoding these variable regions of 3H1.

Accordingly, in one aspect, the invention includes a monoclonal anti-idiotype antibody 3H1 produced by a hybridoma cell line ATCC No. HB12003 and progeny thereof.

In another aspect, the invention includes a hybridoma cell line designated ATCC No. HB12003 and progeny thereof.

In another aspect, the invention includes a hybridoma cell line that produces a monoclonal anti-idiotype antibody having a light chain variable region amino acid sequence identical to SEQ ID NO:2 and a heavy chain variable region amino acid sequence identical to SEQ ID NO:4.

In another aspect, the invention includes a monoclonal anti-idiotype antibody having a light chain variable region amino acid sequence identical to SEQ ID NO:2 and a heavy chain variable region amino acid sequence identical to SEQ ID NO:4.

Another aspect of the invention is an antibody having a light chain variable region encoded by a polynucleotide encoding an amino acid sequence identical to SEQ ID NO:2 and a heavy chain variable region encoded by a polynucleotide encoding an amino acid sequence identical to SEQ ID NO:4.

In another aspect, the invention includes pharmaceutical compositions and vaccines comprising an effective amount of monoclonal anti-idiotype antibody 3H1.

In another aspect, the invention also includes methods of eliciting an immune response in an individual with advanced CEA-associated disease. These methods entail administering to the individual an effective amount of 3H1.

In another aspect, the invention provides methods of detecting the presence of an anti-CEA antibody bound to a tumor cell comprising the steps of contacting the tumor cell with 3H1 for a sufficient time to allow binding to the anti-CEA antibody, and detecting the presence of any 3H1 which is bound to the anti-CEA antibody.

In another aspect, the invention provides a diagnostic kit for detection or quantitation of anti-CEA antibody. These kits contain 3H1 in suitable packaging.

Another aspect of the invention are methods of palliating CEA-associated disease in an individual having advanced CEA-associated disease. These methods entail administration of an effective amount of 3H1 to the individual.

BRIEF DESCRIPTION OF THE DRAWINGS

FIGS. 1A and B depict the DNA sequence (SEQ ID NO:1; FIG. 1A) and the amino acid sequence (SEQ ID NO:2; FIG. 1B) of the light chain variable region of 3H1.

FIGS. 2A and B depict the DNA sequence (SEQ ID NO:3; FIG. 2A) and the amino acid sequence (SEQ ID NO:4; FIG. 2B) of the heavy chain variable region of 3H1.

Figure 3B:
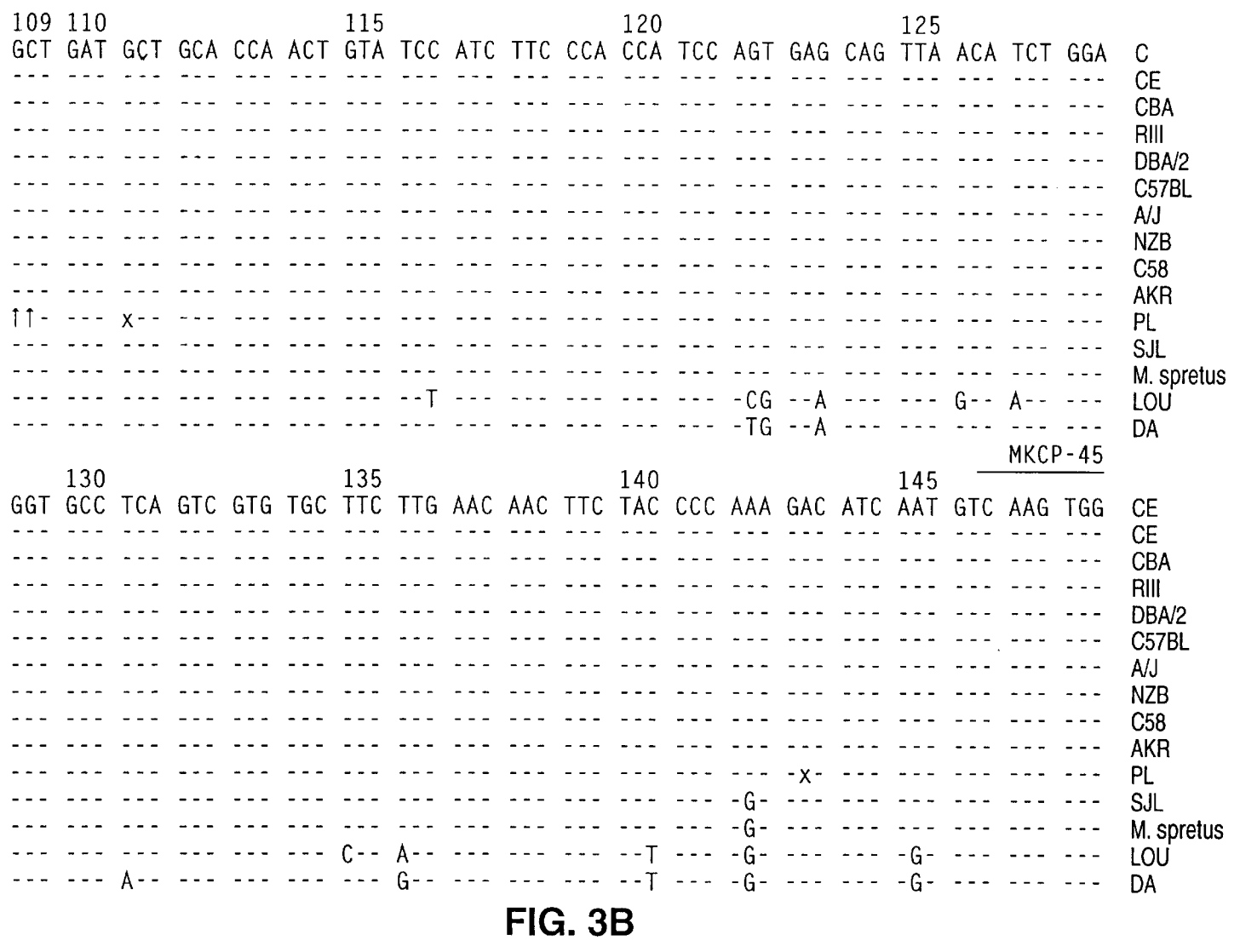
Figure 3C:
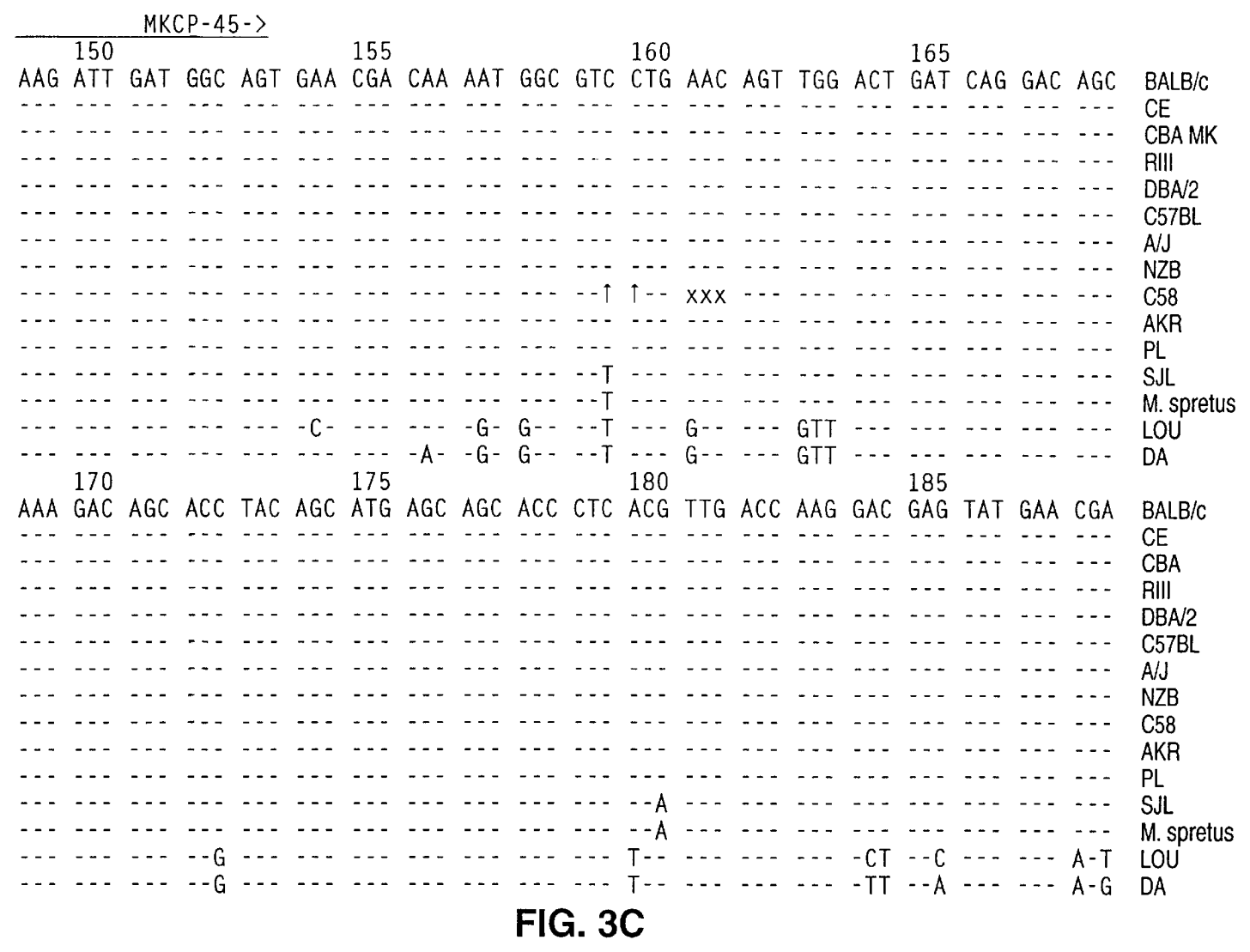

FIGS. 3A–3E depict mouse and rat immunoglobulin kappa chain gene sequences, comparing the sequences within the kappa chain constant region for different strains and highlighting allotypic differences. Included are kappa chain constant region sequences for BALB/c (SEQ. ID NO:5), PL, SJL, and M. spretus. The four genetic allotypes encode two protein allotypes. Other naturally occurring allotypes are possible. The figure is excerpted from Solin et al. (1993) Immunogenetics 37:401–407, which is hereby incorporated herein by reference.

FIGS. 4A–4C depict two allotypes of the mouse immunoglobulin heavy chain. The germ-line DNA sequence from newborn mice is shown (SEQ ID NO:6), along with the encoded protein (SEQ ID NO: 7). Shown in the line above is another protein sequence obtained from the mouse myeloma MOPC 21 (SEQ ID NO: 8). Other naturally occurring allotypes are possible. The figure is excerpted from Honjo et al. (1979) Cell 18:559–568, which is hereby incorporated herein by reference.

In FIG. 19A, tumor cells were reacted with preimmune sera and Ab3 sera (1:100 dilution) from monkeys immunized with 3H1. In FIG. 19B, MOLT-4 cells that do not express CEA were reacted with pre-immune and immune monkey Ab3 sera raised against 3H1.

FIGS. 20A through 20D are half-tone reproductions depicting immunoperoxidase staining of colonic adenocarcinoma and normal colon by monkey Ab3. Serial sections of tumor cells were stained with: FIG. 20A, monkey Ab3 (50 µg/ml); FIG. 20B, 8019 IgG$_1$ (50 µg/ml); FIG. 20C, unrelated monkey Ab3 (50 µg/ml). FIG. 20D shows staining of normal colon cells with monkey Ab3 (50 µg/ml).

FIG. 29B, number 12). For each figure, each pair of bars indicates the extent of T-cell proliferation in the presence of: 3H1-Alugel (first pair); iso-allotype matched control 4DC6-Alugel (second pair); purified CEA (third pair); purified bovine serum albumin (BSA) (fourth pair); and phytohemagglutinin (fifth pair). For each pair, the dark (first) bar denotes pre-immune sera; the hatched (second) bar denotes post-immune sera.

MODES FOR CARRYING OUT THE INVENTION

Figure 3A:
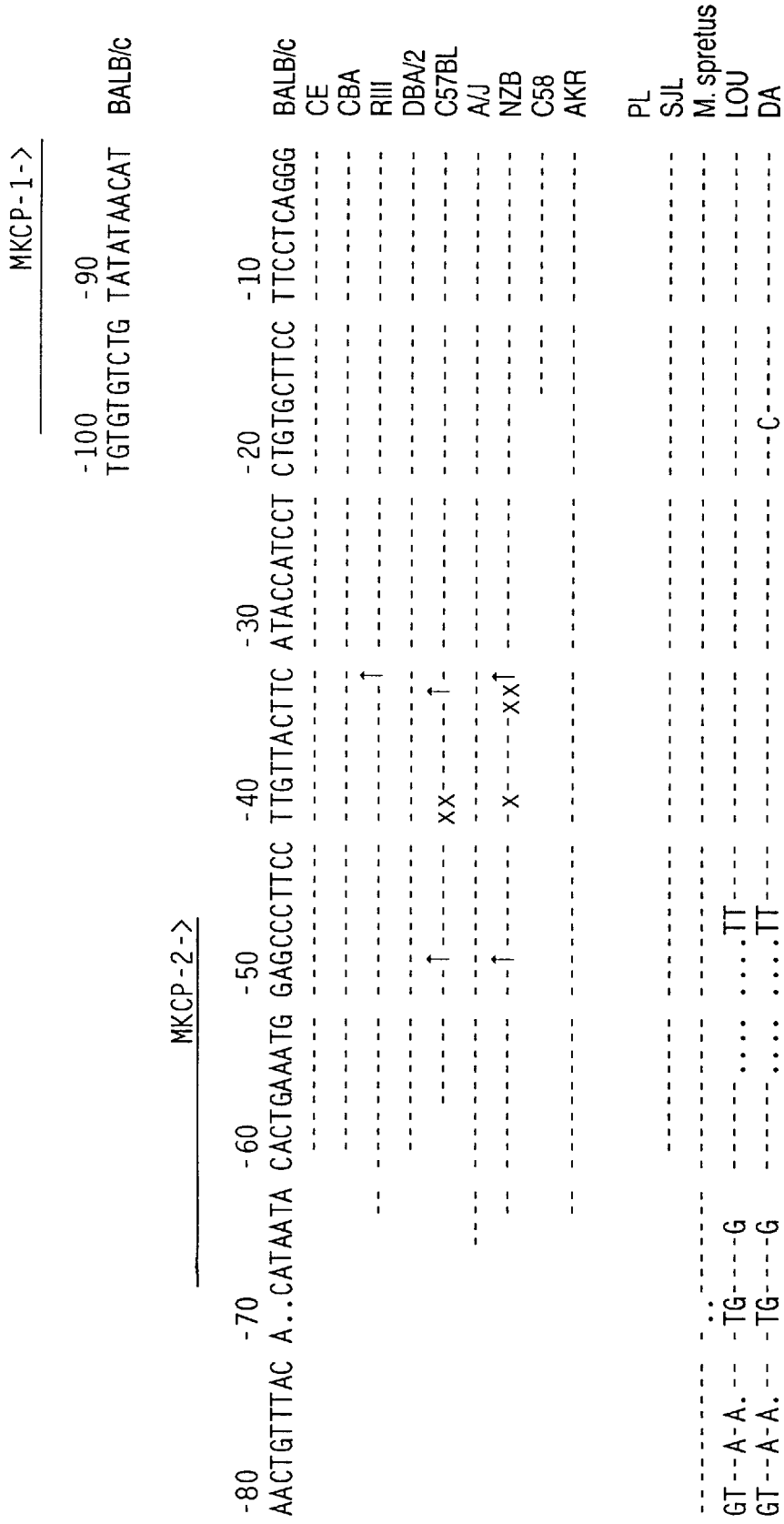

We have discovered a monoclonal anti-idiotype antibody, 3H1, which induces a specific immune response against a distinct and specific epitope of carcinoembryonic antigen (CEA), a tumor-associated antigen. This epitope is unique to CEA and is not present on other CEA-related lower molecular weight members of this family which are also found on normal tissues. The antigenic determinant as defined by the monoclonal antibody 8019 (Ab1) against which 3H1 was raised is absent on normal adult tissues as evidenced by immunoperoxidase staining and hematopoietic analysis. A hybridoma that produces 3H1 has been deposited with the American Type Culture Collection (ATCC), 12301 Parklawn Drive, Rockville, Md., U.S.A. 20852 on Dec. 15, 1995 under the provisions of the Budapest Treaty for the International Recognition of the Deposit of Microorganisms for the Purposes of Patent Procedure. It was accorded Accession Number HB12003.

We have also found that 3H1 is effective in eliciting an immune response (humoral and/or cellular) in individuals with advanced CEA-associated tumors. While not wishing to be bound by a particular theory, one way that this may occur is that the 3H1 combining site may present a region that partly resembles an epitope in CEA, in the context of other epitopes which renders it more immunogenic. Thus, the antibody of this invention is useful for the treatment of CEA-associated tumors in these individuals. It is also useful for detection of Ab1 or Ab3.

As used herein, the terms "3H1", "3H1 antibody" and "3H1 monoclonal anti-idiotype antibody" are used interchangeably to refer to immunoglobulin produced by the 3H1 hybridoma cell line deposited with the ATCC. Also included in the definition of 3H1 are fragments produced by enzymatic cleavage and/or chemical treatment of intact antibody that comprise both the entire heavy and light chain variable regions of 3H1 and are capable of binding 8019 (Ab1) in a standard immunoassay, such as Fab, F(ab')$_2$, and F(ab').

In one embodiment, the invention includes a monoclonal anti-idiotype antibody (referred to herein as an "anti-Id") produced by hybridoma cell line ATCC HB12003 or progeny thereof. Also included in this invention is a hybridoma cell line designated ATCC No. HB12003 and progeny thereof. As used herein, "progeny" of a hybridoma are descendants of a hybridoma, which may or may not be completely identical to the original (parent) cell due to mutation or other adaptation, but that produce a monoclonal antibody that maintains the ability to escape immune tolerance, i.e., to cause an immune reaction against CEA.

Generation of Monoclonal Anti-Idiotype Hybridomas and Selection of 3H1

3H1 was obtained by using the 8019 antibody as immunogen for an anti-idiotype response. 8019 binds to a unique epitope of CEA that is not present on other members of the CEA family, with virtually no cross-reactivity with normal adult tissues or hematopoietic cells including granulocytes. Koprowski et al. (1979) *Somatic Cell Genet.* 5:957; Mitchell (1980) *Cancer Immunol. Immunother.* 10: 1.

Syngeneic BALB/c mice were immunized four times with 8019 (Ab1) and their spleen cells were fused with the non-secretory mouse myeloma P3-653 cells. The screening procedure included four steps: (1) Positive selection for antibody binding to 8019 (2) Negative selection against antibody recognizing isotypic or allotypic determinants; (3) Positive selection for an ability to inhibit the binding of 8019 to CEA; (4) Positive selection for an ability to induce a humoral immune response against the original tumor-associated antigen (CEA) in both mice and rabbits.

Several Ab2 hybridomas were obtained that were specific for the immunizing Id of 8019 and did not react with any isotypic or allotypic determinants. To determine whether the anti-8019 were directed against the paratope of 8019, the binding of radiolabeled 8019 to plate bound CEA or the CEA-positive cell line LS174-T was studied in the presence of varying amounts of Ab2 hybridoma culture supernatants. With as little as 5 µl of culture supernatant, several of the anti-Ids tested inhibited the binding greater than 90%. Ab2 producing lines able to inhibit 8019 binding to CEA were grown and purified from ascites fluid for further studies.

Different purified Ab2 were prepared as vaccines and injected into naive mice and rabbits. After 3 or more injections, serum samples were titered for the presence of Ab3 that bound not only to the immunizing Ab2, but also to CEA. The Ab2 reproducibly inducing the highest titer of Ab3 with the desired specificity was designated 3H1. Further details of the method used to obtain 3H1 are provided in Example 1.

Ab3 produced in animals immunized with 3H1 has been further characterized. The immune sera from both mice and rabbits competed with Ab1 for binding to the CEA-associated cell line LS174-T and inhibited the binding of radioiodinated Ab1 to Ab2. This indicated that anti-anti-Id (Ab3) in mice and rabbits may share idiotopes with Ab1 (8019) and they probably bind to the same epitope as Ab1.

Monoclonal Ab3 that bind to CEA positive antigen have also been obtained from mice immunized with 3H1. The Ab3 (both polyclonal and monoclonal) reacted with semi-purified CEA Ag by dot blot analysis and stained LS174-T cells by immunoperoxidase method. Administration of 3H1 to non-human primates (cynomolgus monkeys) also generated an immune response (Example 3). Ab3 produced in response to 3H1 was specific for CEA.

Importantly, although humans with CEA-associated tumors are tolerized to the CEA antigen, we have discovered that 3H1 elicits an immune response in patients with advanced CEA-associated disease. Twelve patients with CEA-positive advanced colorectal carcinoma, and who had failed standard therapies, were administered 3H1. Nine of the twelve patients developed antibodies that were anti-CEA (FIGS. 23–27). In addition, seven of the twelve patients displayed a cellular immune response as evidenced by a T cell proliferation assay (FIG. 29). All seven of these patients had also developed an Ab3 response. This is the first demonstration of breaking immune tolerance to CEA in patients with advanced disease. A more detailed description of this study is found in Example 3.

We have also found the nucleic acid sequence encoding the light and heavy chain variable regions of 3H1 and the amino acid sequence of the light and heavy variable regions of 3H1. Thus, the present invention includes an anti-idiotype antibody having a light chain variable region amino acid sequence identical to that depicted in FIG. 1B (SEQ ID NO:2) and a heavy chain variable region amino acid sequence identical to that depicted in FIG. 2B (SEQ ID NO:4). The invention also encompasses an antibody having a light chain variable region encoded by a polynucleotide sequence identical to that depicted in FIG. 1A (SEQ ID NO:1) and a heavy chain variable region encoded by a polynucleotide sequence identical to that depicted in FIG. 2A (SEQ ID NO:3).

An "identical" polynucleotide or amino acid sequence means that, when the sequences are aligned, there is an exact match between bases (polynucleotide) or amino acids.

Example 2 describes the cloning of 3H1 cDNA, from which the amino acid sequence was deduced. To confirm our amino acid sequence, we sequenced the light and heavy chains of 3 H1 for 10–15 degradation cycles. The amino acid sequences obtained were identical to that deduced from the cDNA sequence.

The invention also includes an anti-idiotype antibody having a light chain variable region encoded by a polynucleotide encoding an amino acid sequence identical to that depicted in FIG. 1B (SEQ ID NO:2) and a heavy chain variable region encoded by a polynucleotide encoding an amino acid sequence identical to that depicted in FIG. 2B (SEQ ID NO:4). It is well within the skill of the art, given an amino acid sequence, to deduce a polynucleotide encoding the amino acid sequence.

Also included in this invention is a hybridoma cell line, samples of which are deposited in the American Type Culture Collection (ATCC), 10801 University Boulevard, Manassas, Va. 20110-2209, and given the deposit number HB12003, and progeny thereof. The invention also includes a hybridoma cell line that produces a monoclonal anti-idiotype antibody having a light chain variable region amino acid sequence identical to that depicted in FIG. 1B (SEQ ID NO:2) and a heavy chain variable region amino acid sequence identical to that depicted in FIG. 2B (SEQ ID NO:4). Plasmids encoding the light and heavy chain variable region amino acid sequences (along with a portion of the constant region) have been deposited with the American Type Culture Collection (ATCC), 10801 University Boulevard, Manassas, Va. 20110-2209 on Dec. 21, 1995 under the provisions of the Budapest Treaty for the International Recognition of the Deposit of Microorganisms for the Purposes of Patent Procedure. They were accorded Accession Nos. 97394 and 97395, respectively.

The invention also encompasses 3H1 conjugated to a label capable of producing a detectable signal. These conjugated antibodies are useful, for example, in detection systems such as quantitation of Ab1 (and/or Ab3) or imaging. Such labels are known in the art and include, but are not limited to, radioisotopes, enzymes, fluorescent compounds, chemiluminescent compounds, and bioluminescent compounds. The labels may be covalently linked to 3H1, or conjugated to the 3H1 through a secondary reagent, such as a second antibody, protein A, or a biotin-avidin complex. Methods of labeling antibodies are known in the art and need not be described in detail herein.

Preparation of 3H1

The antibody of this invention can be obtained several ways. 3H1 can be produced from the hybridoma ATCC No. HB12003 described herein. Methods of antibody isolation are well known in the art. See, for example, Harlow and Lane (1988) *Antibodies: A Laboratory Manual,* Cold Spring Harbor Laboratory, New York, and Sambrook et al. (1989) *Molecular Cloning: A Laboratory Manual,* Cold Spring Harbor Laboratory. The antibody can be obtained from the hybridoma via tissue culture or from mouse ascites. These techniques are known the art. For example, the cells can be cultured in a suitable medium, and spent medium can be used as an antibody source. Optionally, matrix-coated channels or beads and cell co-cultures may be included to enhance growth of antibody-producing cells. For the production of large amounts of antibody, it is generally more convenient to obtain an ascites fluid. Such methods are known in the art, and generally comprise injecting hybridoma cells into an immunologically naive histocompatible or immunotolerant mammal, especially a mouse. The mammal is optionally primed for ascites production by prior administration of a suitable composition; for example, Pristane. Preferably, 3H1 is purified from BALB/c ascites using recombinant protein G-agarose chromatography followed by Protein-A-CL-sepharose 4B chromatography.

Alternatively, 3H1 can be chemically synthesized using techniques known in the art, for example, using a commercially available automated peptide synthesizer such as those manufactured by Applied Biosystems, Inc. (Foster City, Calif.). 3H1 can also be obtained by employing routine recombinant methods such as described in Sambrook et al. (1989). For instance, a polynucleotide encoding either the 3H1 heavy or light chain can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of 3H1 may be produced separately, and then combined by disulfide bond rearrangement. Alternatively, vectors with separate polynucleotides encoding each chain of 3H1, or a vector with a single polynucleotide encoding both chains as separate transcripts, may be transfected into a single host cell which may then produce and assemble the entire molecule. Preferably, the host cell is a higher eucaryotic cell that can provide the normal carbohydrate complement of the molecule. The 3H1 thus produced in the host cell can be purified using standard techniques in the art. A polynucleotide encoding 3H1 for use in the production of 3H1 by any of these methods can in turn be obtained from the hybridoma producing 3H1, or be produced synthetically or recombinantly from the DNA sequence provided herein.

The 3H1 antibody is of the IgG1 mouse subclass, and may be isolated by any technique suitable for immunoglobulins of this isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. 3H1 may also be purified on affinity columns comprising the 8019 paratope; for example, in the form of a purified Ab1 or Ab3.

If 3H1 is to be administered to an individual, 3H1 is preferably at least 80% pure, more preferably at least 90% pure, even more preferably at least 95% pure as well as free of pyrogens and other contaminants. In this context, the percent purity is calculated as a weight percent of the total protein content of the preparation.

Uses for and Methods Using 3H1

3H1 has several uses. It can be used to elicit an immune response in an individual having advanced CEA-associated disease and thus treat those individuals for CEA-associated disease. Preferably, the immune response is anti-CEA. Further, 3H1 can be used to detect antibodies that bind to CEA or 3H1. 3H1 may also be used to remove unwanted excess labeled Ab1 from the circulation of patients previously treated with labeled monoclonal anti-CEA antibodies. The label may be any label attached to the antibody suitable for its intended use, including, for example, radioisotopes, toxic moieties such as toxins, and drugs. 3H1 is also useful for enhancing tumor detection in imaging.

Thus, the present invention includes methods of eliciting an immune response in a individual with advanced CEA-associated disease, such as CEA-associated tumors that entail administering an effective amount of 3H1 to the individual. Preferably, the response is the production of anti-CEA antibody. As used herein, an "individual" is a vertebrate, preferably is a mammal, and more preferably human. Mammals include, but are not limited to, farm animals, sport animals and pets. A "CEA-associated tumor" is one that contains an CEA antigen, especially expressed on the surface of tumor cells. As used herein, "advanced" CEA-associated tumors means that there is detectable metastasis, that is, detectable tumor masses at sites other than the primary site of the tumor. Masses are preferably detected by imaging techniques known in the art such as X-ray or CT scan. An "effective amount" is an amount sufficient to elicit an immune response, whether humoral and/or cellular. An effective amount can be administered in one or more administrations. Preferably, the immune response is the production of anti-CEA.

Suitable subjects for administration of 3H1 antibody may be identified by a number of different criteria. Experimental animals may be administered 3H1, for example, to study the effect of 3H1 on the immune response, or to obtain useful reagents, such as anti-CEA specific antibodies and cell lines.

In a preferred embodiment, 3H1 may be used for treatment of advanced CEA-associated disease, such as CEA-associated tumors. For treatment, an effective amount of 3H1 is administered to an individual with advanced CEA-associated tumor(s). As used herein, an "effective amount" for treatment is an amount sufficient to palliate the disease state. An effective amount can be given in one or more than one administration. Treatment of individuals with advanced CEA-associated disease with an effective amount of 3H1 may have any of the following effects in comparison with other individuals who are not so treated: decrease the rate of progression of the disease, stabilize the state of disease, prevent spread and/or cause remission. As used herein, "advanced" CEA-associated tumors means that there is detectable metastasis, that is, detectable tumor masses at sites other than the primary site of the tumor. Masses are preferably detected by imaging techniques known in the art such as X-ray or CT scan.

To elicit an immune response or treat an individual for an advanced CEA-associated tumor, 3H1 is administered to an individual parenterally, preferably intracutaneously. Other routes of administration include, but are not limited to, intramuscular and intradermal. 3H1 can also be administered indirectly, by treatment of cultured cells followed by introduction of these cultured cells into an individual.

The amount of 3H1 administered depends upon several factors, such as the condition of the individual and the route of administration. Typically, the dose per administration will range from about 0.1 mg to about 20 mg. More preferably, the dose will range from about 0.5 mg to about 10 mg; more preferably, from about 1 mg to about 8 mg. Preferably, the dose is about 1 mg to about 4 mg. 3H1 is typically administered bi-weekly for four injections, followed by monthly injections as required. Timing of subsequent injections (i.e., a maintenance dose) will depend, inter alia, upon the condition and response of the individual being treated. Ab3 levels can be monitored, preferably by the diagnostic methods described herein, to determine when maintenance (booster) administrations should be given, which could typically be about every three months.

Preferably, 3H1 is administered with a pharmaceutically acceptable excipient. A pharmaceutically acceptable excipient is a relatively inert substance that facilitates administration of a pharmacologically effective substance. For example, an excipient can give form or consistency to the vaccine composition, or act as a diluent. Suitable excipients include but are not limited to stabilizing agents, wetting and emulsifying agents, salts for varying osmolarity, encapsulating agents, buffers, and skin penetration enhancers. Examples of pharmaceutically acceptable excipients are described in *Remington's Pharmaceutical Sciences* (Alfonso R. Gennaro, ed., 18th edition, 1990).

Preferably, 3H1 is used with an adjuvant which enhances presentation of 3H1 or otherwise enhances the immune response against 3H1. Suitable adjuvants include aluminum hydroxide (alum), QS-21 U.S. Pat. No. 5,057,540) DHEA (U.S. Pat. Nos. 5,407,684 and 5,077,284) and its derivatives (including salts) and precursors (e.g., DHEA-S), beta-2 microglobulin (WO 91/16924), muramyl dipeptides, muramyl tripeptides (U.S. Pat. No. 5,171,568) and monophosphoryl lipid A (U.S. Pat. No. 4,436,728; WO 92/16231) and its derivatives (e.g., Detox™) and BCG (U.S. Pat. No. 4,726,947). Other suitable adjuvants include, but are not limited to, aluminum salts, squalene mixtures (SAF-1), muramyl peptide, saponin derivatives, mycobacterium wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875. For veterinary use and for production of antibodies in animals, mitogenic components of Freund's adjuvant can be used. The choice of an adjuvant will depend in part on the stability of the vaccine in the presence of the adjuvant, the route of administration, and the regulatory acceptability of the adjuvant, particularly when intended for human use. For instance, alum is approved by the United States Food and Drug Administration (FDA) for use as an adjuvant in humans. Preferably, alum-precipitated 3H1 is used. Preparation of aluminum hydroxide precipitated 3H1 is described in Example 3.

Alternatively, 3H1 can be encapsulated in liposomes. Liposomes suitable for packaging polypeptides for delivery to cells are known in the art. 3H1 can be heat treated before administration and the heat treatment can be in the presence of adjuvant, for example, alum. Heat treatment is preferably at 45° C. for 30 minutes in a sterile vial in a water bath. For instance, 3H1 can be heated at about 40 to 80° C., preferably 45° C. to 60 ° C., for a period of about 5 minutes to 2 hours, preferably 15 minutes to 1 hour. The heat treatment can occur anytime before administration. Preferably, heat treatment is within 7 days of administration. Other heat treatment procedures can be used, as long as the desired activity of 3H1 is not significantly compromised.

For the purpose of raising an immune response, 3H1 may be administered in an unmodified form. It may sometimes be preferable to modify 3H1 to improve its immunogenicity. As used herein, "immunogenicity" refers to a capability to elicit a specific antibody or cellular immune response, or both. Methods of improving immunogenicity include, inter alia, crosslinking with agents such as gluteraldehyde or bifunctional couplers, or attachment to a polyvalent platform molecule. Immunogenicity may also be improved by coupling to a protein carrier, particularly one that comprises T cell epitopes.

In order to determine the effect of administration with 3H1, the subject may be monitored for either an antibody (humoral) or cellular immune response against CEA, or a combination thereof.

To determine the level of CEA antibody (Ab3) in a biological sample, for example, serum or plasma is obtained from the subject. The sample may optionally be enriched for immunoglobulin before the assay is conducted, although this is not usually required. If a mouse immunoglobulin (such as 3H1) is to be used as an assay reagent, the sample is preferably pretreated to remove anti-mouse immunoglobulin activity. This may be performed, for example, by depletion on a mouse immunoglobulin column, or by mixing nonspecific mouse immunoglobulin into the sample and removing any immunoprecipitate formed.

To conduct the assay, anti-CEA that may be in the sample is contacted with a non-limiting amount of an antigenic equivalent of CEA. This may be isolated CEA, nitrocellulose with CEA affixed by direct blotting or by transfer from a polyacrylamide gel, cells expressing CEA (such as LS174T cells), membrane preparations from such cells, or fixed tissue sections containing CEA. Alternatively, an anti-idiotype, particularly 3H1, may be used.

Once the immune complex has formed, it is generally separated from uncomplexed CEA analog, and the amount of complex present is determined. The complex may be separated, for example, by centrifugation to collect cells or an immunoprecipitate, or capture by a solid phase. The amount of complex present may be measured by providing the CEA analog with a label either directly, or by incubating with a secondary reagent. Alternatively, a competition assay may be performed, in which the sample is first incubated with the CEA analog, and then a non-limiting amount of a labeled anti-CEA reagent is added which competes with the anti-CEA which may be present in the sample. Suitable labels include radiolabels, enzyme labels, fluorescent labels, and chemiluminescent labels. A standard curve is constructed using solutions known to contain no anti-CEA, and solutions with various relative concentrations of anti-CEA, in place of the sample. The sample containing the unknown amount of anti-CEA is generally assayed in parallel, and the relative amount of anti-CEA contained therein is determined by comparison with the standard curve. Preferred assays for determining anti-CEA levels using 3H1 antibody are described in more detail in a following section.

The isotype of the anti-CEA antibody may be determined by including in the immunoassay an isotype-specific reagents, either at the separation or the labeling stage. For example, anti-human IgG may be used to separate or detect antibody of the IgG class present in a clinical sample of human origin. Presence of specific anti-CEA of the IgG class generally indicates a memory response. Presence of anti-CEA of the IgM class generally indicates ongoing immunostimulation, such as may be due to the presence of an CEA expressing tumor, or ongoing treatment with 3H1.

If desired, anti-CEA antibody detected in a biological sample may be further characterized; for example, by competition with anti-8019 (Ab1) to determine whether they are specific for related epitopes on CEA. Competition assays between Ab1 and Ab3 are described in detail in the Example section.

Anti-CEA antibody may also be tested to determine whether it is cytotoxic. Complement mediated cytotoxicity (CMC) is determined, for example, by using CEA-expressing target cells (such as LS174-T) labeled with $^{51}$Cr. Labeling may be accomplished by incubating about $10^6$ cells with ~200 $\mu$Ci Na$_2^{51}$CrO$_4$ for 60 minutes at 37° C., followed by washing. The assay is conducted by incubating the antibody (or clinical sample containing the antibody) with the target cells. The opsonized cells are then washed and incubated with a source of complement; for example, guinea pig serum pre-adsorbed to remove intrinsic antibody activity. After a suitable incubation period at 37° C., release of $^{51}$Cr into the medium is determined and compared with that from unopsonized control cells. Release of 51Cr correlates with CMC activity.

Another way of characterizing the anti-CEA antibody is by testing its ability to participate in an ADCC response (Cheresh et al. (1986), Cancer Res. 46:5112). Radiolabeled CEA-expressing target cells are incubated with the anti-CEA (in the form of heat-inactivated serum), and effector cells. Normal human peripheral blood mononuclear cells (PBMC) are suitable effector cells, and preferably are used at an effector:target ratio of about 100. After approximately 4 hours at 37° C., the proportion of released $^{51}$Cr is determined as a measure of ADCC activity.

The cellular immune response in a subject being administered 3H1 may be quantified by conducting standard functional assays for specific T cell activity.

One type of assay measures T cell proliferation. In this test, peripheral blood mononuclear cells (PBMC) are obtained from a whole blood sample collected from the treated subject. For experimental animals, spleen cells may also be used. T cells may be enriched, for example, by centrifugation on a gradient such as Ficoll™. The cells are then cultured in the presence of CEA or (more usually) irradiated CEA expressing cells at various concentrations. Preferably, the stimulator cells are autologous with the responder cells, particularly in terms of histocompatibility Class II antigens.

Another type of assay measures T cell cytotoxicity. In this test, an enriched T-cell population is used to effect lysis of $^{51}$Cr-labeled CEA expression target cells, prepared as described above. Preferably, the effector cells are autologous with the target cells, particularly in terms of histocompatibility Class I antigens. The T cell population may optionally be pre-stimulated with CEA or a relevant cell line. The T cells are then combined at various ratios with about $10^4$ labeled target cells; for example, in wells of a microtiter plate. The plate is optionally centrifuged to initiate cell contact, and the cells are cultured together for 4–16 hours at 37° C. The percent specific release of 51 Cr into the medium is measured in comparison with labeled targets cultured alone (negative control) and targets lysed with a detergent such as 0.1% Triton™ X-100 (positive control).

Other relevant measurements to determine the effect of 3H1 administration include clinical tests as may be appropriate in determining the progression of cancer of the suspected type. Such tests may include inflammatory indicators, mammography, and radioscintigraphy, such as are described elsewhere in this disclosure.

Use of 3H1 to Conduct Immunoassays

Another way that 3H1 can be used is to assay for the presence of an antibody or other immune component that binds to 3H1, or to CEA. Such components may be present following therapeutic administration of 3H1, or may spontaneously arise due to the presence of an CEA-expressing tumor in an immunocompetent host. Assays may be conducted on biological samples, usually clinical samples. As used herein, the term "biological sample" includes cells in culture, cell lysates, cell supernatants, serum, plasma, biological fluids, and tissue samples.

In one embodiment of this invention, 3H1 is used to detect the presence of an anti-CEA, particularly anti-3H1 idiotype, that may be present in a biological sample. The sample is suitably prepared before conducting the assay, optionally by enriching for antibody activity. If the biological sample is suspected of containing antibody activity against non-idiotypic regions of 3H1 (particularly anti-mouse immunoglobulin), it is preferable to remove them or conduct the assay so as to avoid their detection. Anti-mouse immunoglobulin antibody can be removed from a sample, for example, by precipitation with normal mouse IgG or adsorption with a mouse Ig adsorbant. Binding of anti-mouse immunoglobulin antibody, particularly that specific for the Fc region, can be minimized by judicious choice of the reagents of the assay. F(ab')$_2$ or Fab fragments of 3H1 and other mouse immunoglobulin reagents are especially appropriate.

After the sample is suitably prepared, it is mixed with a excess functional equivalent of 3 H1 under conditions that permit formation of a complex between 3 H1 and any anti-CEA that may be present. The amount of complex is then determined, and compared with complexes formed with standard samples containing known amounts of anti-CEA in the range expected. Complex formation may be observed by immunoprecipitation or nephelometry, but it is generally more sensitive to employ a reagent labeled with such labels as radioisotopes like $^{125}$I, enzymes like peroxidase and β-galactosidase, or fluorochromes like fluorescein.

Antibody assays may be conducted in fluid phase. For example, anti-CEA may be mixed with labeled 3H1. Alternatively, the anti-CEA in the sample may be used to compete with a labeled anti-CEA for binding sites on 3H1. Generally, bound and unbound label is separated to quantitate the percent bound. Suitable separation methods include gel filtration chromatography, and precipitation with antibody against immunoglobulin of the species from which the sample is obtained, optionally in the presence of polyethylene glycol. Alternatively, the proportion of bound and unbound label may be determined in situ, for example, using fluorescence/quench labeling pairs or enzyme/inhibitor labeling pairs. See, e.g., U.S. Pat. No. 3,996,345 (Ullman et al.).

It is generally more convenient to conduct a capture assay using a reagent linked to a solid phase, such as a polyethylene test tube, microtiter plate well, or magnetic bead. In a competition-type capture assay, unlabeled anti-CEA in the sample competes with a labeled anti-CEA reagent for binding to 3H1. The 3H1 may be attached directly to the solid support, or captured later, for example, using an anti-3H1. In this assay, the amount of label associated with the solid phase is inversely related to the amount of anti-CEA in the sample.

In the sandwich-type capture assay, anti-CEA is captured by 3H1 attached directly or through a secondary reagent to a solid phase. After washing, the anti-CEA is detected using anti-immunoglobulin of the appropriate species, or a second 3H1 antibody, to which a label is directly or indirectly attached. Alternatively, the anti-immunoglobulin may be attached to the solid phase and labeled 3H1 is used to complete the sandwich. If the anti-immunoglobulin used is isotype-specific, then the class of the antibody may also be determined. In this type of assay, the amount of label associated with the solid phase correlates positively with the amount of anti-CEA in the sample.

Other methods of measuring specific antibody are known in the art, and may be adapted to measure anti-CEA by using 3H1 as the target antigen. All such adapted methods are embodied in this invention. Further descriptions of particular embodiments are provided in the Example section.

3H1 may also be used to measure the level of cellular anti-CEA activity, particularly anti-3H1 idiotype. In a preferred example, 3H1 is used to identify anti-CEA T cells, defined for this purpose as lymphocytes expressing a T cell receptor that binds the 3H1 idiotype. 3H1 may be labeled and contacted with a population of cells suspected of containing anti-CEA T cells. Alternatively, unlabeled 3H1 may be mixed with the cells, and followed with a labeled secondary reagent such as labeled anti-mouse immunoglobulin or protein A. Suitable labels for this purpose include radiolabels and fluorescent labels. The use of fluorescent labels would also allow anti-CEA cells to be separated from non-specific cells in a fluorescence-activated cell sorter.

Use of 3H1 to remove labeled Ab1

The invention also encompasses methods using 3H1 to remove a toxin and/or a label, for example radioactivity, from an individual who has received a labeled anti-CEA antibody (Ab1), for example, for radioscintiligraphy or radiotherapy. One problem common to use of antibody targeted radionuclides (i.e., radioimmunotherapy) has been the presence of excess Ab1 in the system which limits the dosage of radiolabeled antibody for treatment. Further, effective imaging using radiolabeled antibodies is hampered due to excess circulating radiolabeled antibody, which often takes several days to clear circulation and tissues. In these methods of the present invention, 3H1 is administered to the individual at a specified time after administration of the labeled anti-CEA. The intention is for the 3H1 to complex with anti-CEA at sites other than the tumor, such as in the circulation and interstitial spaces, and thereby promote its clearance. As a result, the level of labeled moiety (such as radioisotope) in unaffected tissues is reduced, and the image of the tumor (in comparison to neighboring tissues) is enhanced. Similarly, when radionuclides are given to subjects for irradiation of a tumor site, it is desirable to reduce collateral exposure of unaffected tissue. This invention thus includes methods of treatment in which a radiolabeled anti-CEA antibody is administered in a therapeutic dose, and followed by a molar excess of 3H1.

In either of these applications, an amount of 3H1 is chosen that is in sufficient molar excess over the labeled anti-CEA to locate and bind any anti-CEA that is not localized at the tumor site. The timing of administration and amount of 3H1 will depend upon the nature of the radiolabeled antibody, the type of radioisotope used and the condition of the individual. Preferably, the molar ratio of 3H1 to the anti-CEA antibody is at least about 5:1, more preferably about 25:1 to 200:1. Preferably, 3H1 is administered 5 to 24 hours after the individual has received the anti-CEA antibody.

The invention also includes methods of detecting the presence of an anti-CEA antibody bound to a tumor cell comprising the steps of treating the tumor cell with 3H1 for a sufficient time to allow binding to the anti-CEA antibody, and detecting the presence of any complex formed. The intention is for the 3 H1 to detect anti-CEA that has pre-attached to the tumor cell; or alternatively, to promote the binding of anti-CEA to the tumor cell by forming a polyvalent anti-CEA/3H1 immune complex. In the former instance, the 3H1 is provided with a detectable label or a means by which a label can be attached. In the latter instance, either the anti-CEA or the 3H1 is provided with a label.

This strategy may be used, for example, to identify an CEA-bearing cell in an isolated cell suspension. The cells are incubated sequentially or simultaneously with anti-CEA and 3H1, washed, and then the labeled cells are detected. Preferred labels for this embodiment include fluorescent labels, such as fluorescein, rhodamine, and Texas red. Optionally, labeled cells may be separated from unlabeled cells; for example, by sorting in a fluorescence-activated cell sorter or by affinity separation, using any of the solid phase positive or negative immunoselection techniques known in the art.

The strategy may also be used, for example, to detect or image tumors in an affected subject. The anti-CEA and 3H1 are administered (usually sequentially) into the subject and allowed to accumulate at the tumor site. Suitable labels include radiolabels such as $^{111}$In, $^{131}$I and $^{99m}$Tc. The tumor is then detected or visualized using standard techniques of radioscintigraphy.

Pharmaceutical compositions and vaccines comprising 3H1 The present invention encompasses pharmaceutical compositions and vaccines containing 3H1. Such pharmaceutical compositions and vaccines are useful for eliciting an immune response, preferably an anti-CEA response, and/or treating an CEA-associated disease. These pharmaceutical compositions, comprised of an effective amount of 3H1 in a pharmaceutically acceptable excipient, are suitable for systemic administration to individuals in unit dosage forms, sterile parenteral solutions or suspensions, sterile nonparenteral solutions or oral solutions or suspensions, oil in water or water in oil emulsions and the like. Formulations or parenteral and nonparenteral drug delivery are known in the art and are set forth in *Remington's Pharmaceutical Sciences*, 18th Edition, Mack Publishing (1990).

One type of pharmaceutical composition is a vaccine. Accordingly, the present invention also includes vaccines comprising an effective amount of 3H1. As used herein, a "vaccine" is a pharmaceutical composition for human or animal use, which is administered with the intention of conferring the recipient with a degree of specific immunological reactivity against a particular target, or group of targets. The immunological reactivity may be antibodies or cells (particularly B cells, plasma cells, T helper cells, or cytotoxic T lymphocytes and their precursors or any combination thereof) that are immunologically reactive against the target. For purposes of this invention, the target is tumor associated antigen CEA or any related tumor antigen bound by 3H1. The immunological activity may be desired for experimental purposes, for treatment of advanced CEA-associated disease, or elimination of a particular substance. The vaccines can be used, inter alia, to elicit an immune response in an individual with advanced CEA-associated disease. Preferably, the immune response is the production of anti-CEA.

Preferably, a vaccine of this invention will include an adjuvant. Examples of adjuvants have been discussed above.

The vaccines of the present invention are typically administered parenterally, by injection for example, either subcutaneously, intramuscularly, intraperitoneally or intradermally. Administration can also be intranasal, intrapulmonary (i.e., by aerosol), oral and intravenous. Additional formulations which are suitable for other modes of administration include suppositories and, in some cases, oral formulations. The route of administration will depend upon the condition of the individual and the desired clinical effect.

Administrations can begin on a weekly or biweekly basis until a desired, measurable parameter is detected, such as elicitation of an immune response (humoral and/or cellular). Administration can then be continued on a less frequent basis, such as biweekly or monthly. Preferably, the administrations are initially given biweekly for the first four administrations, followed by monthly administrations.

The vaccines are administered in a manner compatible with the dosage formulation, and in such amount as will be therapeutically effective. The quantity to be administered depends on the individual to be treated, the capacity of the individual's immune system to synthesize antibodies, the route of administration, and the degree of protection desired. Precise amounts of active ingredient required to be administered may depend on the judgment of the practitioner in charge of treatment and may be peculiar to the individual. General dosage ranges for 3H1 have been given above.

Kits comprising 3H1

The present invention also encompasses kits containing 3H1, preferably diagnostic kits. Diagnostic procedures using 3H1 can be performed by diagnostic laboratories, experimental laboratories, practitioners, or private individuals. Kits embodied by this invention include those that allow someone to conduct an assay for anti-CEA or anti-3H1 activity, such as any of those disclosed herein, thus detecting or quantitating these activities.

The kits of this invention comprise 3H1 in suitable packaging. The kit may optionally provide additional components that are useful in the procedure, including, but not limited to, buffers, capture reagents, developing reagents, labels, reacting surfaces, means for detection, control samples, instructions, and interpretive information.

The following examples are provided to illustrate but not limit the present invention.

EXAMPLES

Example 1

Generation and Characterization of 3H1 Anti-Idiotype Antibody

The monoclonal anti-idiotype antibody producing hybridoma cell line 3H1 was created and identified according to the following description. Aspects of both the immunization procedure and the screening procedure were important to obtain an antibody with the desired specificity and functionality. 3H1 was one of a number of Ab2 that were initially produced, and was identified as the candidate with the most desirable features.

The immunizing antibody (Ab1) was the mouse anti-CEA monoclonal antibody 8019. Since the responding animal was also a mouse, the Ab2 generated were expected to be directed against idiotypic features of 8019. However, only a fraction of those would be directed against the 8019 paratope, an even smaller proportion would be immunogenic and capable of eliciting an Ab3, and a still smaller proportion would elicit Ab3 that cross-reacted with the tumor-associated antigen.

To render 8019 sufficiently immunogenic in an autologous species, it was conjugated to the carrier KLH, and emulsified in Freund's adjuvant. It was administered repetitively into the recipient animals on an unusual schedule with only 2 weeks between doses. Five mice were immunized according to this schedule. Substantial responses arose in about 3 mice only after the fourth immunization. Responding animals were boosted with a fifth dose of 8019 i.v., spleen cells were isolated, and hybridomas were prepared separately from each animal. Cloning was performed according to standard techniques.

Initial screening was conducted by immunoassay to identify the clones that reacted with 8019, but not with other target monoclonal antibodies sharing the same allotypic or isotypic determinants. A critical assay was a sandwich RIA in which 8019 is attached to a solid phase, overlaid with culture supernatant, and developed with radioiodinated 8019. This assay requires the antibody in the hybridoma supernatant to be functionally bivalent, and be able to span between the capture 8019 and the developing 8019. Several clones that were idiotype specific and gave a strong signal in this assay were selected for further study.

Subsequent screening was conducted by competition assays, in which the Ab2 was required to block the binding of 8019 to CEA. This established that Ab2 recognized the paratope of 8019. CEA was provided in the form of MCF-7 cells, a human breast cell tumor line expressing CEA at the cell surface. The nature of the assay requires the Ab2 to block the interaction between 8019 and the tumor antigen in its particular manner of presentation on tumor cells. At a minimum, candidate Ab2 which had passed the earlier screening tests were required to inhibit the binding of 8019 to the cells by at least 85%. There were about three Ab2 that substantially exceeded the minimum, with 3H1 providing about the highest level of inhibition.

The ultimate screening test was a determination of whether the candidate Ab2 were capable of eliciting an Ab3 of the desired specificity when injected into a recipient. Sufficient quantities of Ab2 were prepared from mouse ascites, and tested in mice and rabbits. Sera from the test animals were first assayed for the presence of Ab3 in a sandwich immunoassay using the same labeled Ab2 used for immunization. Sera testing positively were then assayed for ability of the Ab3 to react against the tumor-associated antigen; namely CEA. A semipure preparation of CEA was used to coat microtiter plates, overlaid with the test serum in serial dilutions, and the Ab3 that bound was detected using labeled anti-immunoglobulin. The titer of the Ab3 binding to CEA defined the "quality" of Ab2, as a reflection of its capacity as an inducer of anti-CEA.

Monoclonal antibody 3H1 emerged as the anti-idiotype with the highest quality, and is the basis for various compounds, compositions, and procedures embodied in this invention.

Materials Carcinoembryonic antigen (CEA): Purified CEA was obtained commercially from Rougler Biotech, Montreal, Canada (cat. no. 70015). Alternatively, CEA was isolated from human liver metastasis of colonic adenocarcinoma by perchloric acid extraction and purified twice by ion-exchange chromatography, followed by gel filtration and several steps of HPLC chromatography. CEA obtained by this method was 100% pure, produced a single band at 180,000 m.w. by HPLC and SDS-PAGE and was immunoprecipitated as a single band by horse as well as rabbit anti-CEA antibody. Two closely migrating bands of 180,000 and 200,000 m.w. were demonstrated by Western blot analysis using 8019 antibody and other murine mAb anti-CEA. The purified CEA was used for ELISA experiments with mouse and rabbit polyclonal Ab3 sera, described supra.

Other experiments were generally conducted using a semipurified extract from human adenocarcinoma cells. This was prepared by perchloric extraction followed by extensive dialysis. The presence of CEA in the extract was confirmed by SDS-PAGE, followed by immunoprecipitation with mAb 8019.

Antibody. The hybridoma cell line producing monoclonal antibody 8019 was obtained from the American Type Culture Collection (ATCC, Rockville, Md.). The antibody was originally described as an IgM κ, but during recloning a spontaneous switch mutant appeared, and our 8019 is an IgG1 κ. The specificity of 8019 was reconfirmed by immunoperoxidase staining and flow microfluorimetry analysis using cells expressing CEA. Monoclonal antibody 1E3 mAb (IgG1 κ; specific for human mucinous ovarian carcinoma) and other monoclonal and myeloma mouse immunoglobulins were used as controls in various experiments herein described.

Ascites of 8019 hybridomas and other cell lines were prepared by injecting individual pristane-primed mice i.p. with 2–10×10$^6$ viable cells. The IgG fraction was isolated from ascites by 45% saturated ammonium sulfate precipitation and subsequent chromatography on Protein A Sepharose(TM) CL-4B (Ey et al. (1978) *Immunochemistry* 15:429). The purity of the isolated IgG was checked by immunodiffusion, immunoelectrophoresis, and high pressure liquid chromatography (HPLC) fractionation.

Preparation of F(ab')$_2$fragments of 8019.The F(ab')$_2$ fragments were prepared by standard pepsin digestion (Parham (1983) *J. Immunol.* 131:2895). Briefly, the IgG fraction from the 8019 ascites was dialyzed against 0.1 M citrate buffer, pH 3.5, and digested with pepsin (25 μg/mg IgG) at 37° C. for 8 h. After cleavage, the pH was adjusted to 7.0 with 3.0 M tris buffer, pH 8.6, and the solution was dialyzed against phosphate-buffered saline (PBS) in the cold. The digest was separated by HPLC using a Sepharose 6 column. The purity of the isolated F(ab')$_2$ was determined by immunodiffusion and by reaction with anti-isotype reagents in a standard ELISA.

Coupling of antibody with KLH: 8019 was coupled to keyhole limpet hemocyanin (KLH) according to a method described by Maloney et al. (1985; Hybridoma 4:191). Antibody stock solution (1 mg/ml) was mixed with KLH (1 mg/ml) in PBS in the presence of freshly diluted glutaraldehyde solution (final concentration 0.05%). The mixture was rotated end-over-end for 1 h at room temperature, and then dialyzed exhaustively against PBS at 4° C. Immunization of syngeneic BALB/c mice: BALB/c females were immunized four times over a period of 2 months. The first injection was given i.p. using 100 μg of 8019, emulsified in complete Freund's adjuvant. The next two injections were given with 100 μg of 8019 coupled to KLH in incomplete Freund's adjuvant, either s.c. or i.p. Mice were bled from time to time, and sera were checked for anti-Id activity by ELISA in a binding assay by using F(ab')$_2$ fragments of 8019 and normal pooled BALB/c mouse serum IgG as control. Three days before the fusion, the mice were boosted i.v. with 8019 in PBS.

Production of anti-idiotype hybridomas

The fusion partner used to produce the hybridoma lines was the mouse non-secretory myeloma cell line P3-653, ancestrally related to P3X63Ag8.653, available from the ATCC as No. CRL-1580. Established human cell lines were cultured in RPMI 1640 supplemented with 5% fetal calf serum as described elsewhere (Seon et al. (1984) *J. Immunol.* 132:2089).

Hybridomas were produced essentially following the method of Oi and Herzenberg ((1980) "Selected Methods of Cellular Immunology", Mishell & Shiigi eds., Freeman Publs., at 351–372). Spleen cells from immunized mice were mixed with P3-653 cells at a ratio of 1:1 to 1:10, in the presence of 50% polyethylene glycol (PEG, mw ~4500). Fused cells were then washed and cultured. Hybrids were selected using hypoxanthine-aminopterin-thymidine media. Initial selection of anti-idiotype antibody (Ab2) secreting hybridoma clones:

Initial screening of the hybridoma clones was performed by RIA and ELISA. The ELISA was conducted by coating microtiter plate wells with 8019 antibody (or control) at 500 ng/well. After incubating overnight at 4° C., the plates were blocked with 1% bovine serum albumin (BSA) in PBS. 100 μl of hybridoma culture supernates or 20× concentrate was incubated in the well for 4 h at room temperature. After washing with PBS, the plates were further incubated for 4 h at room temperature or overnight at 4° C. with alkaline phosphatase-labeled anti-isotype reagents, and developed with the substrate. Because the ELISA detecting reagents were anti-mouse immunoglobulin, the 8019 used to coat the plates was an F(ab')$_2$ fragment. The ELISA assay is useful in identifying the class and subclass of specific antibody.

Generally, antibody of certain IgG subclasses is desired because it is stable, easily purified by protein A chromatography, and may have useful effector functions.

Hybridoma supernatants were also tested in a sandwich RIA. Purified 8019 was radioiodinated by the chloramine T method (Hunter (1970) *Proc. Soc. Exp. Biol. Med.* 133:989). 8019, or control antibody (monoclonal antibodies of various isotypes and unrelated specificities, and BALB/c normal IgG) was coated onto PVC plates at 500 ng/well. Generally, intact antibody was used. After incubating overnight at 4° C., the plates were blocked with 1% BSA in PBS. Coated plates were incubated with serial dilutions of hybridoma supernatant for 4 h, and developed using ~50,000 cpm of $^{125}$I-8019. The RIA assay is a more stringent specificity test for the antibody, and also requires that the antibody be able to span between two 8019 molecules.

A number of monoclonal Ab2 secreting cell lines emerged from these screening assays with the desired properties. Amongst them was monoclonal antibody 3H1.

Confirmation that Ab2 are specific for 8019 idiotype

Figure 5:
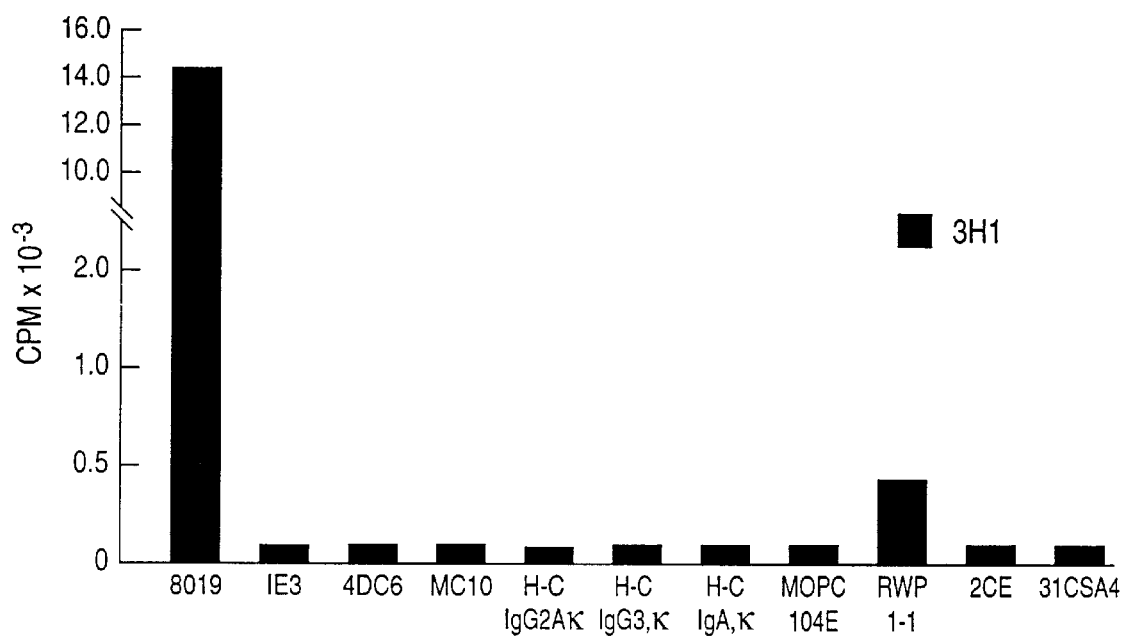
FIG. 5 is a bar graph comparing the reactivity of 3H1 with various antibodies. $^{125}$I-3H1 was tested against a panel of mAb of various specificities belonging to major Ig subclasses by a direct binding RIA.

Idiotype specificity of Ab2 was confirmed by direct binding to Ab1. Various purified Ab2 were labeled with $^{125}$I, and tested for binding to plates coated with a panel of monoclonal anti-TAA Ab1. Results for an experiment using $^{125}$I-3H1 are shown in FIG. 5. The results are presented in mean cpm (n=3, S.D.<10%). 3H1 bound almost exclusively to 8019; there was virtually no cross-reactivity with any of the other Ab1 tested, with a single exception: Minor cross-reaction with anti-CEA antibody RWP 1.1 (IgG2b, κ) that recognizes a related (possibly overlapping) epitope on CEA.

Specificity for the 8019 idiotype was further established in competition experiments. ~25,000 cpm of various labeled Ab2 was mixed with different members of a panel of unlabeled competitors comprising Ab2, Ab1, and other mouse immunoglobulins. The Ab2 was then tested for binding to 8019 coated plates. Results are shown in Table 1 (mean cpm, n=3, S.D.<10%). Greater than 90% inhibition was obtained using 250 ng of unlabeled 3H1 or 8019 as competitor. Virtually no inhibition was obtained, up to a concentration of 5 μg, using the other immunoglobulins as potential competitors, except for the related Ab 1 antibody RWP 1.1.

TABLE 1

Inhibition of Id-anti-1d binding*

| Inhibitor | cpm Bound | Percent Inhibition |
|---|---|---|
| None | 11,995 | 0 |
| 3H1 (Ab2), 0.125 μg | 439 | 97 |
| 8019 (Ab1), 0.200 μg | 861 | 95 |
| RWP 1.1, 5 μg (anti-CEA) | 1,842 | 85 |
| 1E3, 5 μg (anti-iso, allotype) | 11,755 | 2 |
| Mc-10, 5 μg (anti-iso, allotype) | 12,085 | 0 |
| F36/22, 5 μg (anti-iso, allotype) | 11,558 | 4 |
| 3F3, 5 μg (anti-CEA) | 10,955 | 8 |
| ZCE, 5 μg (anti-CEA) | 12,033 | 0 |
| 31C5A4, 5 μg (anti-CEA) | 11,800 | 1 |
| D-14, 5 μg (anti-CEA) | 12,075 | 0 |

Screening for anti-idiotypes directed against the 8019 paratope

To determine whether the Ab2 were directed against the paratope of 8019, the Ab2 were used to compete for the binding of radiolabeled 8019 to CEA. This was performed two ways: (1) plate-binding assays were conducted using the semipurified CEA extract; (2) cell binding assays were conducted using LS174-T cells, a human colon cancer cell line expressing CEA as a membrane constituent.

Plate-binding assays were coated by incubating plates with 100 μl of the perchloric acid solubilized semipurified CEA Ag extract (0.1 mg protein/ml) overnight at 4° C. LS 174-T cells were grown as confluent monolayer in 96-well tissue culture plates. Various dilutions of the test Ab2 (either culture supernatant or purified antibody) were mixed with the labeled 8019, and then added to the coated plate or cultured cells. Percent inhibition of the assay was calculated according to the formula:

$$\% \text{ inhibition} = 1 - \left(\frac{R_T - R_C}{R_{MAX} - R_C}\right) \times 100$$

where $R_T$ is the average cpm of the experimental well with inhibitors; $R_C$ is the average background cpm; and $R_{MAX}$ is the average maximum binding without any inhibitors.

Figure 6:
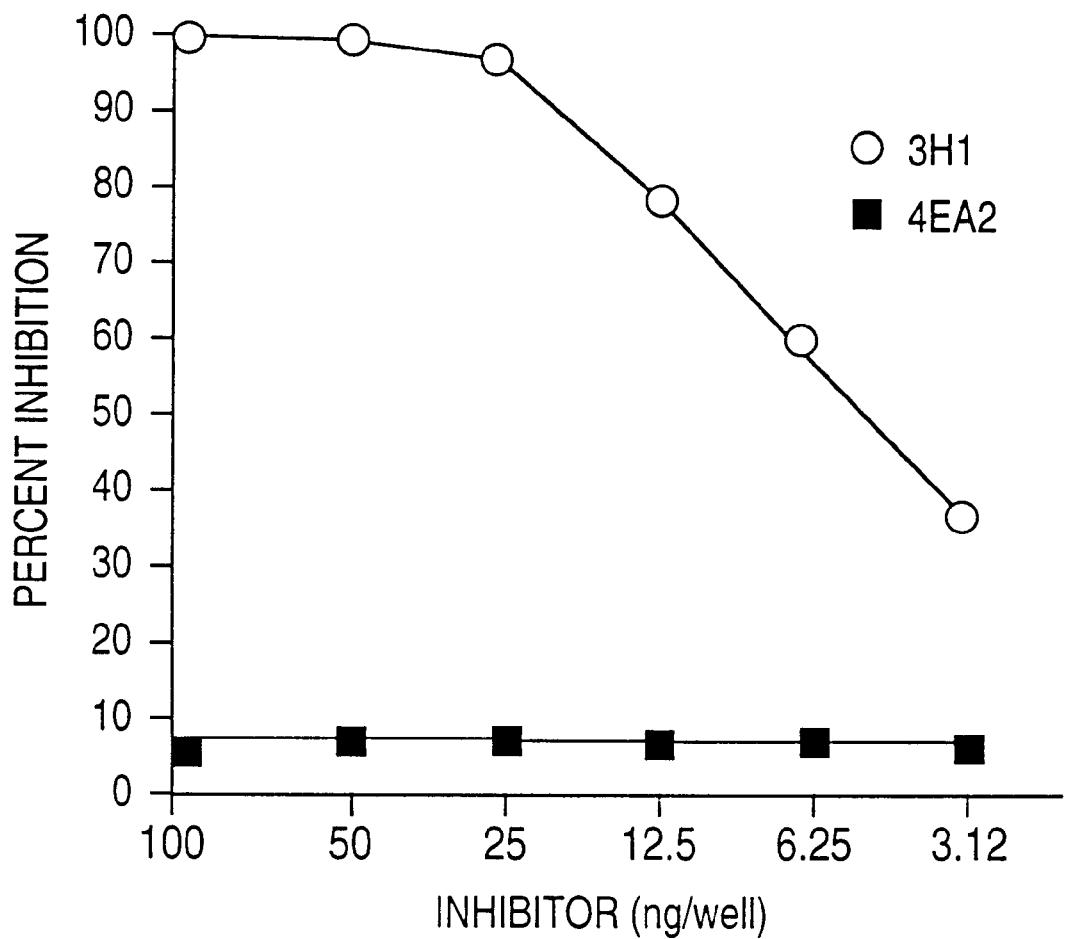
FIG. 6 is a graph depicting inhibition of binding of radiolabeled 8019(Ab 1) to semipurified CEA by 3H1. Circles denote 3H1; squares denote 4EA2, and unrelated antibody. 3H1 inhibited the binding 100% beginning at a concentration of 25 ng.

FIG. 6 shows results of this type of experiment, conducted using 3H1 as the model competitor in the plate-binding assay. 3H1 inhibited the binding of labeled 8019 to the CEA at amounts as low as 25 ng. Purified antibody 4EA2 (an IgG1, k of unrelated specificity) was used as a negative control, and demonstrated no inhibition. In a related experiment, 3H1 was not able to inhibit the binding of another anti-CEA antibody (D14) to the CEA-coated plates.

Confirmation of the binding specificity

For the most promising Ab2, confirmation experiments were conducted to confirm the specificity of binding to 8019, in which the roles in the competition assay were reversed.

About 40,000 cpm of $^{125}$I-8019 was coincubated with a semipurified preparation of CEA Ag, or else with a nonrelated glycoprotein Ag that does not react with 8019 (Bhattacharya et al. (1982) *Cancer Res.* 42:1560). The antibody-Ag mixture was added to Ab2-coated plates (500 ng/well), and the ability of CEA to inhibit the binding was determined. The amount of Ab2 was non-limiting with respect to the amount of 8019 that could bind, and was therefore a sensitive indicator for small amounts of competing CEA.

Figure 7:
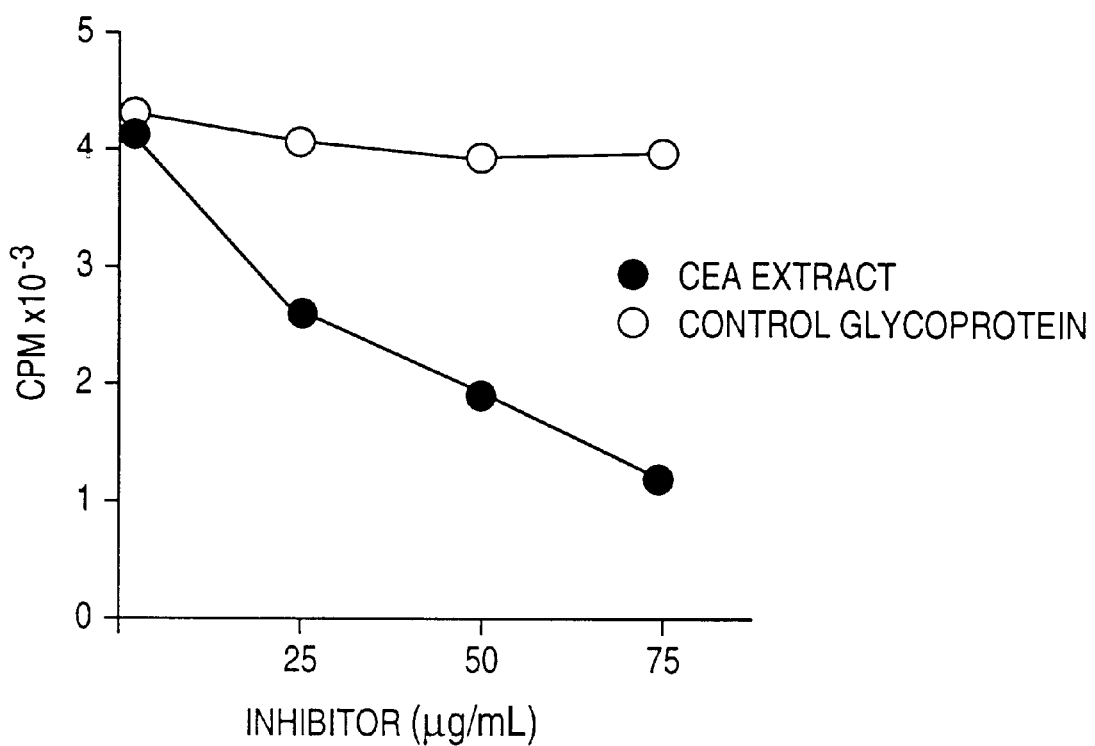
FIG. 7 is a graph depicting the inhibition of binding of 8019(Ab1) to 3H1 by CEA. Closed circles denote semipurified CEA; open circles denote a control glycoprotein that does not bind to 8019. Semipurified CEA at 2.5 μg inhibited the binding of anti-Id 3H1 to iodinated 8019 by 50%, whereas the unrelated glycoprotein even at higher concentration did not inhibit binding.

FIG. 7 shows the results of a typical experiment. 2.5 μg of semipurified CEA inhibited the binding of a3H1 to iodinated 8019 by 50%. The unrelated glycoprotein even at higher concentration did not inhibit binding. This suggests that 3H1 is a binding site-specific anti-Id.

Antibody-producing clones testing positively in the screening tests described so far were used to prepare mouse ascites as a source of Ab2. The Ab2 were purified by chromatography using Protein A and Protein G affinity resins by standard techniques.

Screening for anti-idiotypes capable of eliciting a tumor-specific immune response If the Ab2 behaves as a network antigen, then it should induce the production of Ag-specific Ab3 in the absence of exposure to Ag in a genetically unrestricted way and across species barriers. Accordingly, Ab2 that had passed previous screening tests were screened further in immunization experiments. The objective is to identify the candidates that can elicit Ab3 sharing idiotypes with Ab1, and exhibiting a similar binding specificity for the tumor-associated antigen.

For each Ab2 to be tested, a minimum of 5 BALB/c mice and two New Zealand white rabbits were immunized. For immunization of mice, the Ab2 was conjugated to KLH. 50 μg was injected, and the mice were bled periodically to test the response. 500 μg was injected per rabbit, emulsified in complete Freund's adjuvant on day 0, in incomplete Freund's adjuvant on day 14, and in saline (i.m.) during the next 2 months. The rabbits were bled 14 days after the last injection.

Anti-CEA activity was measured by ELISA (see generally Engvall et al. (1972) *J. Immunol.* 109:129). Various dilutions of test sera were incubated in CEA coated wells, and antibody bound was detected with enzyme-linked anti-immunoglobulin appropriate for the species. This assay requires the antibody to bind the original tumor-associated antigen, and establishes that at least a portion of the Ab3 induced by immunizing with the anti-idiotype is tumor antigen specific. The level of CEA-specific Ab3 was titered by serial dilution, and defined the "quality" of the immunizing Ab2. Sera from mice and rabbits immunized with an unrelated monoclonal antibody (4EA2) was used as a negative specificity control.

The 3H1 monoclonal antibody emerged as having the highest quality amongst the candidates tested.

Figure 8:
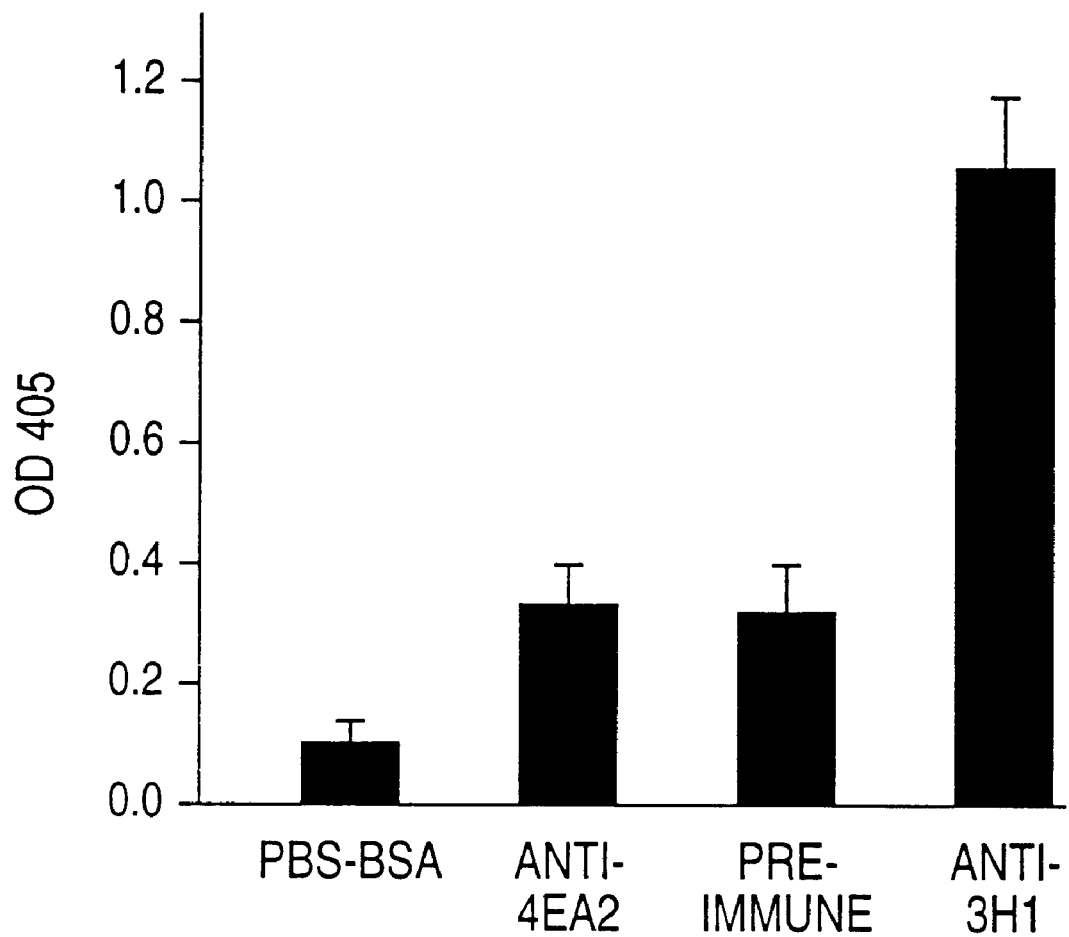
FIG. 8 is a bar graph depicting binding of sera from mice immunized with 3H1 to CEA. First bar, PBS-BSA; second bar, anti-4EA2; third bar, pre-immune sera; fourth bar, sera from mice immunized with 3H1. shows immunization with 3H1 induced antibodies that bound to insolubilized CEA.

As shown in FIG. 8, Ab3 present in the sera of mice immunized with 3H1 was specific for insolubilized CEA. All immunized mice (six in two groups) developed anti-CEA antibody as measured by ELISA. Control sera from preimmune mice or mice immunized with an unrelated Ab2-KLH (4EA2) did not show binding to pure CEA. In a parallel experiment, the binding of the same antisera was compared on a plate coated with unrelated ovarian tumor glycoprotein. The maximum binding obtained in each case was between 0.3 to 0.4 OD, the same as obtained with PBS-BSA control.

Figure 9A:
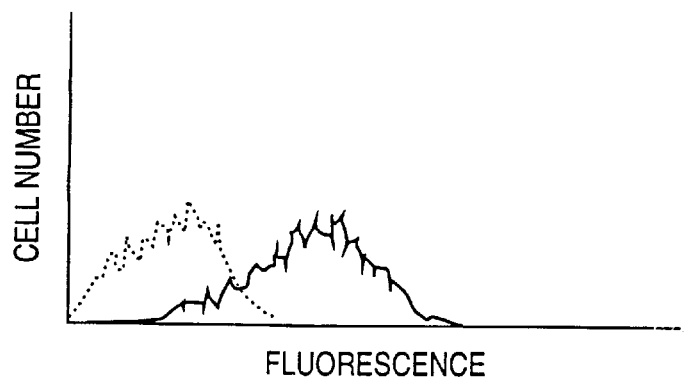
FIGS. 9A to 9D depict FACS analysis of LS174-T cells reacted with 80 19 (Ab 1) (FIG. 9A); sera from mice immunized with 3H1 (FIG. 9B); pre-immune sera (FIG. 9C) Sera from 3H1-immunized mice showed distinct binding (FIG. 9B) that was similar to the binding pattern obtained with 8019 (Ab1) (FIG. 9A). No significant binding was obtained with human B cell lymphoma cells which do not express CEA (FIG. 9D).
Figure 9B:
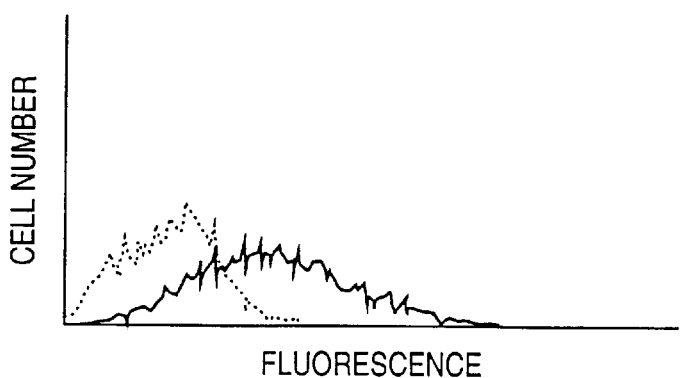
Figure 9C:
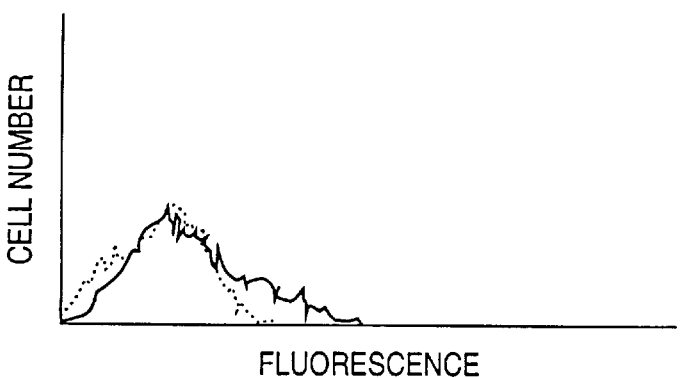
Figure 9D:
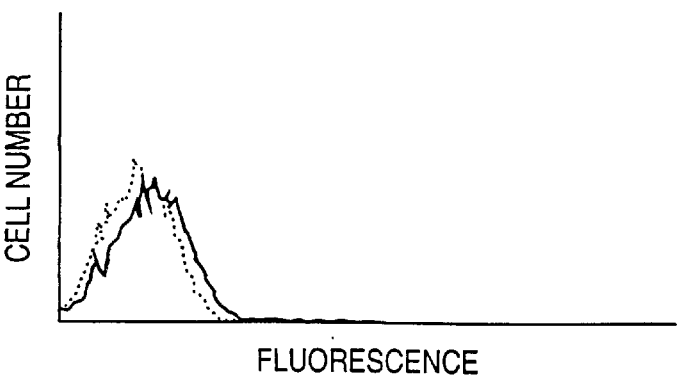

In a related experiment, the binding of Ab3 to cultured human colon carcinoma LS174-T cells were tested in an indirect immunofluorescence assay and flow cytometry. As shown in FIGS. 9A to 9D, Ab3 containing sera from 3H1-immunized mice showed distinct binding (B) that was similar to the binding pattern obtained with 8019 (Ab1) (A). No significant binding was obtained with human B cell lymphoma cells which do not express CEA (FIG. 9D). Confirmation that the Ab3 elicited by 3H1 had the desired specificity Since the therapeutic objective of 3H1 lies in its ability to elicit a response reactive against the tumor associated antigen, the specificity of the Ab3 obtained was confirmed in a number of subsequent experiments.

The rabbit and mouse Ab3 antisera were depleted of anti-isotype and anti-allotype activity for use in the specificity experiments by passing over an adsorbant made by coupling immunoglobulin fractions of BALB/c mouse serum coupled to 4B. Adsorption was repeated until no anti-isotype or anti-allotype activity could be detected by immunodiffusion. Adsorbed Ab3 containing sera were diluted with PBS containing 1% BSA, 0.05% Tween 20 and used in specificity determination without any further purification.

Spleen cells from mice immunized with 3H1 were used to generate monoclonal Ab3 producing cell lines, using similar hybridoma technology as described earlier.

Inhibition assays: To determine whether Ab3 sera compete with Ab1 for binding to human colon carcinoma cells, the binding of radioiodinated 8019 to confluent monolayers of LS174T cells was tested for inhibition in the presence of different Ab3 sera and Ab1.

For direct binding assay between Ab1 and 3H1, purified 3H1 was used to coat plates (155 ng/well), and the binding of radiolabeled 8019 to 3H1 was tested in the presence of different Ab3 and Ab 1. Percent inhibition of the assays were calculated according to the formula described above.

Sera from syngeneic mice immunized with 3H1, at $^1/_{10}$ dilution, inhibited binding or iodinated 3H1 (Ab2) to Ab1 by 90%. No inhibition by preimmune sera or sera from mice immunized with unrelated Ab2, 4EA2-KLH was observed. Although steric hindrance by Ab3 binding cannot be excluded in these assays, the results suggest the presence of Ab3 antibodies that share idiotopes with Ab1 (8019). The antisera from rabbits 729 and 730, immunized with 3H1, at $^1/_{10}$ dilution, inhibited binding or iodinated 8019 to Ab2 by 88 and 57%, respectively. No significant inhibition was obtained with preimmune rabbit sera.

Figure 10:
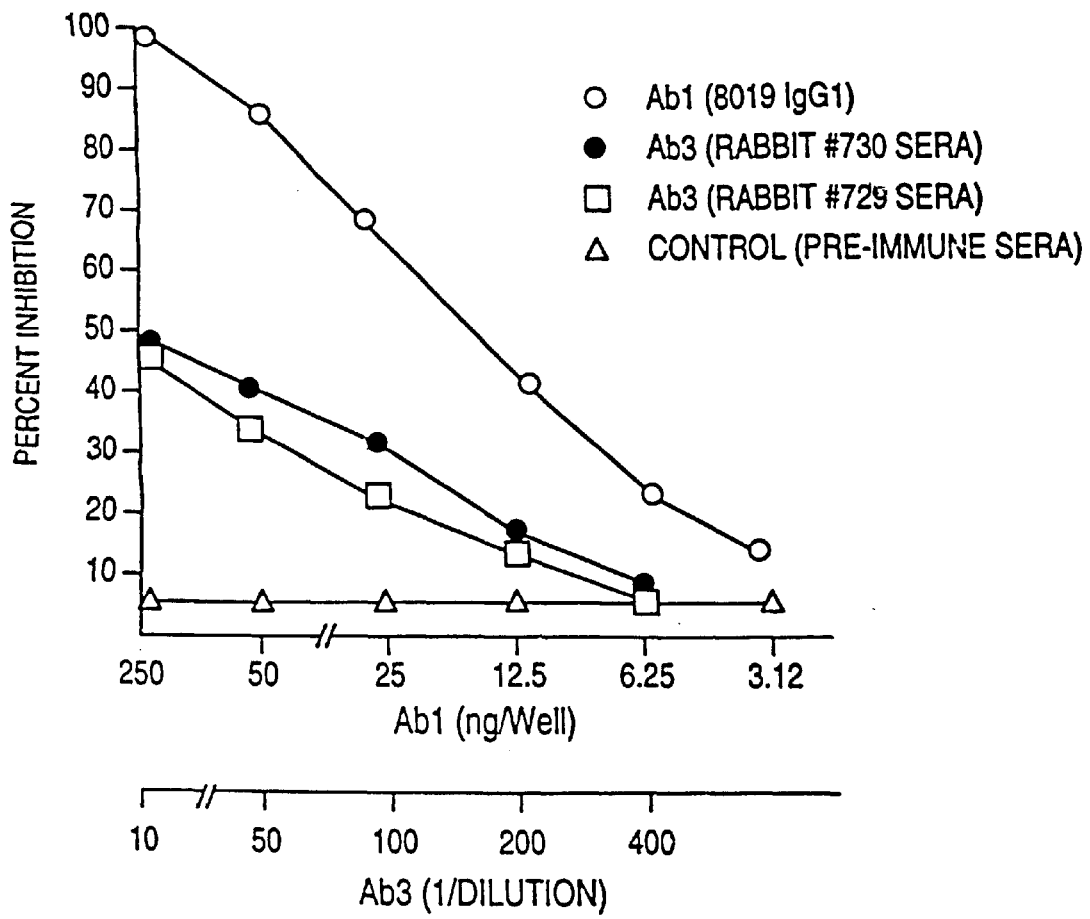
FIG. 10 is a graph depicting inhibition of 8019 binding to LS174-T cells by sera from rabbits immunized with 3H1. Open circles denote 8019 (Ab1); closed circles denote serum from rabbit #730; open squares denote serum from rabbit #729; open triangles denote pre-immune sera.

If Ab3 has a similar binding site as Ab 1, it should compete with Ab1 for binding to CEA as expressed by the human carcinoma cell line LS174-T. A fixed amount of radiolabeled 8019 was coincubated with different dilutions of rabbit Ab3 sera or Ab1 preparation and LS174-T cells (FIG. 10). Twenty ng of purified 8019-IgG1 (Ab1) inhibited binding by 50%, whereas the rabbit sera to $^1/_{10}$ dilution produced 47 and 49% inhibition respectively for rabbit 729 and 730. This indicated that polyclonal rabbit Ab3 sera bind to the same Ag as Ab1 and therefore contain some antibody molecules with Ab1 properties.

Western blot analysis: The semipurified CEA extract was separated by standards SDS-PAGE in 7.5% gel under non-reducing conditions without β-mercaptoethanol. After electrophoresis the gel was transblotted to nitrocellulose filters according to the procedures to Towbin et al. ((1979) *Proc. Natl. Acad. Sci. USA* 76:4350). The filter strips were blocked with PBS-1% BSA and then incubated separately with 8019, polyclonal rabbit Ab3 sera, control rabbit Ab3 sera against unrelated Ab2, as well as monoclonal Ab3 culture supernatant. After incubation, the filter strips were washed with PBS and incubated with goat anti-mouse Ig or goat anti-rabbit Ig-alkaline phosphatase labeled reagents. The filter strips were again washed and the reaction was developed with the reagents BCIP and NBT supplied for an immunoblot kit (Bio-Rad Laboratories, Richmond, Calif.).

Figure 11:
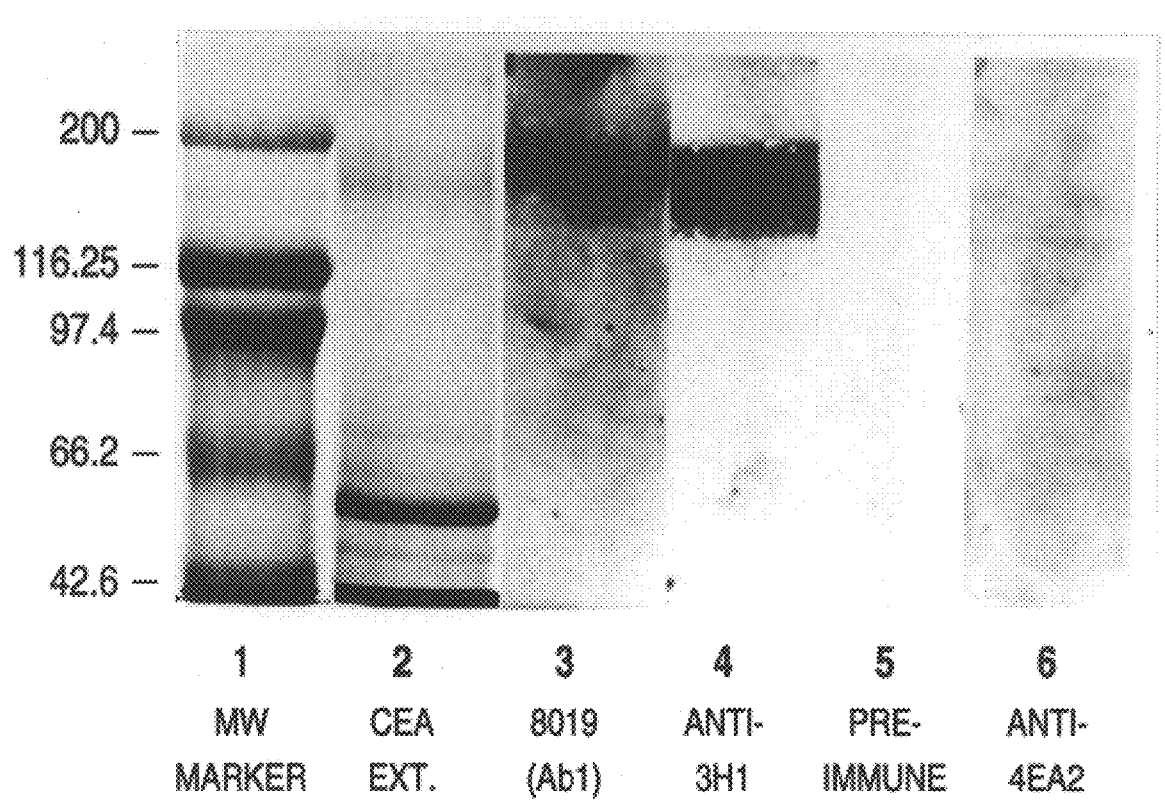
FIG. 11 is a half-tone reproduction of an immunoblot showing binding of Ab3 in rabbit sera to CEA. All reactions were with semi-purified extract of CEA separated by SDS-PAGE. Lane 1, molecular weight markers; lane 2, CEA extract stained with Buffalo black; lane 3, 8019; lane 4, rabbit sera (after immunization with 3H1); lane 5, pre-immune rabbit sera; lane 6, control sera from rabbits immunized with unrelated anti-Id 4EA2.

It has been shown that mAb 8019 specifically immunoprecipitates the 180,000 m.w. CEA by SDS-PAGE analysis (Mitchell (1980) *Cancer Immunol. Immunother.* 10:1). To confirm that the Ab3 induced by 3H1 was specific for the CEA molecule, semipurified extract of CEA was separated by SDS-PAGE and transblotted to nitrocellulose filters. One filter strip (FIG. 11, lane 2) was stained with buffalo black. There were two overlapping bands at the 180,000 m.w. region (CEA) and one major band at the 50,000 m.w. region (normal cross-reacting Ag) and a few minor low m.w. bands. The remaining filter strips were then incubated with mAb 8019, rabbit Ab3 sera, and rabbit sera immunized with the unrelated isotype-matched Ab2β 4EA2 (a negative control). The reaction was developed by the ELISA assay as described above. Antibody 8019 (FIG. 11, lane 3) and rabbit Ab3 (lane 4) immunoprecipitated only molecules with a molecular mass of 180,000 Da from this complex mixture. The materials that were not precipitated by mAb 8019 or rabbit Ab3 sera contained a wide range of lower m.w. CEA-related Ag. There was no reactivity with preimmune (FIG. 11, lane 5) or control sera (lane 6). The Western blotting analysis confirmed the specificity of mAB 8019 and the reactivity of rabbit Ab3 with 180,000 m.w. CEA.

Figure 12:
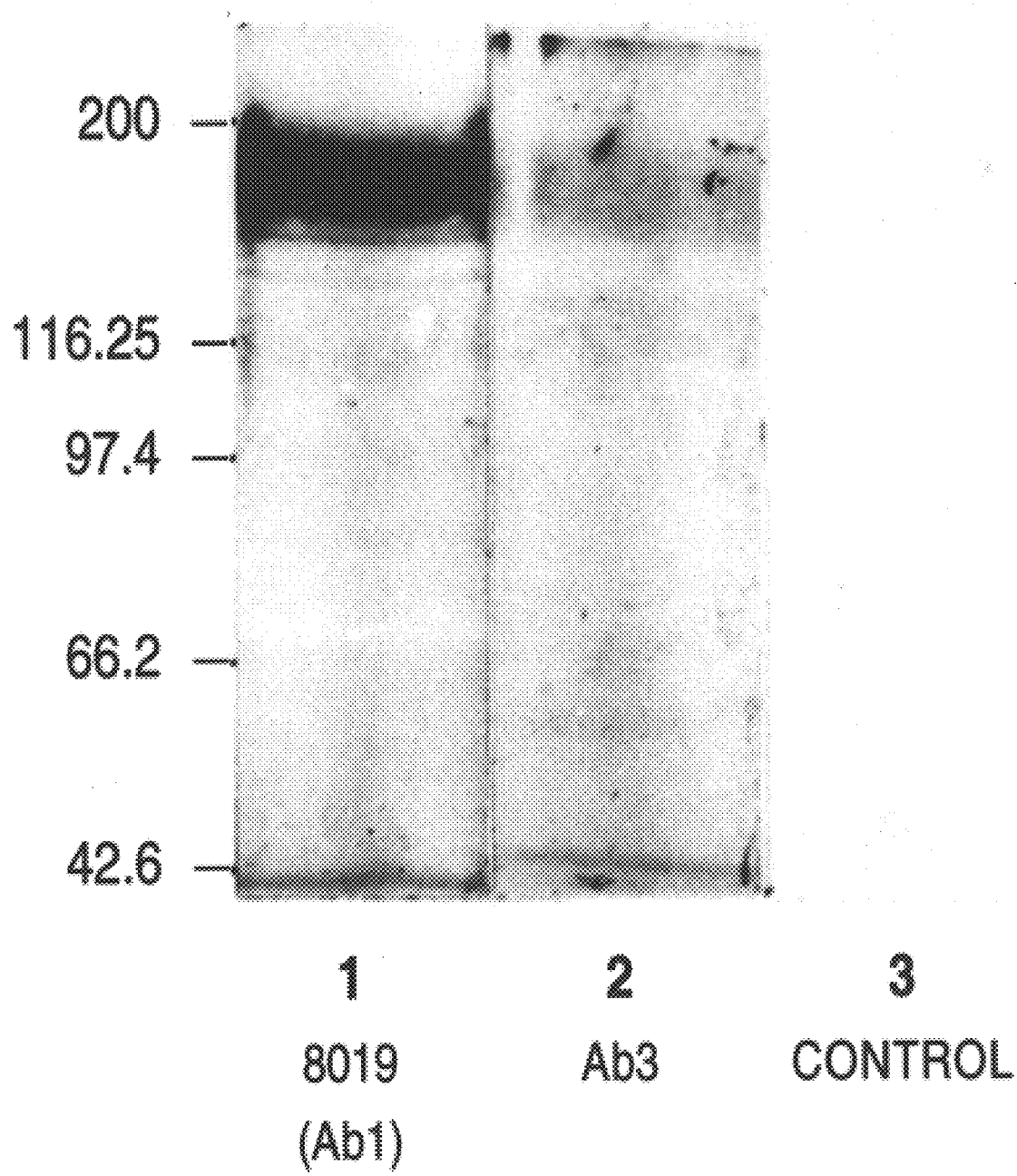
FIG. 12 is a half-tone reproduction of an immunoblot showing binding of Ab3 in mouse sera to CEA. Lane 1, 8019 (Ab1); lane 2, monoclonal mouse Ab3; lane 3, control.

FIG. 12 is a similar experiment conducted with mouse sera. The Ab3 elicited in mice immunized with 3H1 identified the same 180,000 m.w. form of CEA in the Western blot.

Immunoperoxidase staining of tissue sections with Ab1 and Ab3. The reactivities of monoclonal Ab1 and Ab3 (both polyclonal and monoclonal) were compared on surgical specimens of normal colon and colonic adenocarcinomas by a very sensitive staining method (biotin-streptavidin reagents, Vector, Burlingame, Calif.) as described in detail by Viale et al. ((1989) *J. Immunol.* 143:4338). All sections were counterstained with Meyer's hematoxylin. Pertinent specificity tests were performed, including block of the endogenous peroxidase, omission of the first layer, or substitution of nonimmune homologous serum for the specific antiserum and P3-653 myeloma culture supernatant for the Ab3 culture supernatant.

Figure 13:
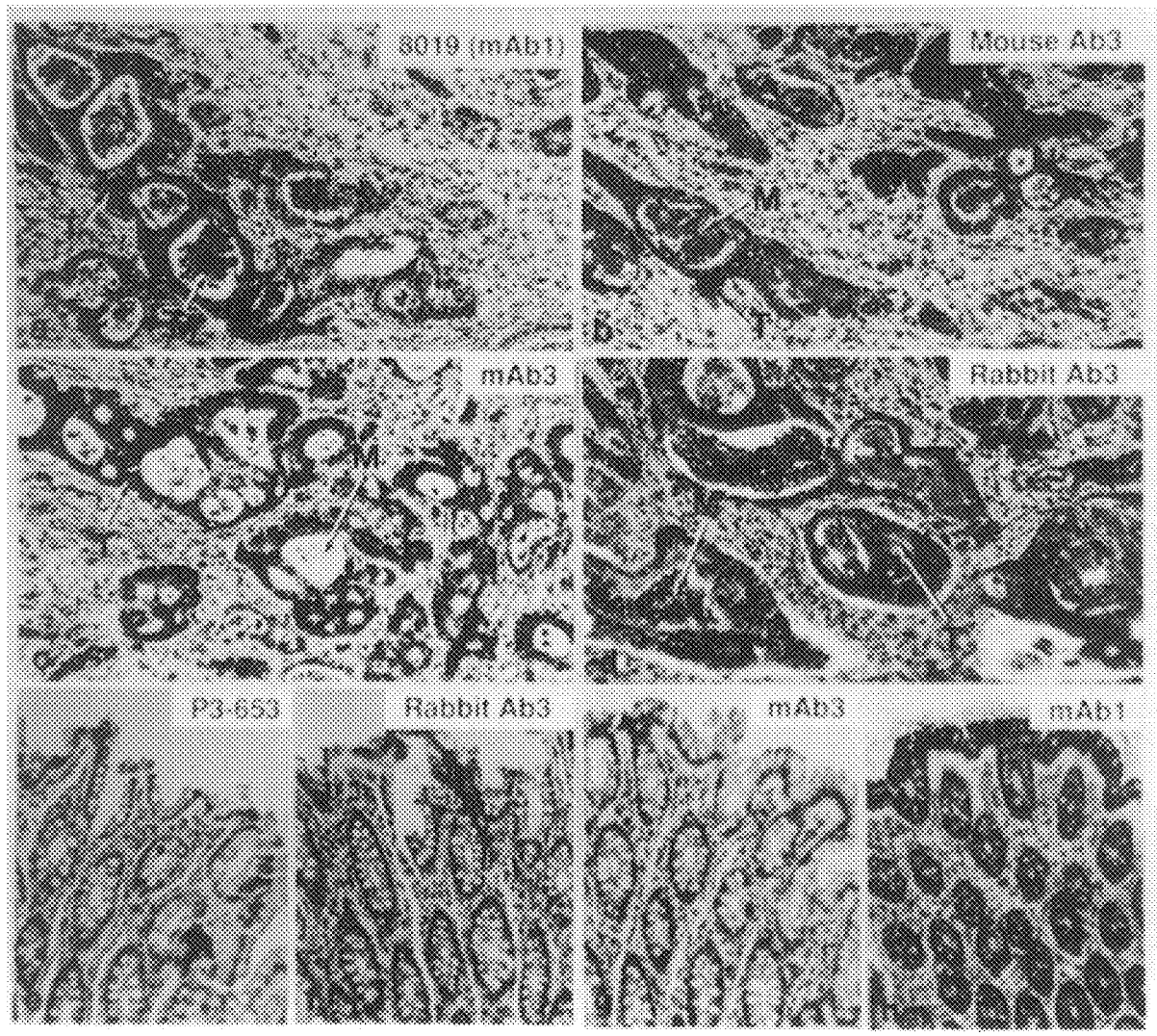
FIG. 13 is a half-tone reproduction depicting an immunostained (immunoperoxidase) normal and cancerous tissue sections with Ab3. The pattern of reactivity of Ab3 on both normal and malignant colonic tissues was almost identical to that obtained with Ab1.
Figure 14:
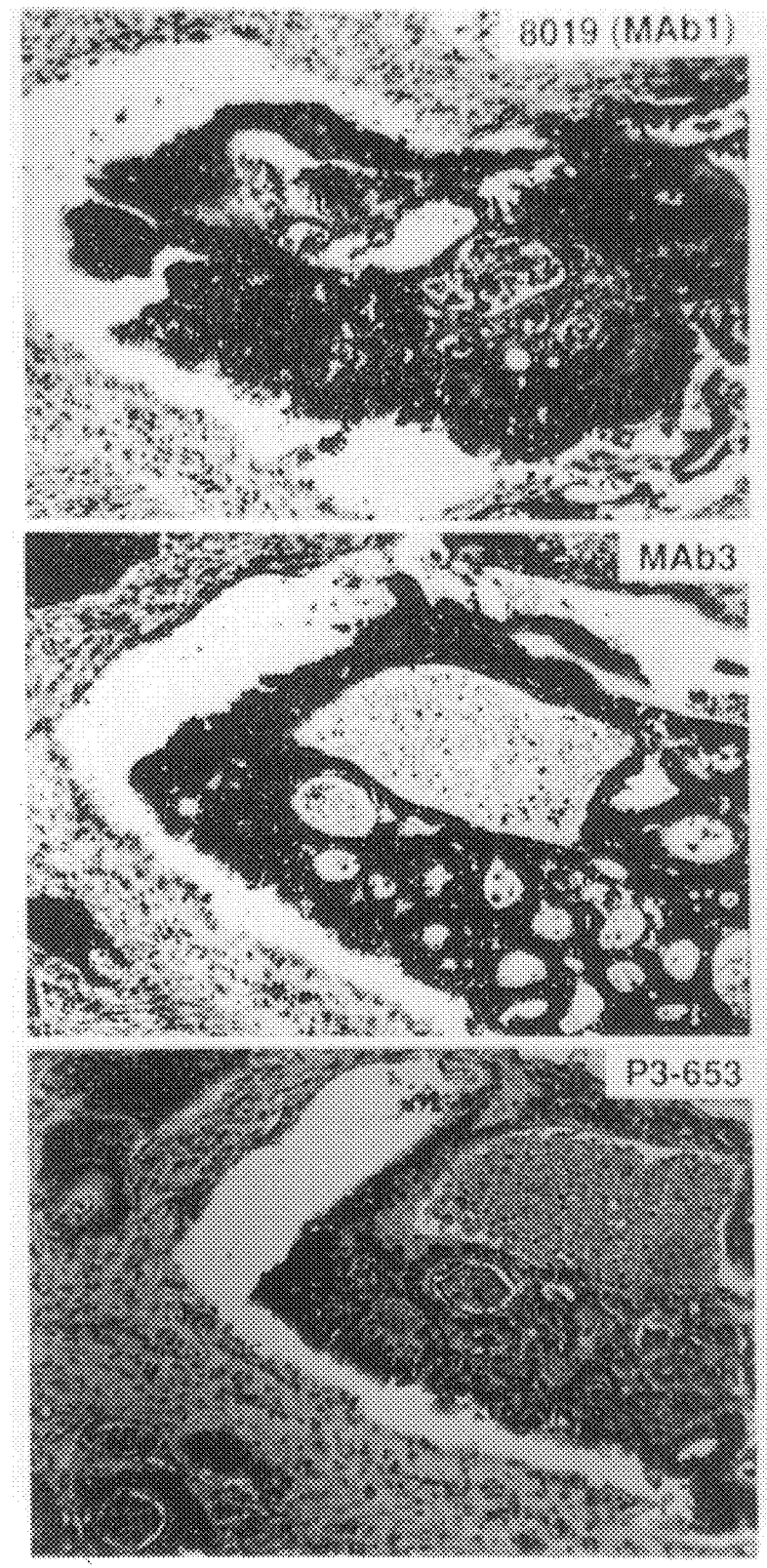
FIG. 14 is a half-tone reproduction depicting immunostained (immunoperoxidase) normal and cancerous tissue sections with Ab3. Reaction with 8019 (Ab1) resulted in the staining of tumor cells as well as secreted mucinous materials whereas reaction with mAb Ab3 resulted in the staining of tumor cells with no staining of secreted mucin.

The reactivity of 8019 were compared with that of Ab3 (both polyclonal and monoclonal) on normal colon and colonic tumor specimens. The pattern of reactivity of Ab3 on both normal and malignant colonic tissues was almost identical to that obtained with Ab1 (FIG. 13). There was no reaction with normal colonic mucosa, but 8019 and all the Ab3 reacted intensely with colonic tumors. The staining was apical in gland-like structures and granular (cytoplasmic) in less differentiated areas. There were subtle differences between the staining patterns obtained with 8019 (an IgG1, κ) and the monoclonal Ab3 (an IgM, κ). Reaction with 8019 resulted in the staining of tumor cells as well as secreted mucinous materials, whereas reaction with monoclonal Ab3 resulted in the staining of tumor cells with no staining of secreted mucin. (FIG. 14).

Tests of cellular immunity: Additional experiments may also be conducted to demonstrate that the animals immunized with 3H1 also have a CEA-directed cellular immune response. Spleen cells from mice immunized with 3H1 may be used in a T-cell proliferation assay. The spleen cells are cultured for 5 days in the presence of semipurified CEA, and then pulsed with [$^3$H]thymidine. Greater uptake in cells from 3H1 immunized animals than with controls is consistent with the presence of an idiotype-specific cellular immune response. Immunized rabbits may also be tested for DTI I skin reactions against semipurified preparations of CEA or purified CEA. T cell cytotoxicity assays may also be conducted, as described elsewhere in this disclosure.

Figure 15:
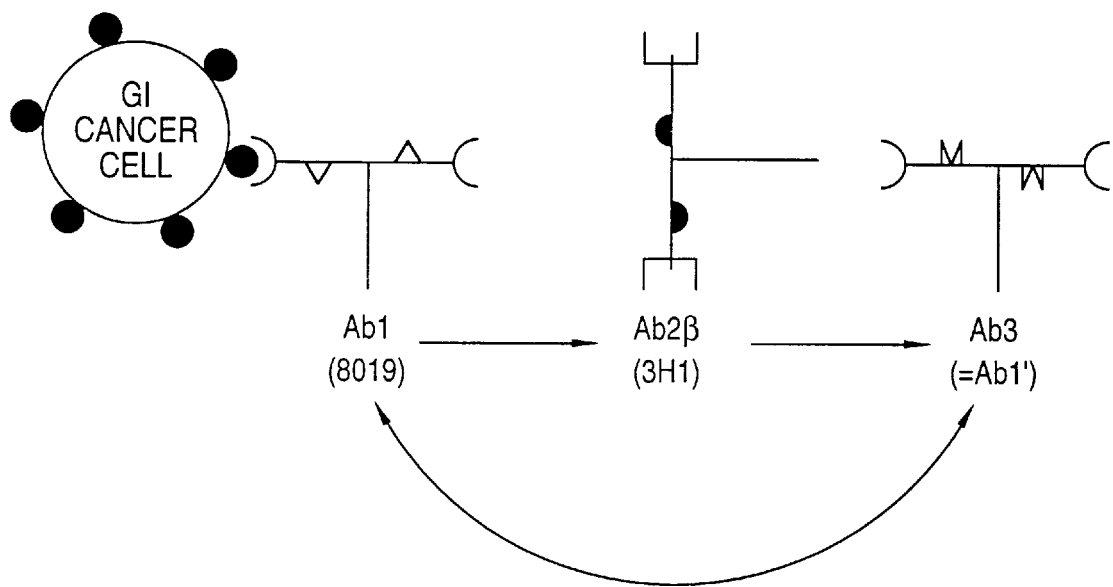
FIG. 15 shows a schematic of the idiotype network for human gastrointestinal carcinoma.

A schematic showing an anti-idiotype network based on 3H1 is shown in FIG. 15.

Example 2

Cloning and Sequencing of 3H1 cDNA

Unless otherwise specified, all cloning techniques were essentially as described by Sambrook et al. (1989) and all reagents were used according to the manufacturer's directions.

cDNA cloning and sequence determination of the variable regions of 3H1

To sequence the $V_H$ region, total RNA was isolated from 1×10$^7$ 3H1 hybridoma cells. Yield of total RNA was about 100 μg,. mRNA was prepared by passage through two-cycles of chromatography of oligothymidylate-cellulose columns. The yield of mRNA was about 10 μg. First strand cDNA was synthesized using SuperScript Preamplification kit (GIBCO/BRL). The DNA fragment encoding the $V_H$, of 3H1 was then amplified by PCR using the 5'-primer GGGAATTCATGRAATGSASCTGGGTYWTYCTCTT (SEQ ID NO:9) and the 3'-primer CCCAAGCTTC-CAGGGRCCARKGGATARACIGRTGG (SEQ ID NO:10) (I=inosine, R=A or G, Y=C or T, K=G or T, S=C or G, W=A or T) corresponding to sequences of the leader (signal peptide) region amino acids −20 to −13, and the gamma constant region amino acids 126 to 119. In addition, the 5'-III site provided an alternative cloning strategy (Novagen, Madison Wis.). The fragment of cDNA amplified was subcloned into pT7 plasmid and NovaBlue competent cells were transformed using a protocol provided by the supplier (Novagen). Recombinant colonies were picked up by color selection and plasmid DNA was prepared. The DNA sequence of the double stranded plasmid was determined by Sequenase Version 2.0 kit (USB, Cleveland, Ohio). The sequence of the DNA insert in the plasmid was determined from both orientations using T7 promoter primer (TAATACGACTCACTATAGGG) (SEQ ID NO:11) and U-19 primer (CTTTTCCCAGTCACGACGT (SEQ ID NO:12)). At least 8 clones were picked for sequence determination. The sequence of the 3H1 light chain was similarly determined. The forward primer for the light chain was 5'-ACTAGTCGACATGGTRTCCWCASCTCAGTTCCTTG (SEQ ID NO:13) and the reverse primer was 5'-CCCAAGCTTACTGGATGGTGGGAAGATGGA (SEQ ID NO:14), corresponding to −20 to −12 amino acids of the leader sequence and 122 to 116 of the constant region of the mouse kappa chain.

In order to minimize the error rates in PCR amplification, pfu DNA polymerase (Stratagene, San Diego) was used for amplification in all subsequent experiments. Mutant frequency with this thermostable DNA polymerase is 1/10 compared to Taq DNA polymerase.

Verification of the cDNA clone by amino acid sequence

Although 3 clones that we picked all had the same sequence, we felt it necessary to confirm that the isolated cDNA was indeed that of 3H1. Fifty μg of purified 3H1 antibody was diluted with sample loading buffer (50 mM Tris-HCl, pH 6.8, 1% SDS, 1% glycerol, 0.1% β-mercaptoethanol) and heated to 100° C. for 3 minutes. The denatured protein was loaded onto a 7.5% polyacrylamide gel (BioRad Miniprotean II Dual Slab Cell) containing SDS and subjected to electrophoresis at 200 V for 1 hour. Proteins in the gels were transferred to polyvinylidene difluoride (PVDF) membranes by the procedure described by Twobin et al. ((1979) *Proc. Natl. Acad. Sci. USA*. 78: 4350–4354) at 150 mA overnight. The transfer buffer contained 25 mM Tris, 192 mM glycine, 20% (v/v) methanol. The membranes were stained by quick dipping in 0.1% Coomassie Brilliant blue in 50% methanol-50% acetic acid, followed by washing in a solution containing 40% methanol plus 10% acetic acid. After drying the membrane at room temperature, the stained heavy and light chain bands were excised with a clean razor blade. The proteins on the membrane slices were subjected to N-terminal microsequencing by automated Edman degradation using an Applied Biosystem Model 477A protein sequencer employing pulsed-liquid chemistry and on-line phenyl-ethiohydantion amino acid identification. Each protein was subjected to 10–15 degradative cycles and the converted cleavage products from each cycle were analyzed by reverse-phase HPLC. The sequencing was done by Macromolecular Structural Facility of the University of Kentucky. The sequence of the peptide was (Glu) ValGln-LeuGlnGlnSerGlyProGluLeuValLysProGly (SEQ ID NO:15). Except for the first Glu whose identity was uncertain, 14 amino acid residues of the peptide matched exactly with the amino acids 2–15 of 3H1 heavy chain. This confirmed that the cDNA clone picked was that of the 3H1 heavy chain.

cDNA (SEQ ID NO:1) and derived amino acid sequence (SEQ ID NO:2) of the light chain variable region of 3H1 are shown in FIGS. 1A and 1B. cDNA (SEQ ID NO:3) cDNA and derived amino acid sequence (SEQ ID NO:4) of the heavy chain variable region of 3H1 is shown in FIGS. 2A and 2B.

Example 3

Analysis of Immune Response Elicited by 3H1 in Non-Human Primates

Cell Lines

The human colon carcinoma cell line LS174-T, which expresses CEA at high density, was grown in RPMI 1640 medium supplemented with 10% fetal calf serum, 1% L-glutamine and penicillin and streptomycin and used for the detection of anti-tumor responses. The human melanoma cell line M21/P6 (kindly provided by Dr. Ralph Reisfeld, Scripps Research Institute, La Jolla, Calif.), and the T-cell line MOLT-4, both of which are CEA negative, were grown in the same medium and were used as negative controls.

Antibodies

3H1 was obtained as described in Example 1. The mAb2, 11D10 (IgG1, κ) is a murine anti-Id mAb which mimics the human milk fat globule (CEA) (Mukerjee et al. (1992) *FASEB J.* 6:A2059) and was used as a control.

Preparation of 3H1 for Immunization

We immunized monkeys with 3H1 precipitated with alum prepared as follows. Herlyn et al. (1987) *PNAS* 84:8055–8059.

To 5 mg aliquots of purified mAb anti-Id (3H1), 1 ml of 2% Alu-Gel S (Serva Fine Biochem, Inc., Garden City, Long Island, N.Y.) was added. The volume was then adjusted to 10.0 ml with D-PBS and the mixture incubated on a vortex for one hour at room temperature. The mixture was then centrifuged at 2000 rpm at 24° C. for 10 minutes. The amount of mAb bound in the gel layer was determined by measuring spectrophotometrically the amount of unbound antibody in the supernatant. The Alu-Gel precipitated antibody was stored at 4° C. until use. These procedures were performed aseptically in a laminar flow hood and the final product was sterile and clearly labeled as anti-Id 3H1 Alu-Gel and aliquoted into pyrogen-free, sterile glass vials.

Immunization of Monkeys

Cynomolgus monkeys were immunized with alum precipitated anti-Id 3H1 as well as with control alum precipitated anti-Id 11D10 (specific for CEA). Monkeys were housed at the White Sands Research Institutes, Alamogordo, N.M. A pair of male and female monkeys, weighing 3–4 kg, was immunized with either 2 mg of 3H1 or 11D10 intracutaneously at four different sites on day 0, 14, 28 and 42 respectively. Only two monkeys were used for each anti-Id (Ab2) at a single dose for financial reasons. The 2 mg dose was selected based on previous pre-clinical (Chattopadhyaya et al. (1992) *PNAS* 89:2684–2688) and clinical studies (Herlyn et al. (1987) *PNAS* 84:8055–8059; Mittelman et al. (1992) *PNAS* 89:466–470) with different anti-Id vaccines. Blood samples were collected before immunization and 10 days after each immunization.

Toxicity

The induction of Ab3 responses in monkeys did not cause any apparent side effects in animals. Only mild local swelling and irritation were observed at the injection site as a result of multiple immunizations. The monkeys were routinely checked by physical examinations and weight measurements.

Purification of anti-anti-Id antibody (Ab3) from hyperimmunized monkey sera

Twenty milliliters of hyperimmune serum were passed over an immunoabsorbent column consisting of immunizing anti-Id immunoglobulin (3H1-IgG1) coupled to Sepharose 4B. Anti-anti-Id antibodies (Ab3) were eluted with 0.1 M glycine-hydrochloric acid buffer (pH 2.4) and neutralized to pH 7.0 with 3M Tris. The eluted antibody was then passed over an immunoabsorbent column consisting of isotype-allotype matched murine immunoglobulin coupled to Sepharose 4B to remove anti-isotype and anti-allotypic reactivities. Antibody that passed through was concentrated and used as purified Ab3. The isotype of Ab3 was determined by ELISA using human anti-isotype specific reagents (Tago Inc., Burlingame, Calif.).

Development of Humoral Immunity Induced by Immunization with Alum-Precipitated 3H1

(a) Specific Ab3 response to 3H1

Sera obtained from immunized monkeys 10 days after the fourth immunization were tested for the presence of anti-anti-Id antibodies (Ab3). For these assays, the sera were pre-treated with normal mouse immunoglobulin (500 μg/ml) to block anti-isotypic and anti-allotypic reactivities and then checked for the presence of (Ab3) by reaction with the immunizing anti-Id (3H1) coated onto microtiter plates, by radioimmunoassay (RIA). Ab3 at a 1:40 dilution was incubated with anti-Id MAb 3H1 or 11D10, coated on the microtiter plate and then reacted with $^{125}$I-labeled 3H1 or 11D10 (50,000 cpm) in a sandwich assay. The results are expressed as bound cpm in a sandwich assay (A). The results are presented as mean cpm (n=3). The SD of the data was <10%. For the binding inhibition assay between Ab2 and Ab1, purified Ab1 8019 was used to coat the plate (250 ng/well) and the binding of radiolabeled Ab2 to Ab1 was tested in the presence of different dilutions of Ab3 sera. The sera were preincubated with normal mouse IgG prior to the assay. The results are expressed as percent inhibition at a dilution of 1:40. Unrelated Ab2 11D10 was used as the control. After washing, the anti-antibody reaction was tagged using $^{125}$I-labeled anti-Id reagent in a homogeneous sandwich RIA. Pre-immune sera and sera from monkeys immunized with control Ab2, 11D10 were also used in these assays. In addition, $^{125}$I labeled monoclonal Ab2 11D10 was used as control. The results are shown in Table 1.

TABLE 1

Analysis of Monkey Anti-Anti-Id Sera Generated With Anti-ID mAb 3H1

| Assay | Plate Coated With | $^{125}$I Labeled Anti-ID | Sample Ab3 Sera | | Pre-Immune Sera | Ab3 Sera (Control) | |
|---|---|---|---|---|---|---|---|
| | | | PRO 541 | PRO 667 | | PRO 723 | PRO 872 |
| A. Sandwich RIA | 3H1 (Ab2) | 3H1 | 16,381 | 20,143 | 309 | 926 | 511 |
| | 11D10 (Unrelated Ab2) | 3H1 | 382 | 410 | 349 | 1,074 | 978 |
| | 3H1 (Ab2) | 11D10 | 887 | 1,049 | 167 | 301 | 532 |
| B. Inhibition | 8019 (Ab1) | 3H1 | 88 | 84 | 3 | <10 | <10 |

Serial dilutions of Ab3 sera from monkeys (PRO 541 and PRO 667) immunized with 3H1 bound specifically to the immunizing Ab2, 3H1, with minimal reactivity with unrelated Ab2, 11D10. Monkey Ab3 sera also inhibited the binding of radiolabeled Ab2 to Ab1 over 80% even at a dilution of 1:40 (Table 1). There was no inhibition with pre-immune sera or sera obtained from monkeys (PRO 723 and PRO 872) immunized with the unrelated Ab2, 11D10.

Figure 16:
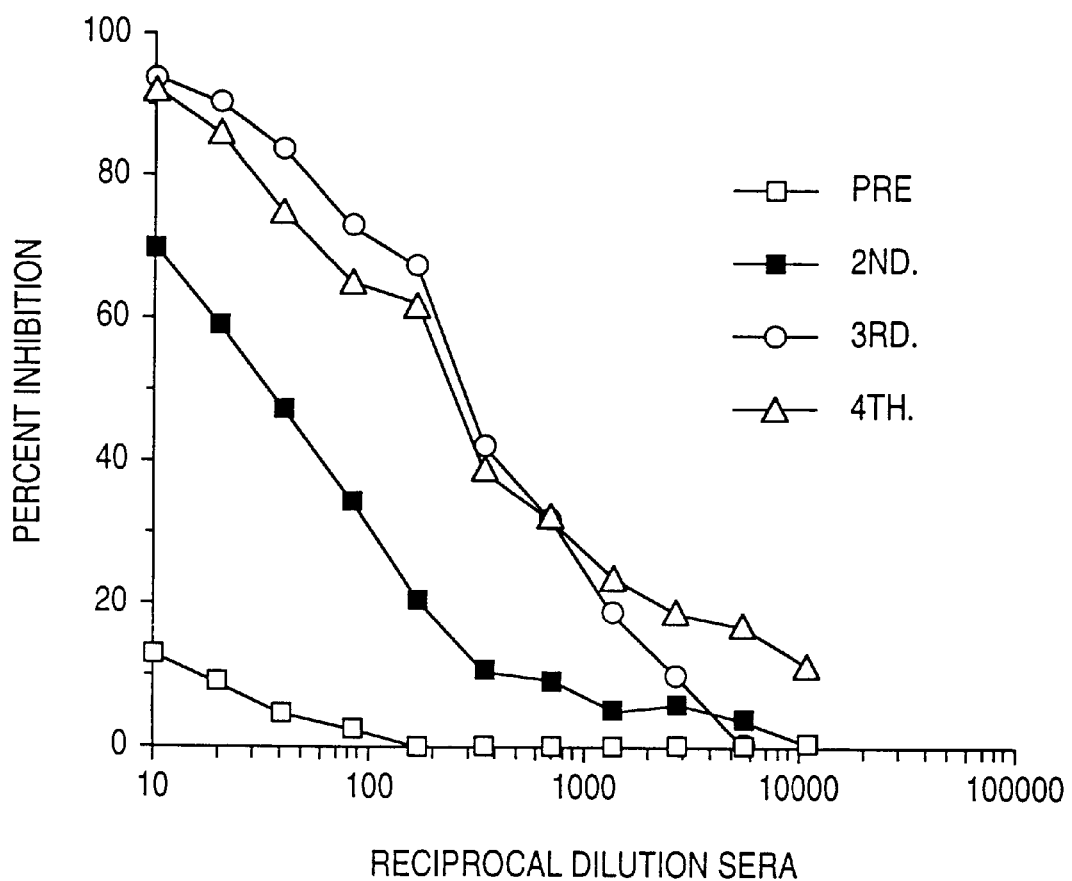
FIG. 16 is a graph depicting the inhibition of 3H1 binding to Ab1 (8019) by monkey (PRO 667) Ab3 sera by radioimmunoassay (RIA). Open squares denote preimmunization serum; solid squares denote serum after the second injection; open circles denote serum after the third injection; open triangles denote serum after the fourth injection.

The kinetics of the Ab3 response are shown in FIG. 16 using sera from monkey PRO 667 demonstrating inhibition of the binding of radiolabeled Ab2 to Ab1. Similar reactivity was seen with sera from monkey PRO 541. These results indicate that monkey Ab3 sera share idiotypes with the Ab1 (8019).

(b) Idiotope analysis of Ab3

If a positive reaction was obtained in (a) above, Ab3 sera from those monkeys were checked for their ability to inhibit the binding of $^{125}$I-labeled 3H1 to 8019 (Ab1) bound to microtiter plates or vice versa (inhibition of the binding of radiolabeled 8019 to 3H1 on the plate). An unrelated Ab1–Ab2 system (BrE1-11D10) was used as control (Mukerjee et al. (1992) FASEB J. 6:A2059). For this experiment, purified 8019 (Ab1) was used to coat the plate (250 ng/well) and the binding of radiolabeled 3H1 (~50,000 cpm) to 8019 was tested for inhibition in the presence of different dilutions of Ab3 sera. In a parallel control experiment, an unrelated Ab1–Ab2 system (mAb BrE1-11D10) was used as a control.

This demonstrated that Ab3 in monkey sera share idiotopes with 8019 (Ab1). This inhibition assay of Ab1–Ab2 binding by Ab3 sera also demonstrated that Ab3 is a true anti-anti-Id.

(c) Induction of Anti-CEA Antibody Response

Microtiter plates were coated with pure CEA (Rougier Biotech, Montreal, Canada) and reacted with the Ab3 sera, obtained after the fourth immunization at different dilutions by ELISA. A 96-well microtiter plate was coated with 100 $\mu$l of the purified preparation of CEA (2 $\mu$g of protein per ml) per well and incubated overnight at 4° C. The solution was removed from the plate by suction, and the plate was blocked with 1% BSA in PBS to saturate protein-binding sites. After incubation for 1 hour at room temperature, the solution was removed, and the wells were washed three times with PBS. Samples of diluted serum (50 $\mu$l), mixed with 50 $\mu$l of 0.05% Tween 20/1% BSA in PBS, were added in duplicate and incubated overnight at 4° C. After washing the plate, 0.1 ml of enzyme-labeled antibodies diluted 1/1000 in 0.05% Tween 20/1% BSA in PBS was then added and incubated at room temperature for 4 hours. The plates were again washed and developed with 0.1 ml of phosphatase substrate dissolved in diethanolamine buffer (50 mg of substrate per 50 ml of buffer). The absorbance at 405 nm was read on an ELISA Reader. The sensitivity of the assay was greater than 0.1 ng of antibody detected per well. Pre-immune sera and sera obtained from monkeys immunized with unrelated Ab2 11D10 were used as a control. The unrelated antigen HMFG was also used as a control in this assay.

Figure 17:
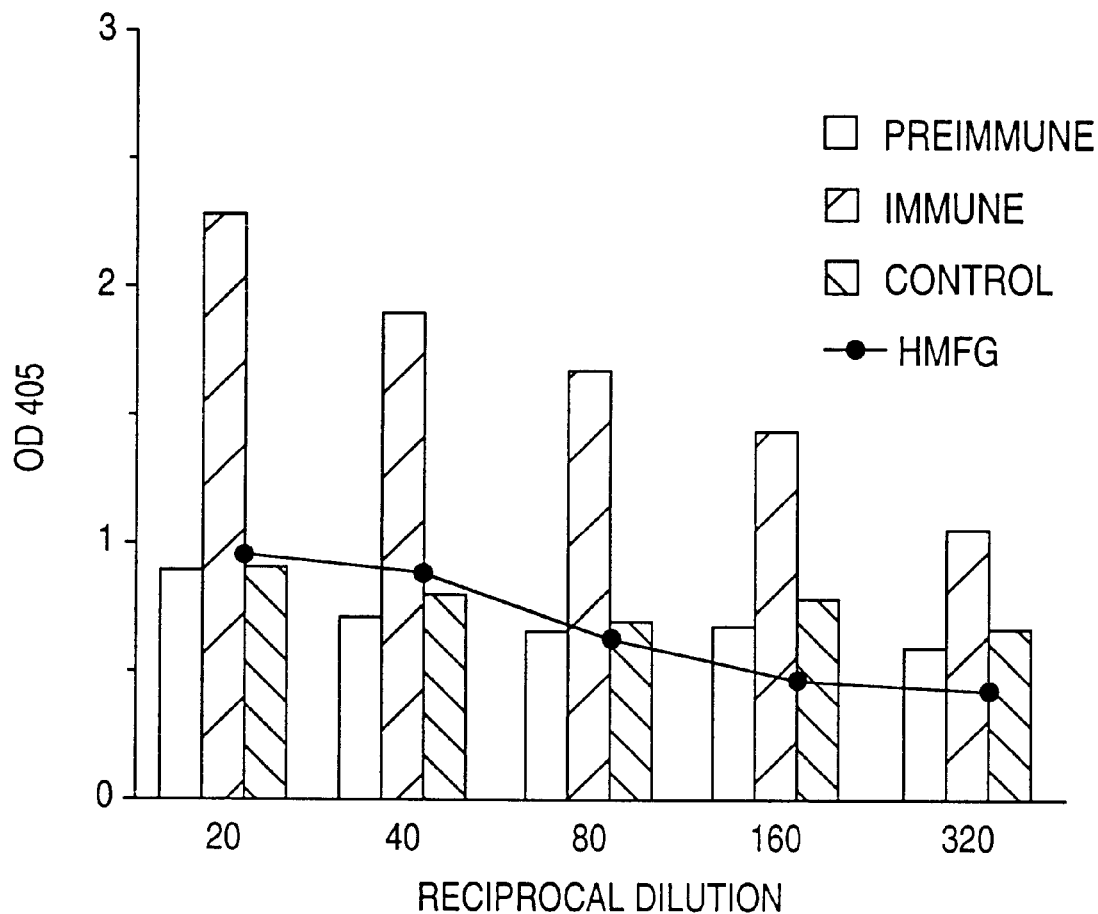
FIG. 17 is a bar graph depicting binding of monkey Ab3 sera to purified CEA by ELISA. Open bars denote preimmune sera; diagonally hatched bars denote immune sera; horizontally hatched bars denote control sera. The solid circles connected by a solid line denote unrelated antigen CEA.
Figure 18:
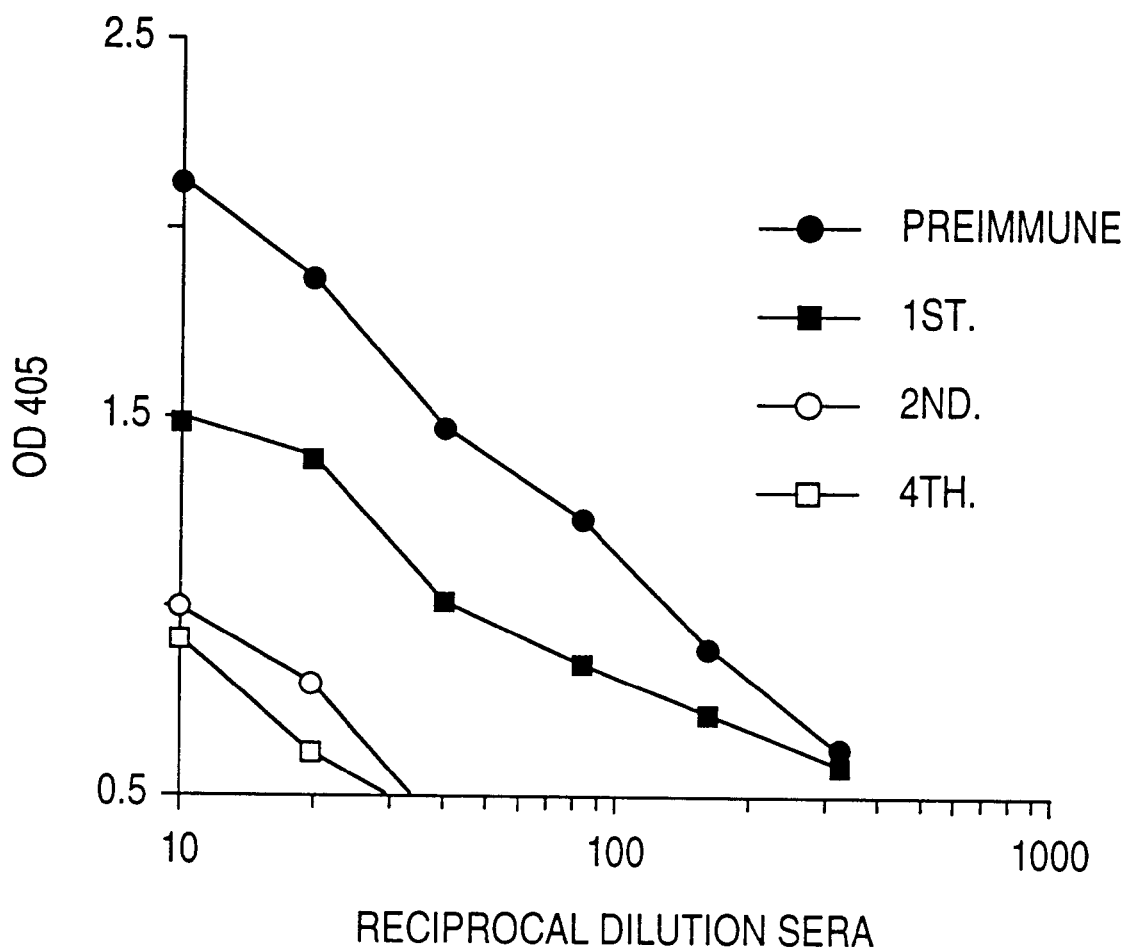
FIG. 18 is a graph depicting the kinetics of the binding of monkey Ab3 sera (PRO 667) to purified CEA by ELISA. Open squares with a center dot denote preimmune serum; open circles denote serum after the first injection; crosses denote serum after the second injection; open squares denote serum after the fourth injection.

The Ab3 sera from monkey PRO 541 bound specifically to purified HMFG (FIG. 17), while control sera from pre-immune monkeys or monkeys immunized with unrelated Ab2, 11D10, did not show appreciable binding to CEA. In parallel experiments, the same Ab3 from monkey PRO 541 was compared on a plate coated with control HMFG antigen and were negative. The kinetics of the anti-CLA response from monkey PRO 667 are shown in FIG. 18.

To determine the reactivity with cell-surface CEA, LS174-T cells were tested by immune flow cytometry. CEA positive LS174-T cells (1×10$^6$ per well) were reacted with Ab1(8019) and Ab3 at 100 $\mu$l at 4° C. for 60 minutes. After washing, the cells were incubated with either goat anti-mouse or goat anti-human F(ab')$_2$ IgG-FITC labeled antibody (Tago Inc., Burlingame, Calif.) for 30 minutes at 4° C. They were then washed twice, fixed in 2 percent paraformaldehyde, and analyzed by immune flow cytometry (FACS STAR, Becton Dickinson, San Jose, Calif.). Antigen negative MOLT-4 cells and melanoma cells M21/P6 (not shown) were used as controls in this assay.

Figure 19A:
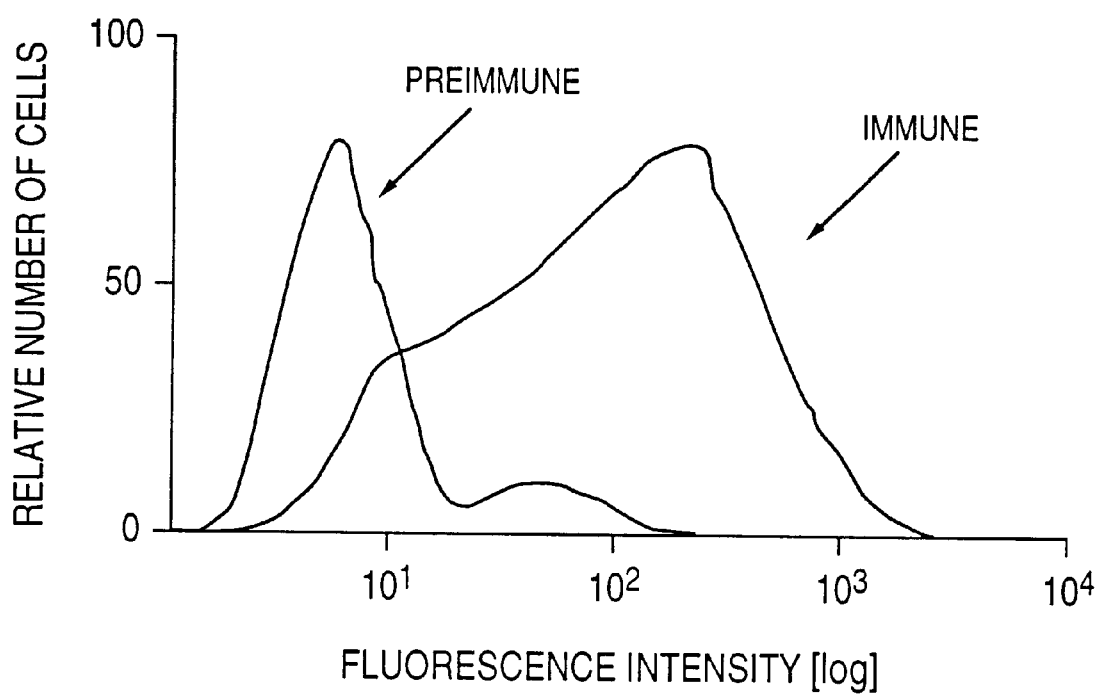
FIGS. 19A and 19B are graphs depicting immune flow cytometry analysis of LS174-T cells with monkey Ab3 sera.
Figure 19B:
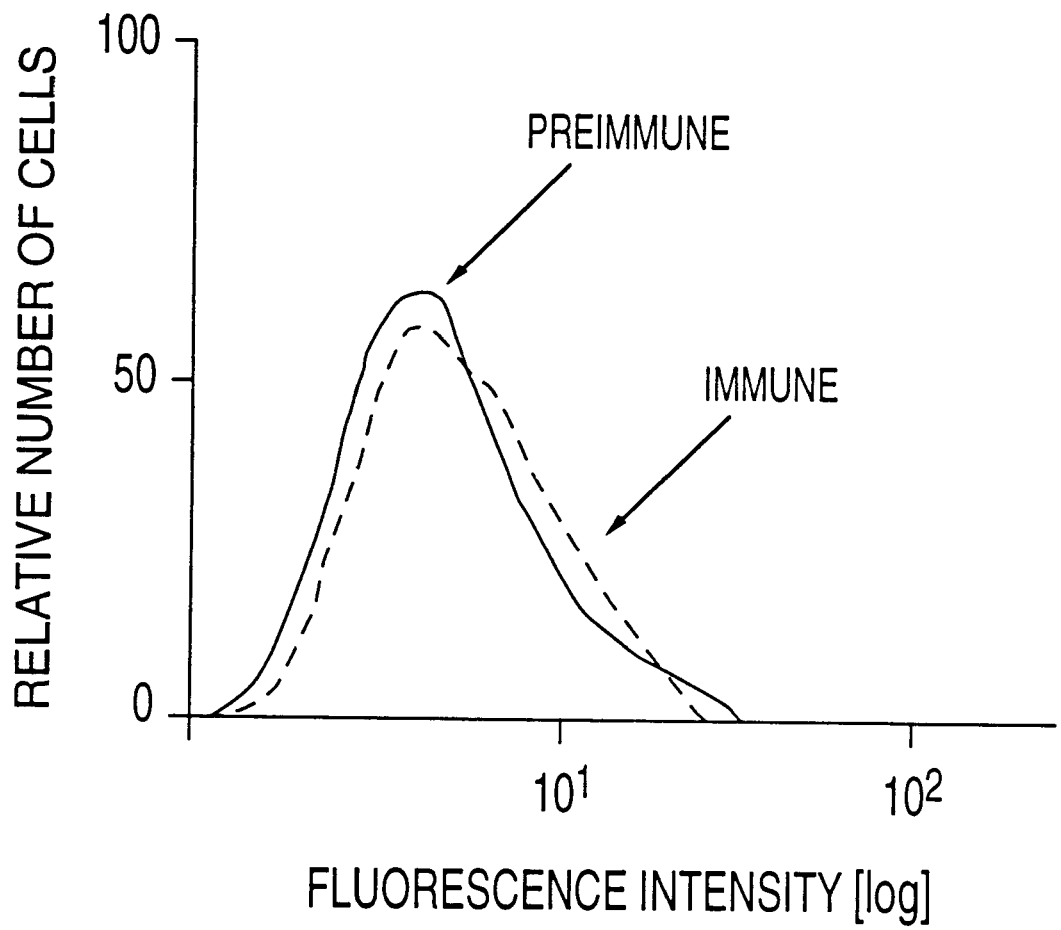

As shown in FIGS. 19A and 19B, Ab3 from 3H1 immunized monkeys showed distinct binding (FIG. 19A) that was similar to the binding pattern obtained with Ab1. Significant binding was not obtained with MOLT-4 cells which do not express CEA (FIG. 19B). There was also no binding with melanoma cells.

We then compared the reactivities of Ab1 (8019) with that of monkey purified Ab3 (50 $\mu$g/ml) by a sensitive immuno-peroxidase assay on human colon tumor and normal colon specimens. The Ab3 antibodies were purified from sera as described above. The method (biotin-streptavidin reagents, Vector, Burlingame, Calif.) has been described in detail elsewhere (Battacharya-Chatterjee (1990) and (1991)). All sections were counterstained with Meyer's hematoxylin. Pertinent specificity tests were performed, including block of the endogenous peroxidase, omission of the first layer, or substitution of nonimmune homologous serum for the specific antiserum and P3-653 myeloma culture supernatant as the control.

Figure 20A:
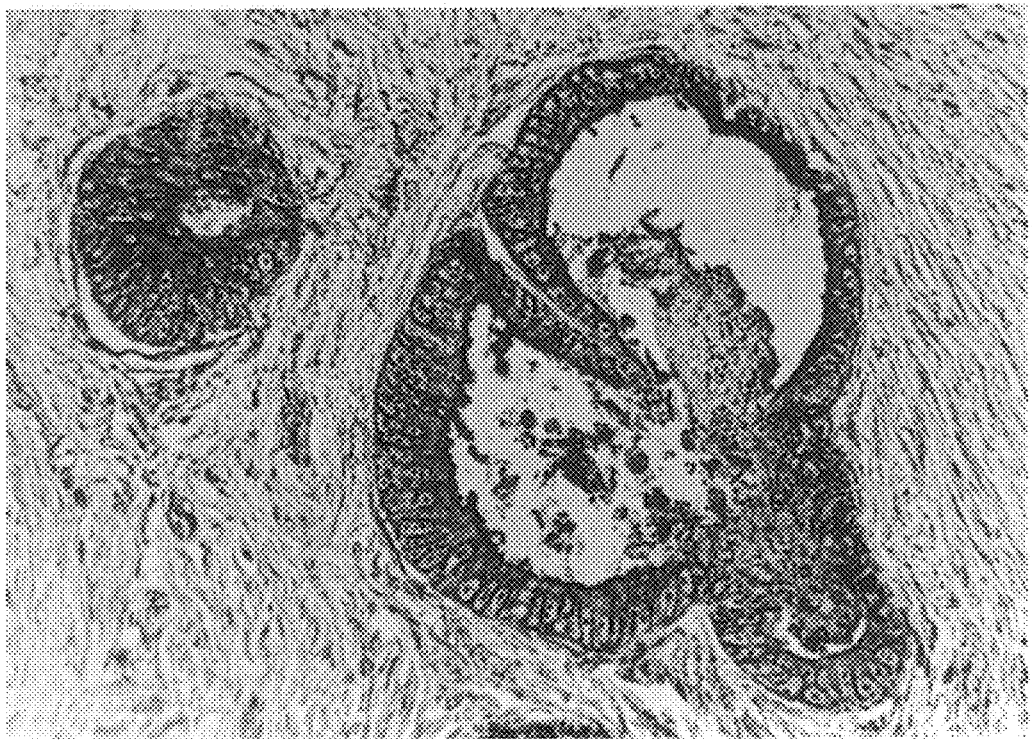
Figure 20B:
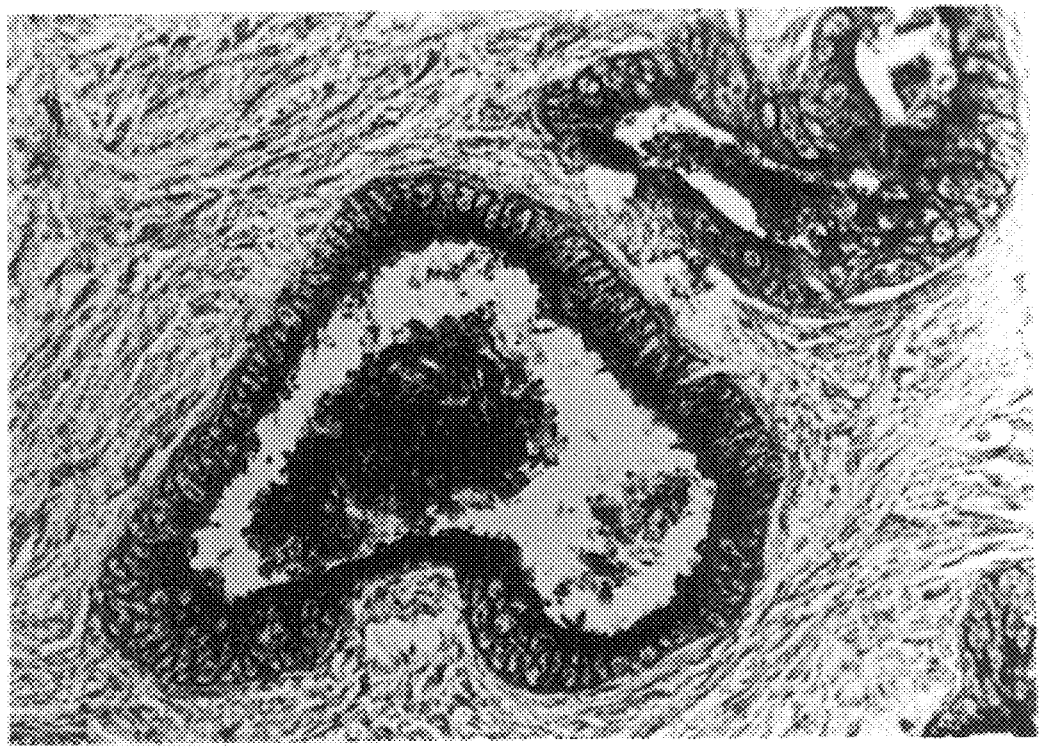
Figure 20C:
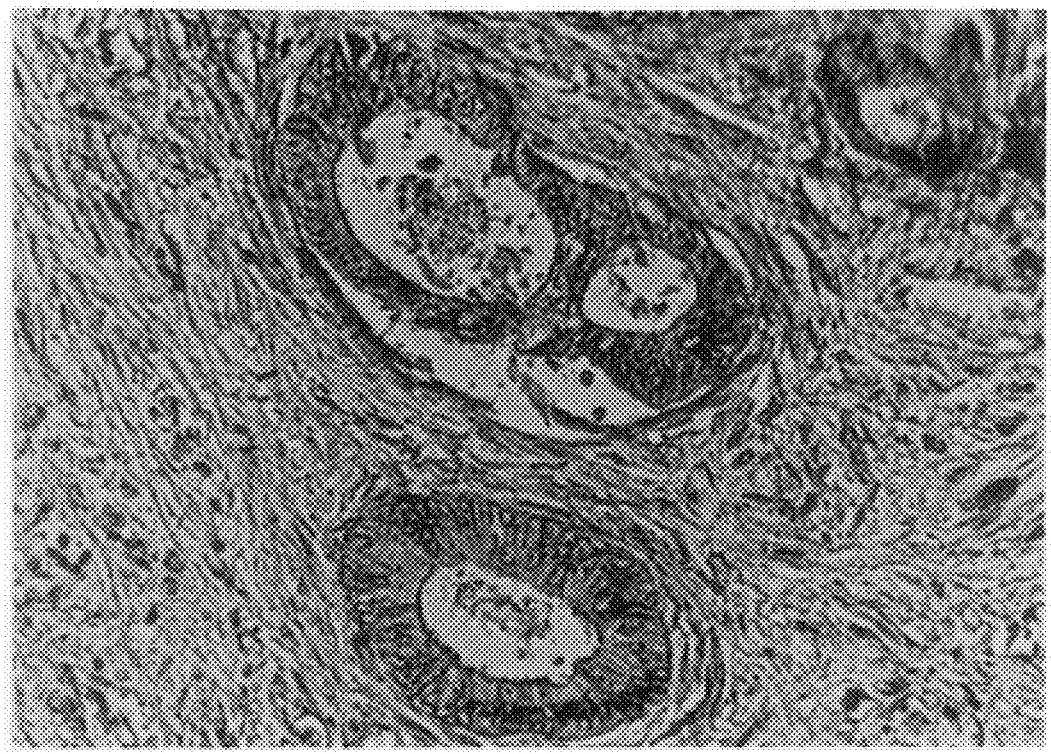
Figure 20D:
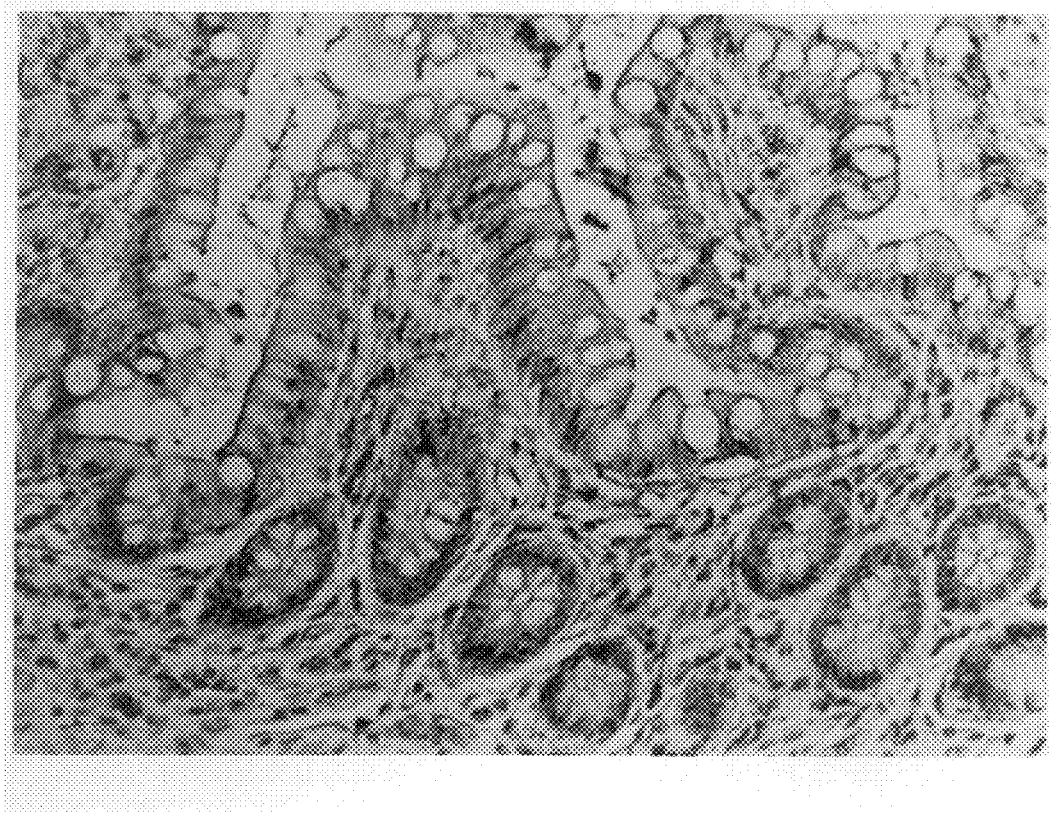

The pattern of reactivity of Ab3 (FIG. 20A) on the colon cancer specimen was identical to those obtained with Ab1 8019 (FIG. 20B) whereas there was no reactivity with unrelated monkey Ab3 (FIG. 20C). Also there was no reactivity of either Ab3 (FIG. 20D) or Ab1 with control normal colon section. Reactions with Ab1 or purified Ab3 (FIGS. 25A through 25C) resulted in the staining of both tumor cells as well a secreted mucinous materials. The staining was apical in gland-like structures and granular (cytoplasmic) in less differentiated areas. Monkey Ab3 was further tested on normal stomach, duodenum, cecum, smooth and striated muscle tissues and found negative.

Figure 21:
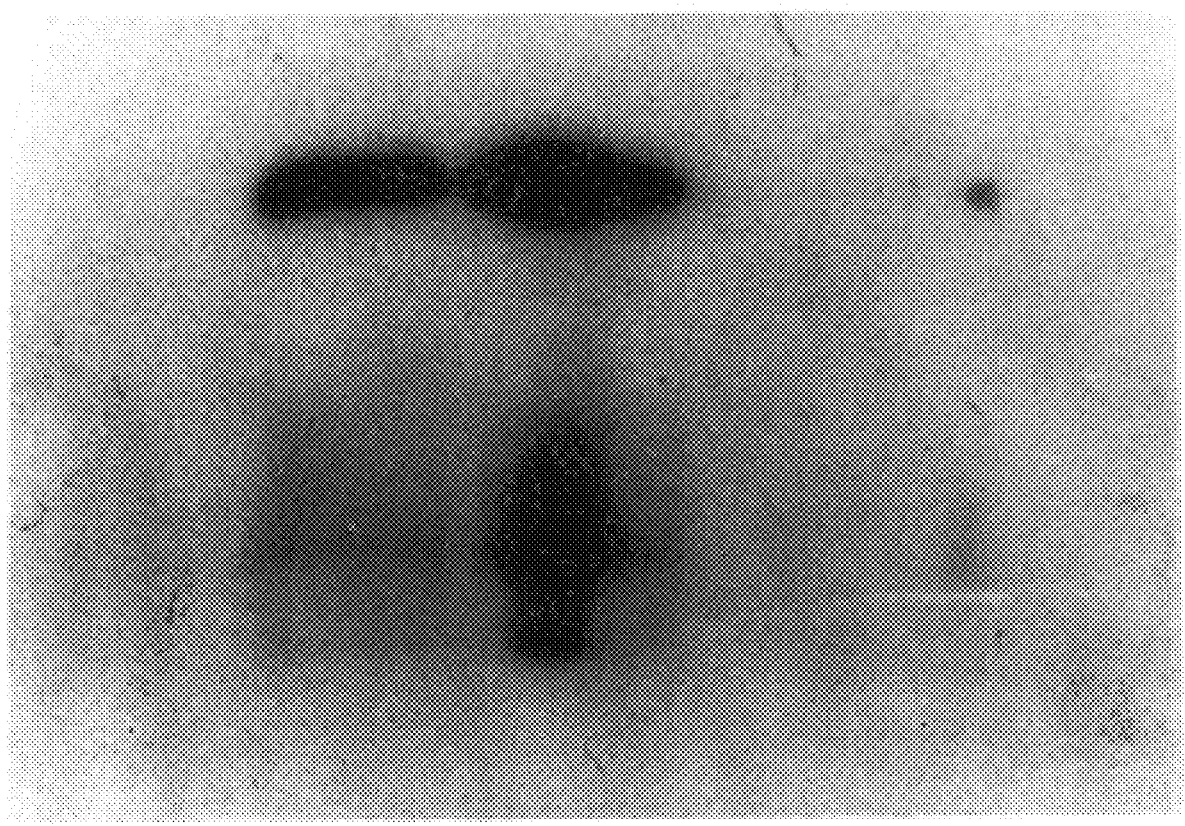
FIG. 21 is a half-tone reproduction of an autoradiogram of an SDS-PAGE gel with $^{125}$I labeled CEA after immunoprecipitation with Ab3 monkey PRO 667 (lane 1), 8019 (lane 2), and Ab3 monkey treated with unrelated Ab2 (lane 3).

To further exclude the possibility that the Ab3 antibodies react with a minor contaminant in the purified CEA preparation, or that these antibodies stain a non-CEA membrane protein on tumor cells, we identified the molecular species precipitated by the monkey purified Ab3. Purified CEA was labeled with $^{125}$I by the Chloramine T-method and reacted with purified Ab3 (10 $\mu$g) or Ab1 (10 $\mu$g) or unrelated control Ab3 from monkey immunized with Ab2 11D10 (10 $\mu$g) or PBS-BSA control, previously adsorbed onto protein G-Sepharose beads. After washings, the antigen-antibody coated beads were analyzed by SDS-PAGE according to the method of Laemmli ((1970) Nature 227:680–685) and radioautographed. As seen in FIG. 21, the radiolabeled material was precipitated by the monoclonal 8019 (Ab1) and the monkey Ab3. The molecular weights by SDS-PAGE was identical.

(d) Epitope analysis of Ab3 using LS174-T cells

To demonstrate that Ab3 generated in monkeys and Ab1(8019) bind to the same antigenic determinant, inhibition of 8019 binding to the antigen positive tumor cell line LS174-T cells or CEA by purified Ab3 was checked by RIA as described (Bhattacharya-Chatterjee et al. (1990) and (1991)). This assay was done in disposable microfold 96-well microfilter-coated plates. The plate was first treated with 10% FCS and 1% BSA in PBS. In a typical assay, triplicate 50-$\mu$L aliquots of various dilutions of purified Ab1 or Ab3 preparation and 5×10$^5$ viable cells in 50 $\mu$l of PBS were co-incubated with a fixed amount of radiolabeled Ab1 (~50,000 cpm) in individual wells for 2 hour at room temperature with continuous shaking.

After incubation, the plate was washed three times with PBS/1% BSA by suction. The radioactivity in the washed filter paper was determined in a K-ray spectrometer.

Percent inhibition of the assay was calculated according to the formula:

$$\% \text{ inhibition} = \left[1 - \frac{R_t - R_c}{R_{\max} - R_c}\right] \times 100$$

in which $R_T$ was the average cpm of the experimental well with inhibitors. $R_C$ was the average background cpm and $R_{max}$ was the average maximal binding without any inhibitors.

Figure 22:
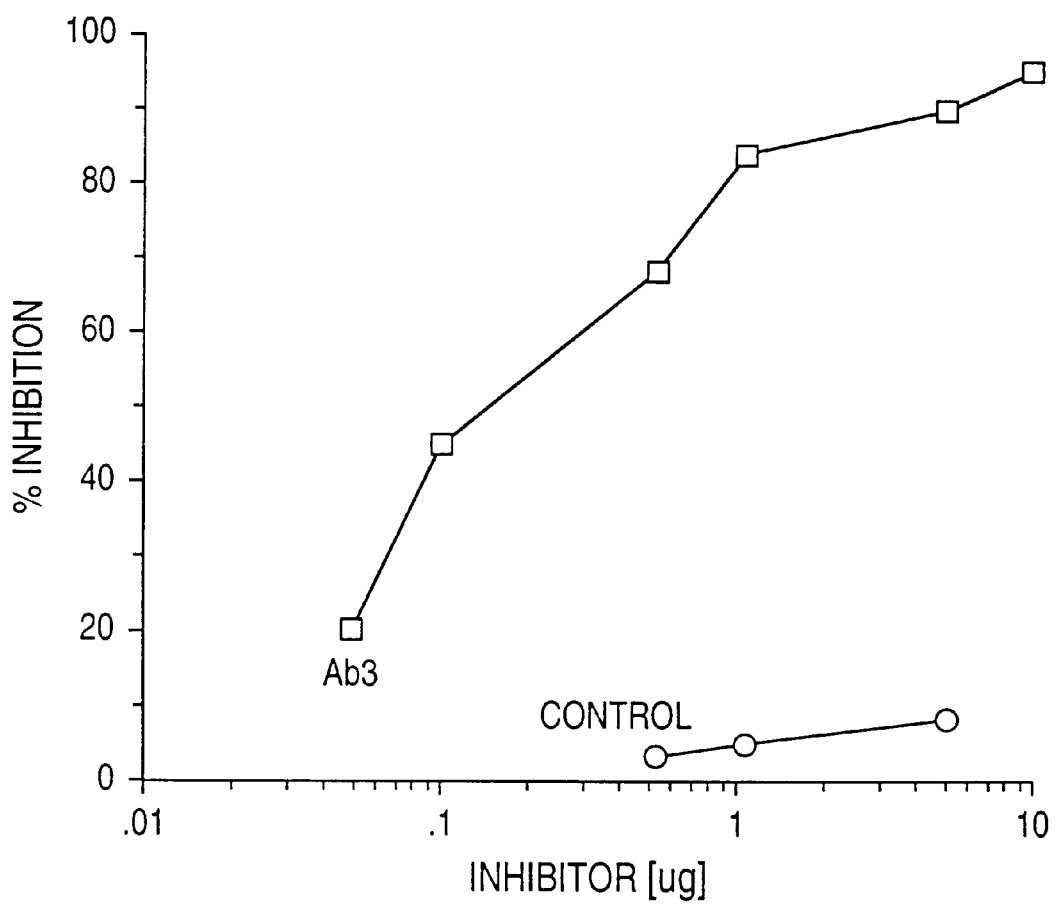
FIG. 22 is a graph depicting inhibition of Ab1 binding to LS174-T cells by purified monkey Ab3. Squares with a dot in the center denote purified Ab3 from monkey immunized with 3H1. Open circles denote purified Ab3 from monkey immunized with control 11 D-10.

If Ab3 has a similar binding site as Ab1, it should compete with Ab1 for binding to CEA on LS174-T cells. A fixed amount of radiolabeled Ab1 was co-incubated with different amounts of purified Ab3 or control Ab3 preparations and LS174-T cells (FIG. 22). One hundred and fifty nanograms of purified Ab3 inhibited binding by 50% and 1 µg of purified Ab3 gave over 80% inhibition, whereas the control Ab3 used at a 5 µg concentration did not produce any inhibition. Similarly, 50% inhibition of binding was obtained with 93 ng of Ab1. These results indicate that Ab2-immune monkey antibody binds to the same antigen as Ab1 and therefore the Ab3 preparation contains antibody molecules with Ab1 properties.

Example 4

Analysis of Immune Response Elicited in Humans With Advanced CEA-Associated Disease By 3H1

Selection of Patients

Twelve patients participated in the study (Table 2). All of the patients had CEA positive advanced colorectal carcinoma and failed standard therapies (Table 2).

Baseline studies included complete physical examination, chest radiography, computer axial tomography examination of the abdomen, serum CEA level, routine blood counts and chemistries. All of the patients had been off prior therapy for at least four weeks and staging was repeated at the conclusion of therapy.

Treatment Schedule

The patients were treated intracutaneously with either 1 mg, 2 mg or 4 mg of aluminum hydroxide precipitated 3H1 (Example 2) every other week for four injections. If the patients were stable at the end of the four injections, they were then continued with injections or a monthly basis and evaluated every three months. Patients were removed from study if they demonstrated growth of their tumor.

Preparation of Ab2

3H1 was obtained as described in Example 1 and alum-precipitated as described in Example 2. The final product was tested for sterility, pyrogenicity and general safety in guinea pigs before use. An Investigational New Drug Application was approved through the United States Food and Drug Administration (BB-IND 5055). Before administration, 3H1 was heat treated in the presence of adjuvant at 45° C. for 30 minutes in a water bath.

Purified CEA

Purified CEA was obtained commercially from Rougier Bio-tech, Montreal, Canada (cat. no. 70015). CEA was isolated from human liver metastasis of colonic tumors by perchloric acid extraction and purified twice by ion-exchange chromatography followed by gel filtration and several steps of HPLC chromatography. The CEA is 100% pure, produced a single band at 180,000 m.w. by high power liquid chromatography and SDS-PAGE and was immuno-precipitated as a single band by horse as well as rabbit anti-CEA antibody. The CEA preparation was resolved into two closely migrating bands at 180,000 and 200,000 m.w. by Western blot analysis using murine monoclonal antibody anti-CEA. We rechecked the material by Western blot analysis using monoclonal antibody 8019.

Toxicity and Clinical Responses

Toxicity was minimal with only local reactions at the injection site with mild erythma and induration and mild fever and chills relieved by acetaminophen. The anti-idiotypic treatment did not have any deleterious effect on hematopoietic cells, renal or hepatic function. Patients were monitored very closely for disease activity. Eleven patients have had progressive disease (Table 2). The remaining patient was stable at ten months into therapy.

Serial Monitoring of Circulating CEA

Indirect measurement of extent of disease (CEA level) was recorded prior to immunization and determined after

TABLE 2

Patient Characteristics

| Patient No. | Age/Sex | Dosage (mg) | No. Doses | Metastatic Disease | Baseline CEA Level | Humoral Response | Cellular | Off Study Study | Why Off |
|---|---|---|---|---|---|---|---|---|---|
| 1 | 72/M | 4 | 7 | lung | 160 | + | + | 03/10/94 | progression |
| 2 | 43/F | 2 | 4 | liver | 110 | + | + | 12/09/93 | progression |
| 3 | 46/F | 1 | 4 | lung, liver | 140 | + | + | 12/02/93 | progression |
| 4 | 61/F | 2 | 4 | lung, ileum | 60 | − | − | 12/11/93 | progression |
| 5 | 60/M | 1 | 7 | lung, liver | 3 | + | − | 05/02/94 | progression |
| 6 | 68/M | 4 | 8 | lung, liver | 81 | + | − | 05/16/94 | progression |
| 7 | 47/M | 2 | 4 | liver | 15 | + | + | 03/17/94 | progression |
| 8 | 80/F | 4 | 4 | liver | 42 | − | − | 03/17/94 | progression |
| 9 | 51/M | 4 | 4 | liver | 210 | + | + | 04/07/94 | progression |
| 10 | 36/M | 1 | 8 | pelvis | 1 | − | − | 06/28/94 | progression |
| 11 | 70/M | 4 | 12 | lung | 58 | + | + | | |
| 12 | 53/F | 2 | 5 | lung, liver | 35 | + | + | 06/09/94 | progression | each immunization and then once monthly following completion of the immunization schedule. For this, patients' sera were heat-inactivated to precipitate the immunoglobulins which would interfere with the CEA monitoring assays involving murine monoclonal Ab1. CEA is heat stable, and was measured in the clear centrifuged supernatant by routine assay. The serial monitoring of CEA correlated with disease progression and all patients who clinically progressed and a rise in their serum CEA levels except patients five and ten who did not secrete CEA.

For quantification of CEA in heat-extracted serum, 1 ml of 0.2 M sodium acetate buffer, pH 5.0 was added to 0.5 ml of serum, vortex-mixed, incubated for 15 min. at 900 C, and centrifuged (1200×g, 10 min). The supernatants were assayed the same day or stored frozen at −20° C. until assay. One hundred microliters of supernatant was then assayed by the enzyme immunoassay for CEA as described (Hansen et al. (1989) *Clin. Chem.* 35(1):146–151).

Assays for Humoral Immunity (a) Total anti-3H1 response

The development of humoral immunity induced by immunization with alum-precipitated 3H1 was assessed by testing sera obtained from patients before therapy and after each treatment with the vaccine. The sera were initially tested for total human anti-murine-antibody responses including anti-iso/allo/and anti-anti-idiotype antibodies by sandwich radioimmunoassay as described by Hansen et al. ((1994) *Clin. Chem.* 35(1):146–151). Briefly, microtiter plates were coated with 3 H1 and incubated with different dilutions of patients' sera. After washings, the antigen-antibody reaction was tagged using $^{125}$I-labeled anti-Id 3H1 in a homogeneous sandwich radioimmunoassay. Since 3H1 is injected as intact IgG1, patients are expected to mount human anti-mouse antibody responses.

Hyperimmune sera (following the fourth injection of 3H1) from nine of twelve patients showed significant levels of total human anti-mouse antibody responses including anti-iso/allo/and anti-anti-idiotypic antibodies against immunizing Ab2, 3H1, as determined by homogeneous sandwich radioimmunoassay.

(b) Specific Ab3 Response to Ab2

Next the sera from these immunized patients were checked for their ability to inhibit the binding of $^{125}$I-labeled Ab1, 8019, to Ab2 3H1 on the plate by radioimmunoassay or vice versa (inhibition of radiolabeled Ab2 binding to Ab1 on the plate). These reactions were done in the presence of excess normal murine immunoglobulin to block human antibodies against isotypic and allotypic determinants.

Crude sera obtained from patients after the fourth treatment were pre-incubated with normal murine immunoglobulin to block human antibodies against isotypic and allotypic determinants. We routinely used post fourth immunization because this was the number of injections all 12 patients received. For patients who received more than four injections, immune responses remained comparable or continued to increase in titer. Serial dilutions of sera were then tested for inhibition in the Ab1–Ab2 binding assay. All assays were performed in triplicate. For direct binding inhibition assay between Ab1 and Ab2, purified 3H1 (Ab2) was used to coat plates (500 mg/well) and the binding of radiolabeled 8019 (Ab1) to Ab2 was tested for inhibition in the presence of different patients' hyperimmune Ab3 sera and Ab1. This demonstrated whether Ab3 in patients' sera shared idiotopes with 8019 (Ab1). Also, this inhibition assay between Ab1–Ab2 binding by Ab3 sera indicated whether Ab3 is a true anti-anti-idiotype. Unrelated Ab2 was used as control. After washings, the antigen-antibody reaction was tagged using $^{125}$I-labeled anti-idiotype reagent in a homogeneous sandwich radioimmunoassay as above. Pretreatment, nonimmune sera and sera from normal donors were used as controls.

Figure 23:
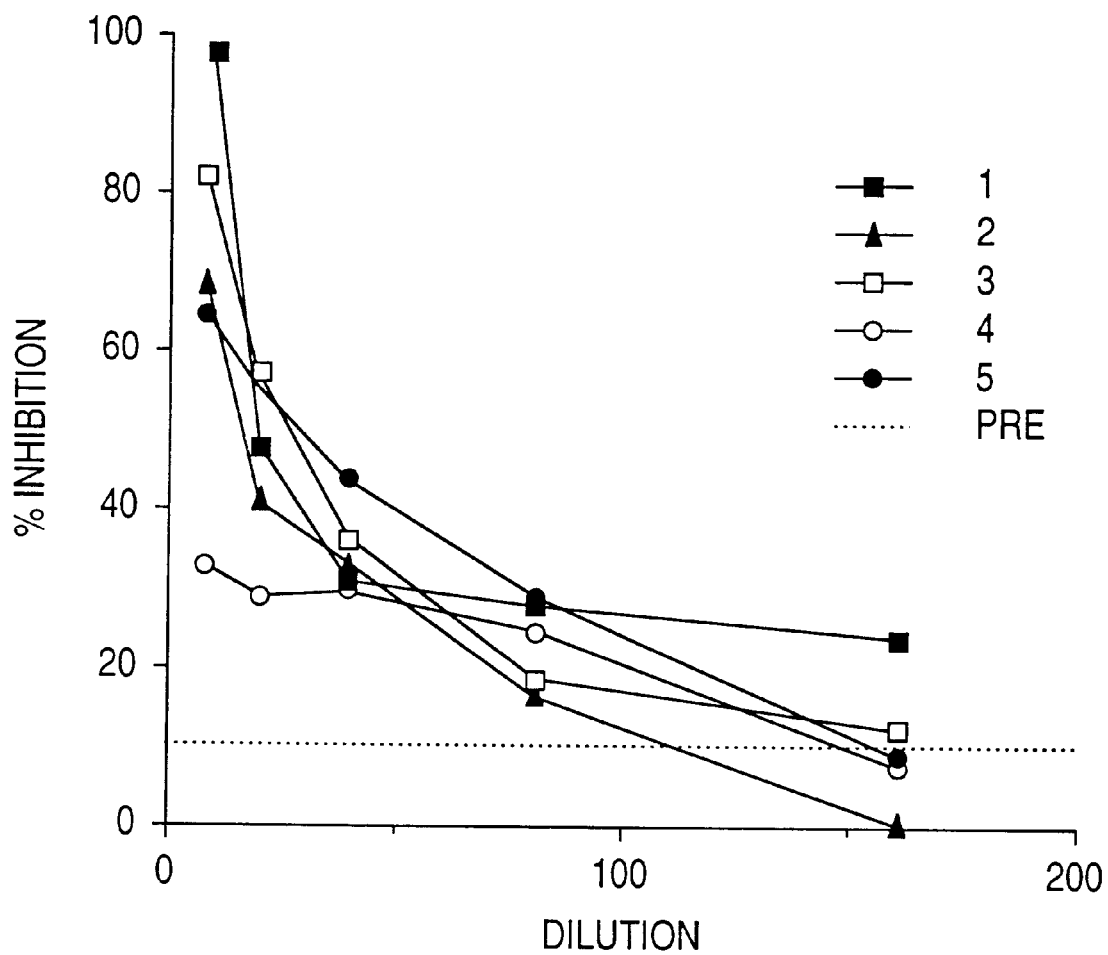
FIG. 23 is a graph depicting inhibition of Ab1 (8019) binding to 3H1 by human Ab3 sera by RIA. Solid squares denote patient #1; solid triangles denote patient #2; open squares denote patient #3; open triangles denote patient #4; solid circles denote patient #5. The dotted line represents preimmune serum.

FIG. 23 demonstrates representative data from the first five patients. Sera from patients No. 1, 2, 3 and 5 at 1/10 dilution, inhibited binding of iodinated 8019 to 3H1 by 62–100 percent and inhibition of binding decreased with increasing dilution of the sera. Sera from patient No. 4 showed minimal non-specific inhibition at all dilutions used and preimmune sera showed no inhibition. Although steric hindrance by Ab3 binding can not be excluded in these assays, the results suggest the presence of true anti-anti-idiotypic antibodies that share idiotypes with Ab1. Again, nine out of twelve patients were positive for Ab3 responses by this assay.

(c) Induction of Anti-CEA Antibodies by 3H1

This assay was conducted to determine whether some of the Ab3 induced in patients by 3H1 Ab2 were of the Ab1 type and will bind to CEA. A pure preparation of CEA obtained from Rougier Biotech (as described above) was used to reduce the risk of obtaining false positive results due to nonspecific binding. Purified CEA was radioiodinated with $^{125}$I by the Chloramine T method. Radiolabeled CEA (1 10$^6$ cpm) was reacted with 0.5 ml of patient's serum pre-adsorbed on protein G-Sepharose beads. After reactions, the beads were washed and counted in a gamma-ray spectrophotometer. Each sample was performed in duplicate and the mean of the cpm bound is shown. Pre-immune sera, phosphate buffered saline-bovine serum albumin, as well as Ab3 sera obtained from a patient treated with an unrelated murine monoclonal antibody for T cell lymphoma were used as controls in these assays.

Figure 24:
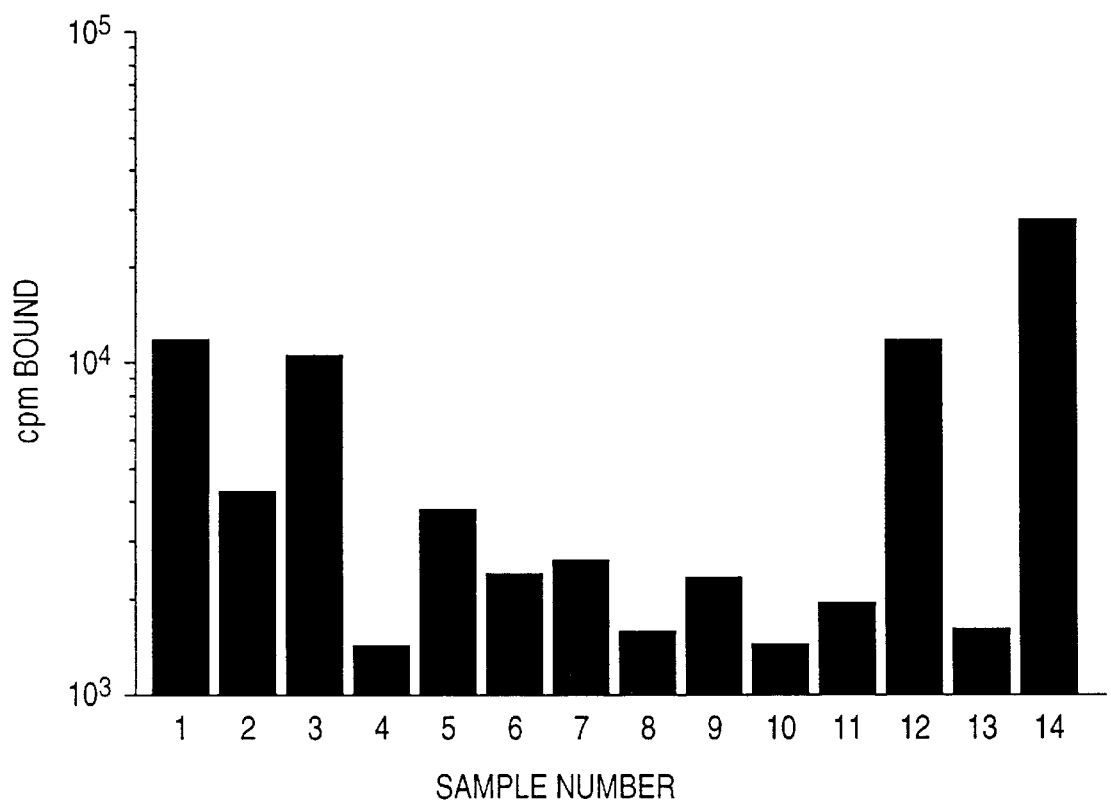
FIG. 24 is a bar graph depicting the reactivity of human Ab3 with purified radiolabeled CEA. Each bar represents a sample, with samples 1–12 from patients 1–12, sample 13 a PBS-BSA control, and sample 14 was Ab1 8019 (10 µg).

As shown in FIG. 24, immunization with 3H1 induced antibodies that bound to radiolabeled CEA. Nine of twelve patients developed anti-CEA antibodies measurable by this assay. Patients No. 4, 8 and 10 were anergic for human anti-mouse antibody response and did not produce antibodies against CEA, while patients No. 1, 2, 3, 5 and 12 showed high binding, and patients No. 6, 7, 9 and 11 showed binding greater than the background count obtained with PBS-BSA (Sample No. 13) or pre-immune sera (data not shown). Sample No. 14 was used as a positive anti-CEA (8019) control. Pre-treatment, non-immune sera and sera from normal donors were used as controls in these assays.

(d) Flow Cytometry (FACS) Analysis with Ab1 and Patient's Ab3

To determine the reactivity with cell-cultured surface CEA, CEA-positive colorectal cancer derived LS174-T cells (1×10$^6$ per well) and CEA-negative B cell lymphoma, Raji cells (1×10$^6$ per well) were reacted with Ab1(8019) and patient's immune sera (Ab3) at 1:100 dilution at 4° C. for 60 minutes. After washing, the cells were incubated with either goat anti-human or goat anti-mouse F(ab')$_2$ IgG-FITC labeled antibody (Tago) for 30 minutes at 40° C. They were then washed twice, fixed in 2 percent paraformaldehyde and analyzed by flow cytometry (FACS Star, Becton Dickinson). Preimmune patient's sera were used as a control.

Figure 25A:
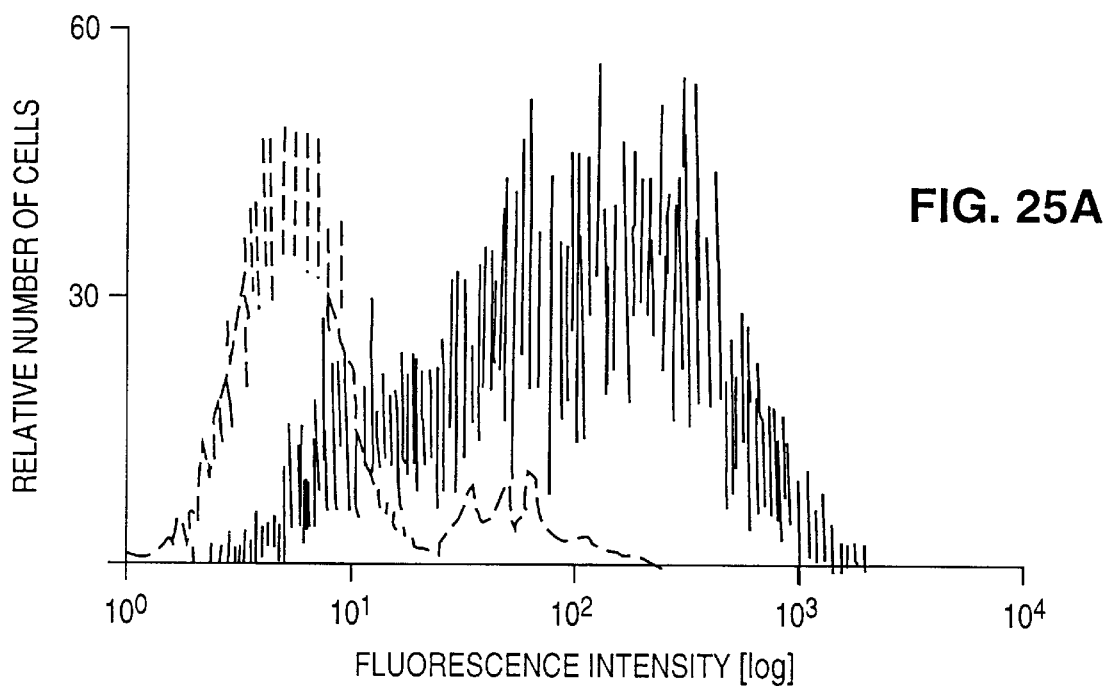
FIGS. 25A to 25C are reproductions of traces showing flow microfluorimetry analysis of reaction of CEA positive colon cancer cell line LS174-T with patients' Ab3 sera. Tumor cells were reacted with Ab3 sera from patients immunized with 3H1 and murine Ab1 (FIG. 25A). In (FIG. 25B), human B lymphoma cells that do not express CEA (Raji) were reacted with Ab3. Solid line denotes Ab3 sera; dotted line denotes preimmune sera.
Figure 25B:
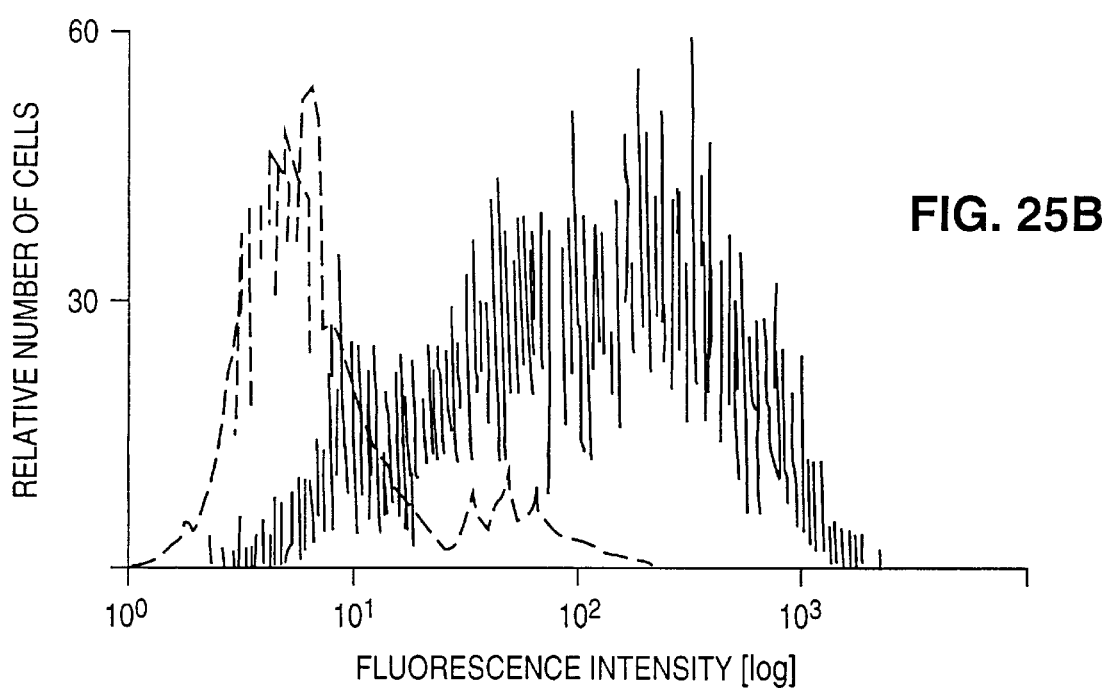
Figure 25C:
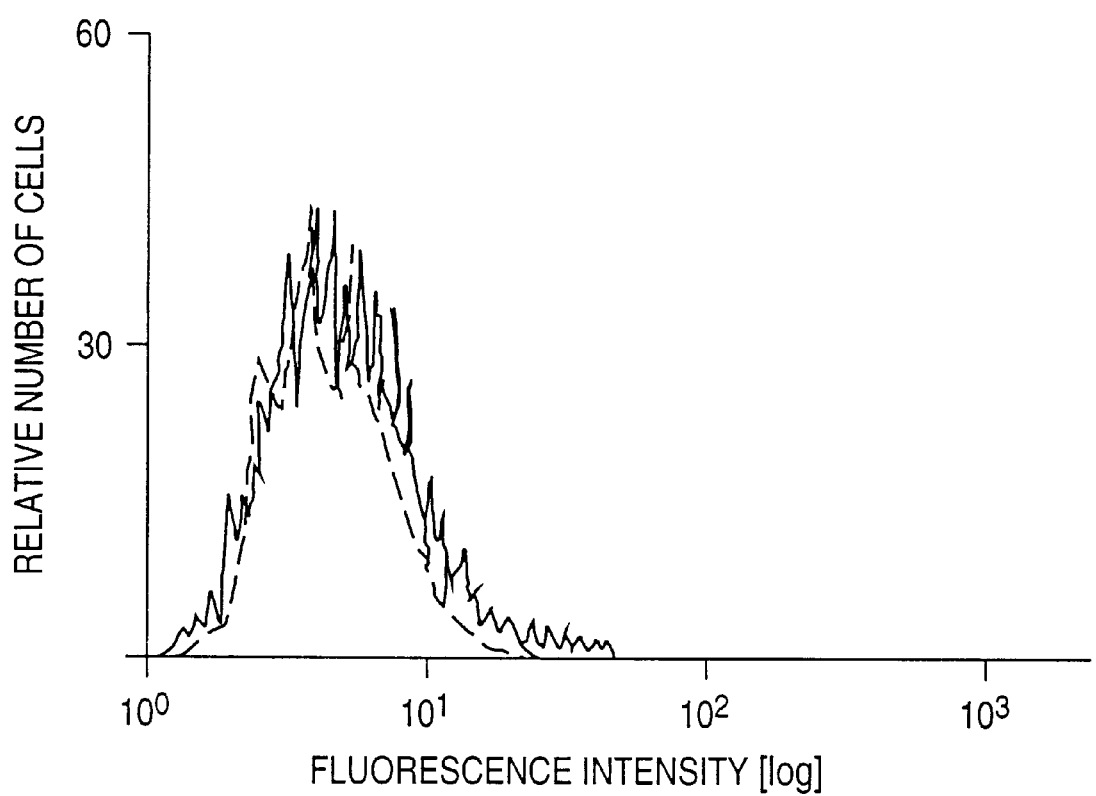
Figure 26:
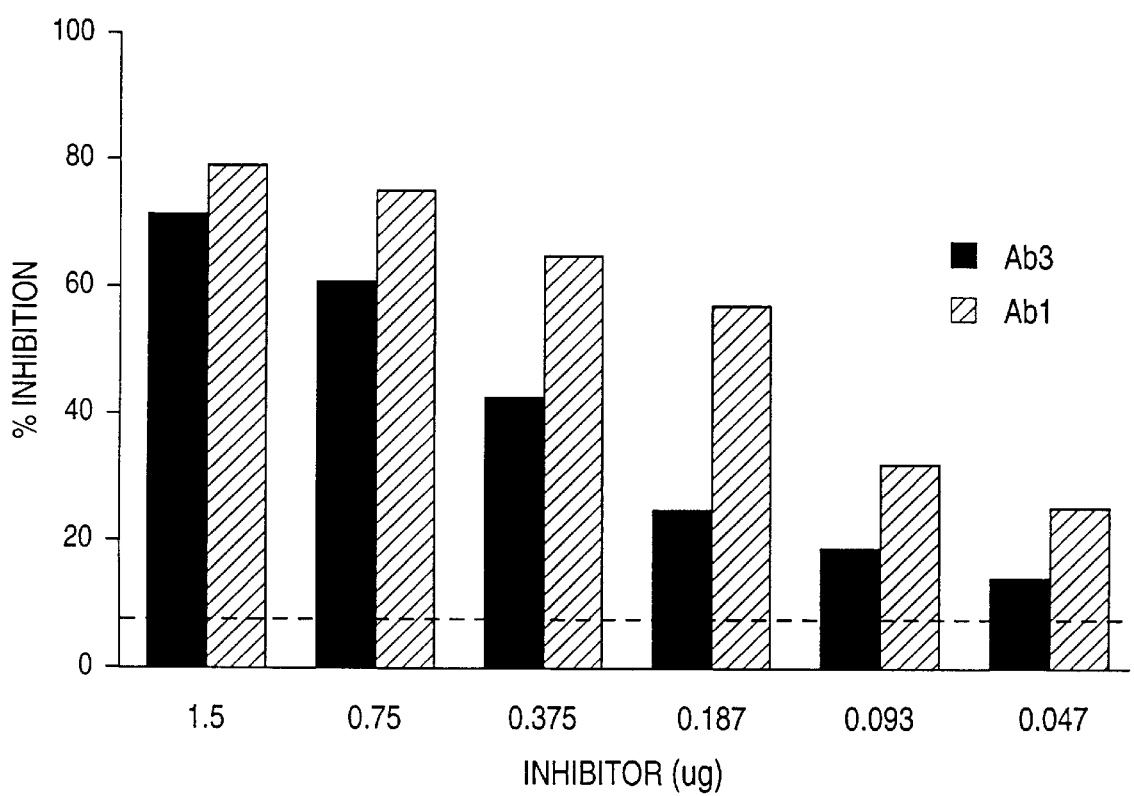
FIG. 26 is a bar graph depicting inhibition of Ab1 binding to LS174-T cells by patients' Ab3. Solid bar denotes Ab3; hatched bar denotes Ab1.

As shown in FIGS. 25A through 25C, crude sera from a representative 3H1-immunized patient bound to LS174T cells (FIG. 25A) similar to the binding pattern obtained with 8019 (FIG. 25B) and did not bind to human B cell lymphoma cells which do not express CEA (FIG. 25C). Similar results were found with all of the positive patients.

(e) Competition of Ab1 and Patients' Ab3 for Binding to LS174-T Cells

If Ab3 has a similar binding site as Ab1, it should compete with Ab1 for binding to CEA on LS174-T cells. A fixed amount of radiolabeled 8019 (~90,000 cpm) was co-incubated with different concentrations of patient's purified Ab3 or Ab1 preparations and LS174-T cells.

Ab3 was purified from patients' sera as follows. Fifty milliliters of hyperimmune serum were passed over an immunoadsorbent column consisting of immunizing anti-idiotype immunoglobulin (3H1) coupled to Sepharose 4B. Anti-anti-idiotypic antibodies (Ab3) bound to the column were eluted with 0.1 M glycine-hydrochloric acid buffer (pH 2.4). The eluted antibody was neutralized with 3M Tris, dialyzed against PBS, pH 7.2 and then passed over an immunoadsorbent column consisting of allotype matched normal mouse immunoglobulin coupled to Sepharose 4B to remove anti-isotypic and anti-allotypic reactivities. Antibody that passed through was concentrated and used as purified Ab3. The isotope of Ab3 was determined by ELISA using human anti-isotope specific reagents (Tago).

Figure 27:
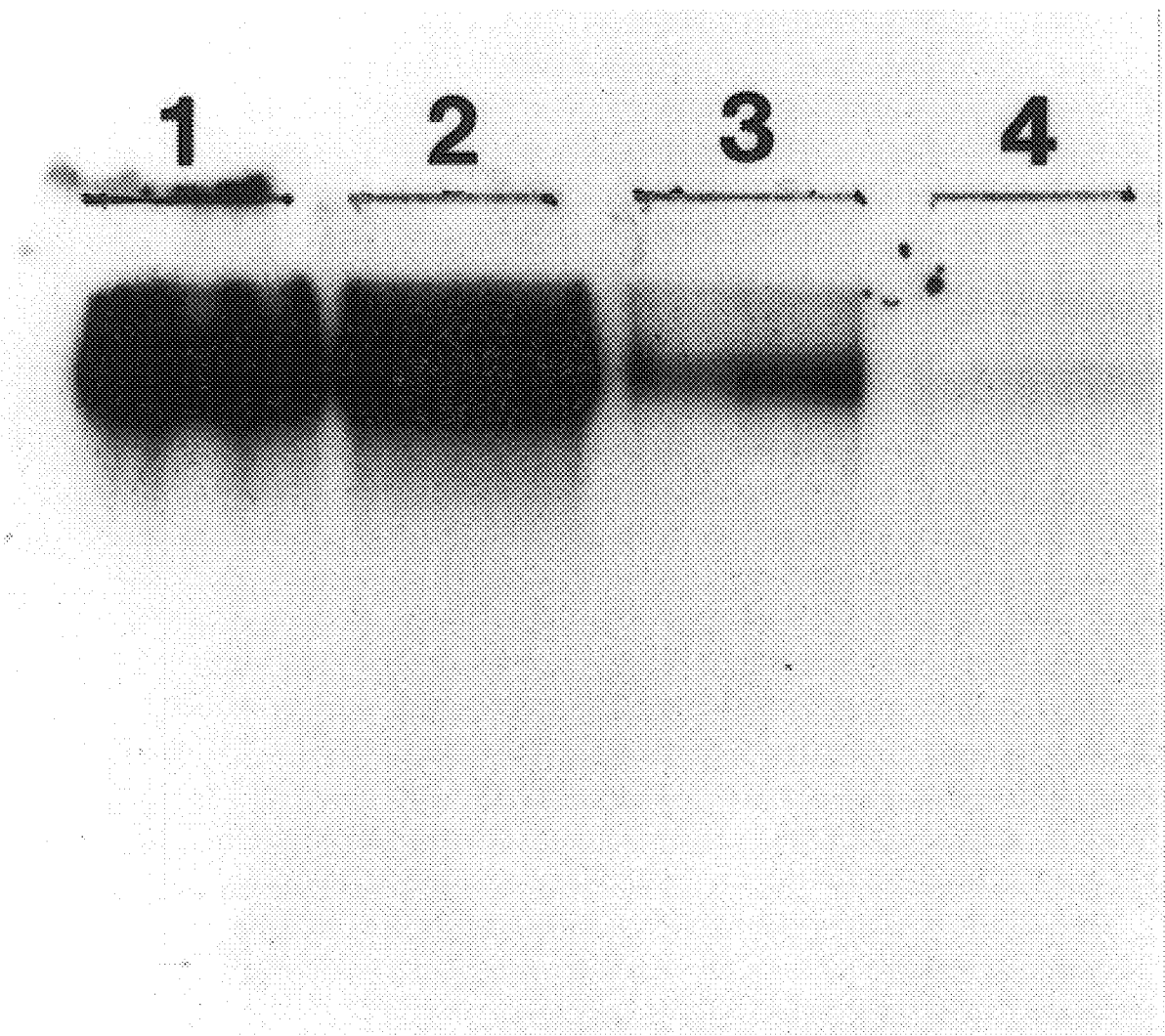
FIG. 27 is a half-tone reproduction of an autoradiogram of an SDS-PAGE gel separating $^{125}$I-labeled CEA after immunoprecipitation with 8019 (lane 1), Ab3 from patient number 1 (lane 2), Ab3 from patient number 2 (lane 3), and Ab3 from a patient treated with unrelated Ab2 (lane 4).

As FIG. 27 shows, purified 8019-IgG1 (Ab1) inhibited binding by 80% at 0.75 $\mu$g whereas patient's purified Ab3 (from patient No. 1) produced 60 percent inhibition at the same concentration. Overall, the inhibition curves obtained with Ab1 and Ab3 were very similar at different dilutions. This indicated that the patient's Ab3 bound to the same antigenic epitope as Ab1 and therefore contained antibody molecules with Ab1 properties.

(f) Immunoprecipitation of CEA by Ab1 and Ab3

Purified CEA was labeled with $^{125}$I by The Chloramine T-method and reacted with purified Ab3 (10 $\mu$g) or Ab1 (10 $\mu$g) or unrelated control Ab3 from lymphoma patient (10 $\mu$g) or PBS-BSA control, previously adsorbed on to protein G-Sepharose beads. After washings, the antigen-antibody coated beads were analyzed by SDS-PAGE according to the method of Lamella ((1970) Nature 227:680–685) and radioautographed.

It had been previously shown that Ab1 8019 specifically immunoprecipitated the 180,000 m.w. CEA by SDS-PAGE analysis (Bhattacharya-Chatterjee (1990)). To confirm that the Ab3 induced by 3H1 was specific for the CEA molecule, the iodinated purified CEA preparation was immunoprecipitated by purified Ab3 preparations obtained from two patients as well as Ab1 and analyzed by SDS-PAGE. The results in FIG. 27 indicate that both patient's Ab3 (Lane 2 and 3) precipitated the same 180,000 m.w. CEA band as that of murine Ab1 8019 (lane 1). There was no cross-reactivity (lane 4) when the iodinated CEA was reacted with purified Ab3 obtained from a patient treated with an unrelated Ab2 (4DC6). When the iodinated CEA antigen, pretreated with either of the two positive patients' Ab3 preparations, was reacted with 8019, there was no significant immunoprecipitation suggesting that the iodinated preparation was depleted of the CEA antigen (data not shown).

(g) Immunoreactivity of Ab3 with Tumor Sections

The reactivities of monoclonal Ab1 (8019) and purified Ab3 at 10 $\mu$g/ml solution were compared on autologous and allogenic surgical specimens of colonic adenocarcinomas from the patients by immunoperoxidase assay, a very sensitive staining method (biotinstreptavidin reagents, Vector, Burlingame, Calif.) as described in detail elsewhere (Bhattacharya-Chatterjee (1990)). All sections were counterstained with Meyer's hematoxylin. Pertinent specificity tests were performed, including block of the endogenous peroxidase, omission of the first layer, or substitution of nonimmune homologous serum for the specific antiserum and P3-653 myeloma culture supernatant as the control.

Figure 28A:
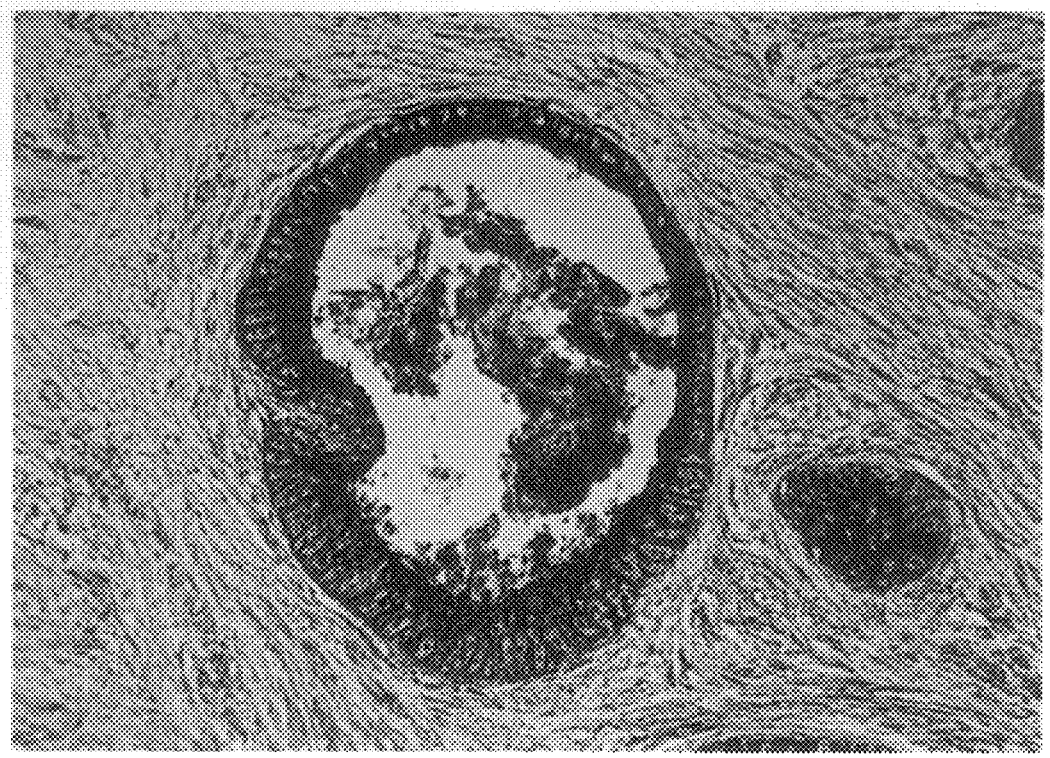
FIGS. 28A to 28F are half-tone reproductions depicting immunoperoxidase staining of autologous and allogeneic colonic adenocarcinomas and normal colon by Ab1 and patients' Ab3. Serial sections were stained with: patients' Ab3 on autologous tumor (FIG. 28A); patients' Ab3 on allogeneic tumor (FIG. 28B); 8019 IgG$_1$ (FIG. 28C); unrelated patients' Ab3 on tumor sections as in FIG. 1 (FIG. 28D); 8019 IgG$_1$ on normal colon (FIG. 28E); and patients' Ab3 on normal colon (FIG. 28F).
Figure 28B:
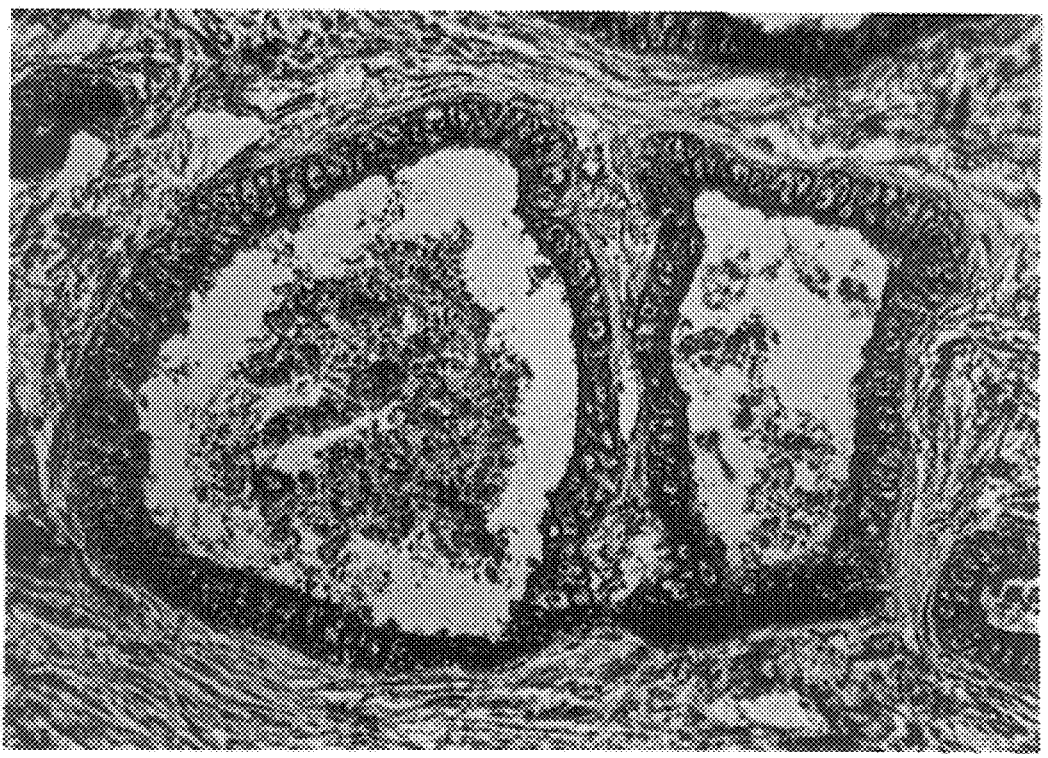
Figure 28C:
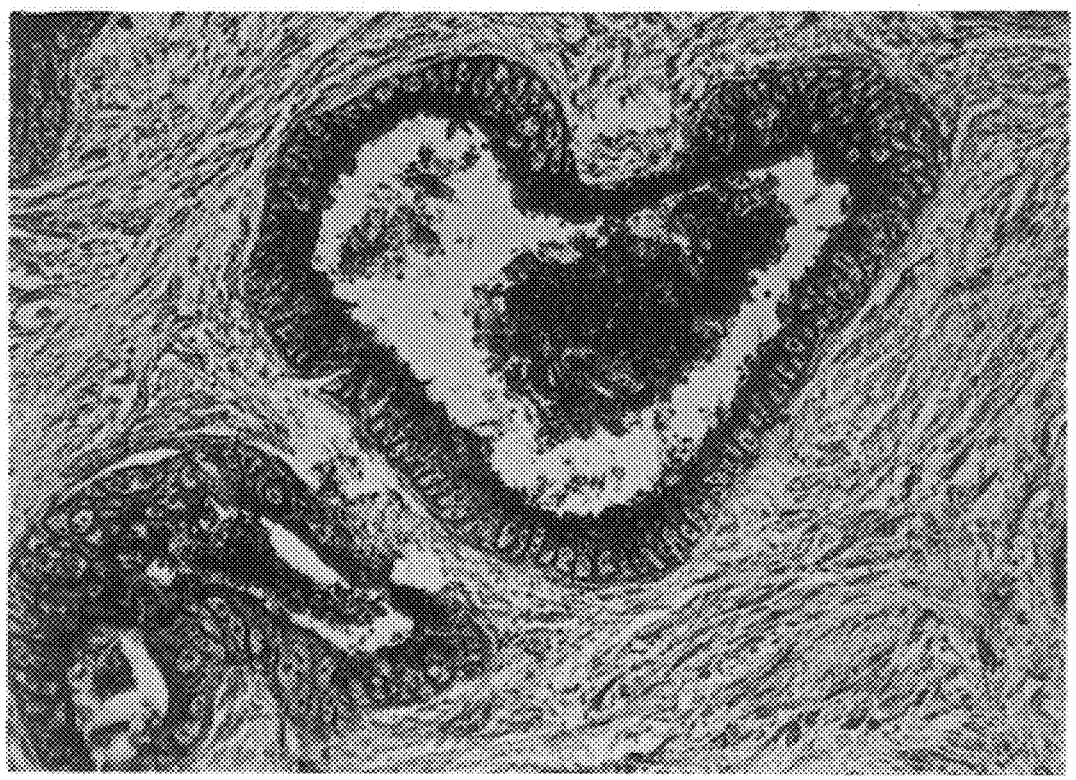
Figure 28D:
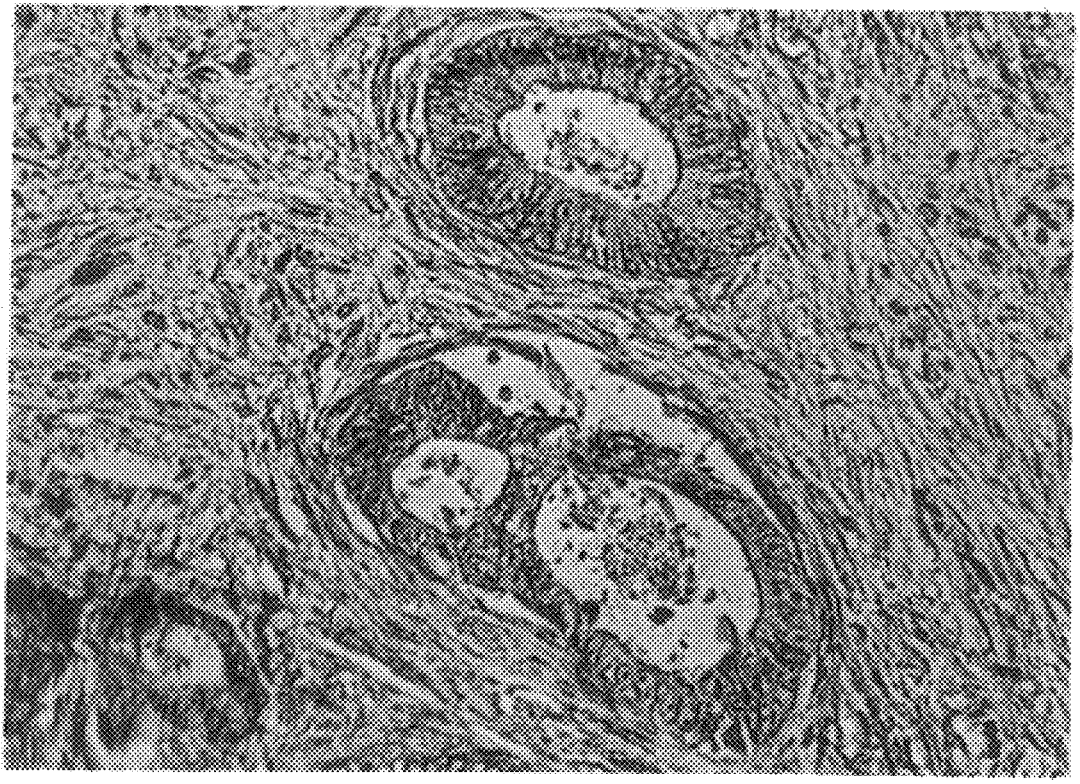
Figure 28E:
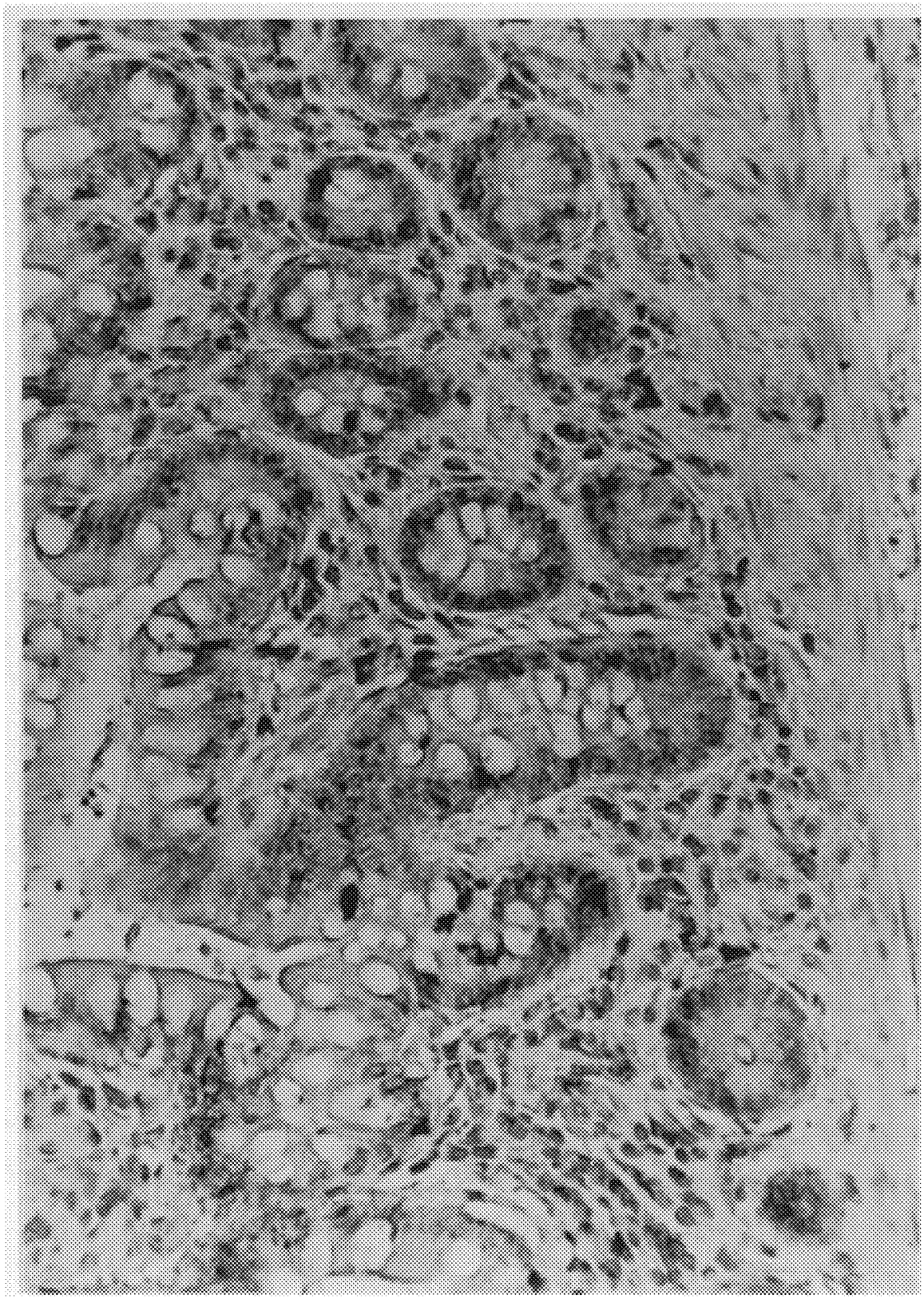
Figure 28F:
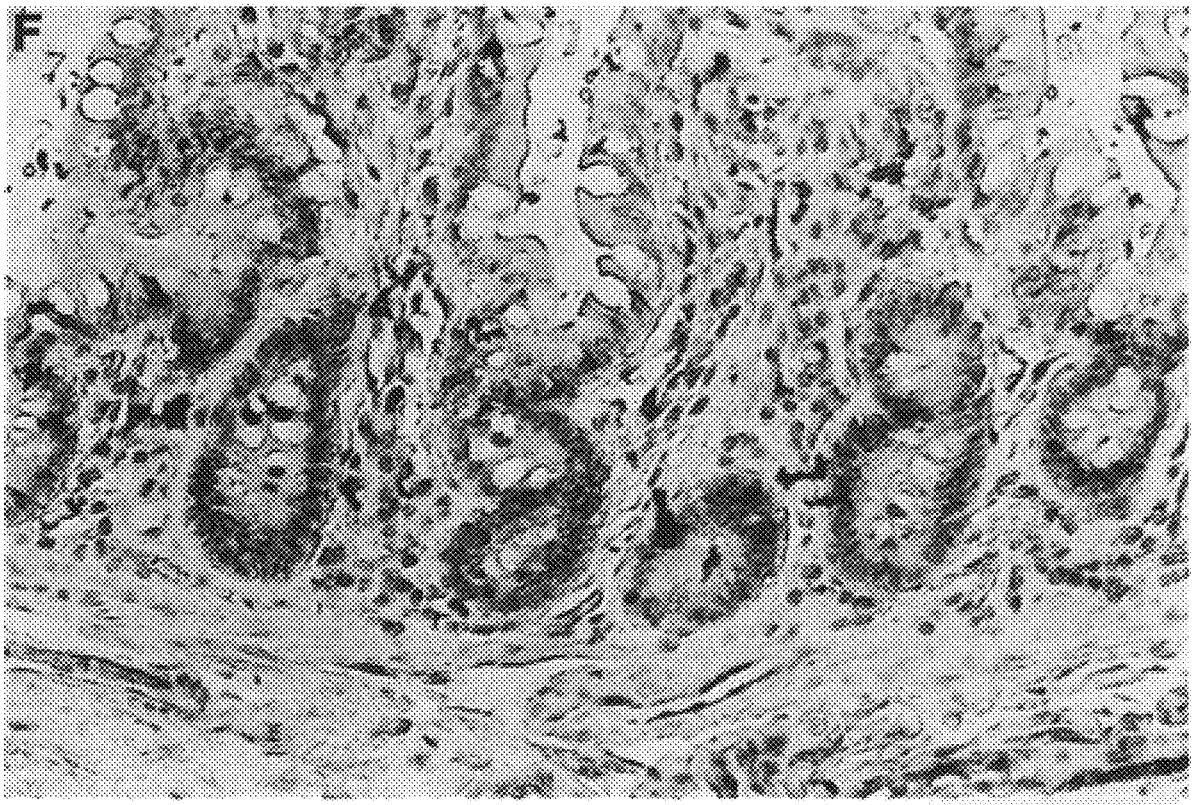

The pattern of reactivity of patient Ab3 on autologous malignant colon tissues was identical to that obtained with allogeneic tumor specimens (FIGS. 28A and 28B respectively). Ab1 8019 showed identical staining patterns (FIG. 28C), whereas there was no reactivity with control Ab3 obtained from a patient treated with an unrelated Ab2 (4DC6) (FIG. 28D). Reactions with Ab1 or purified Ab3 (FIG. 28A, 28B, 28C) resulted in the staining of both tumor cells as well as secreted mucinous materials. The staining was apical in gland-like structures and granular (cytoplasmic) in less differentiated areas. There was no reactivity of Ab1 and purified Ab3 on normal tissues from colon (FIGS. 28E and 28F), cecum, duodenum, stomach striated muscle or smooth muscle.

Assay for T cell Proliferative Response

Cellular immune responses were measured by the proliferation of peripheral blood mononuclear cells incubated with aluminum hydroxide precipitated anti-idiotype antibody 3H1 and aluminum hydroxide precipitated isotope matched control anti-idiotype antibody 4DC6.

Peripheral blood mononuclear cells were isolated from blood obtained after four immunizations by standard Ficoll-Hypaque density gradient centrifugation method and 5×10$^6$ cells per well were incubated with different concentrations of 3H1-Alugel and control 4DC6-Alugel (10 $\mu$g to 2 $\mu$g) in RPMI medium with 5 percent heat-inactivated fetal calf serum and penicillin and streptomycin. The non-specific mitogen phytohemagglutinin-P was used as a positive control at 2 $\mu$g and 1 $\mu$g per well. After the cells were incubated for five days at 37° C. in an atmosphere containing 5 percent carbon dioxide, they were pulsed with $^3$H-thymidine (1 $\mu$Ci per well) for 20 hours. 3H-thymidine incorporation was measured in pre and post-therapy samples. Data were expressed as mean counts (triplicate wells) per minute of $^3$H-thymidine incorporation. The Standard Deviation of the data was <10% for each determination.

Peripheral blood mononuclear cells isolated from some selected patients were also incubated with different concentrations of purified CEA (10 ng to 250 ng) as per protocol above.

Figure 29A:
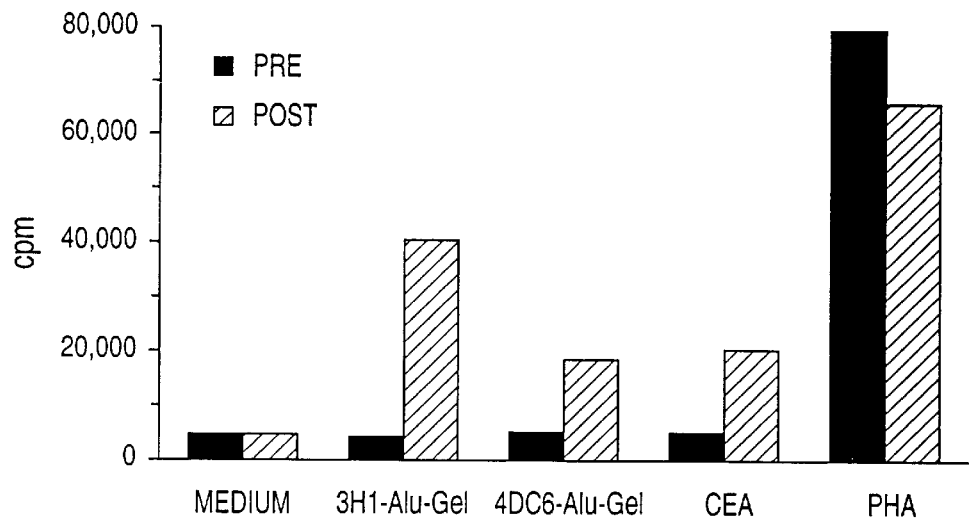
FIGS. 29A to 29B are bar graphs depicting T-cell proliferation assays from two patients (FIG. 29A, number 1.
Figure 29B:
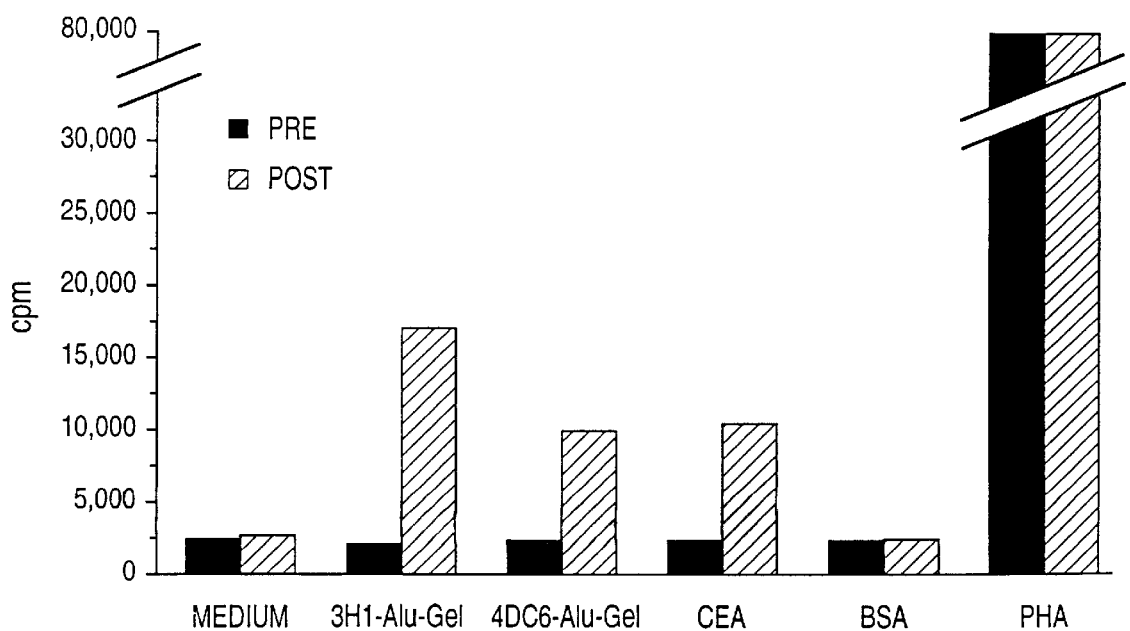

Positive proliferative responses were seen in seven of twelve patients. All seven of these patients developed an Ab3 antibody response (Table 2). Representative data from two patients (No. 1 and 12) are shown in FIG. 29A and 29B. Pre-immune cells had no proliferative response to the anti-idiotype antibody while hyperimmune cells had a significant response. Four of the seven responding patients (two treated with a 2 mg dose and two with a 4 mg dose) also showed T cell proliferation in the presence of purified CEA suggesting antigen specific T cell response. There was also a response to the isotope matched 4DC6 aluminum hydroxide-precipitated anti-idiotype antibody; this response was significantly less than that of the 3H1 response, likely representing a response to the non-idiotype components of the immunoglobulin molecule. The difference in the response to 3H1-Alugel compared to control 4DC6-Alugel was significant ($p<0.003$) as was the response to CEA compared to BSA ($p<0.005$). There was no response to alugel itself (data not shown). Flow cytometric analysis of the cultures demonstrated that greater than 90% of the proliferating cells were CD4 positive T lymphocytes. The three patients who were anergic for human anti-mouse antibody response also did not demonstrate any T cell proliferative response. Of the five non-responders, three were treated with 1 mg, one with 2 mg and one with 4 mg dosage of 3H1-Alugel.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

What is claimed is:

1. Antibody 3H1 which is produced by a hybridoma cell line deposited at the American Type Culture Collection (ATCC) as Accession No. HB12003, or progeny thereof.

2. An antibody comprising the light and heavy chain amino acid sequences of the antibody of claim 1.

3. The antibody of claim 1, further comprising a label capable of producing a detectable signal.

4. Hybridoma cell line deposited at the ACCT as Accession No. HB12003, or progeny thereof.

5. A hybridoma cell line that produces an antibody comprising a light chain containing a variable region with an amino acid sequence identical to the mature variable region amino acid sequence in SEQ ID NO:2, and a heavy chain containing a variable region with an amino acid sequence identical to the mature variable region amino acid sequence in SEQ ID NO:4.

6. An antibody comprising a light chain containing a variable region with an amino acid sequence identical to the mature variable region amino acid sequence in SEQ ID NO:2, and a heavy chain containing a variable region with an amino acid sequence identical to the mature variable region amino acid sequence in SEQ ID NO:4.

7. The antibody of claim 6, further comprising a label capable of producing a detectable signal.

8. A composition comprising an effective amount of the antibody of claim 1, wherein the effective amount is an amount sufficient to elicit a specific immune response against carcinoembryonic antigen (CEA).

9. The composition of claim 8, further comprising a pharmaceutically acceptable excipient.

10. The composition of claim 8, wherein the effective amount is an amount sufficient to elicit a specific immune response against CEA in a human.

11. A composition comprising an effective amount of the antibody of claim 5, wherein the effective amount is an amount sufficient to elicit a specific immune response against carcinoembryonic antigen (CEA).

12. The composition of claim 11, further comprising a pharmaceutically acceptable excipient.

13. The composition of claim 11, wherein the effective amount is an amount sufficient to elicit a specific immune response against CEA in a human.

14. The composition of claim 11, wherein the specific immune response comprises the production of anti-CEA antibody.

15. The composition of claim 11, wherein the specific immune response comprises the production of CEA-specific T cells.

16. The composition of claim 11, further comprising an adjuvant.

17. The composition of claim 16, wherein the adjuvant is aluminum hydroxide.

18. A method of stimulating a specific immune response against carcinoembryonic antigen (CEA) in a human, comprising the step of administering an effective amount of the antibody of claim 1 to the human.

19. The method of claim 18, wherein the specific immune response comprises the production of anti-CEA antibody.

20. The method of claim 18, wherein the specific immune response comprises the production of CEA-specific T cells.

21. A method of stimulating a specific immune response against carcinoembrynoic antigen (CEA) in a human, comprising the step of administering an effective amount of the antibody of claim 6 to the human.

22. The method of claim 21, wherein the specific immune response comprises the production of anti-CEA antibody.

23. The method of claim 21, wherein the specific immune response comprises the production of CEA-specific T cells.

24. A diagnostic kit for detection or quantitation of an anti-carcinoembryonic antigen antibody comprising the antibody according to claim 1 in suitable packaging.

25. A diagnostic kit for detection or quantitation of an anti-carcinoembryonic antigen antibody comprising the antibody according to claim 6 in suitable packaging.

26. A method for determining the presence, absence or amount of anti-CEA antibody in a sample, comprising the steps of a) contacting a sample with the antibody 3H1 of claim 1 under conditions that permit the formation of stable antibody-antigen complex;

b) detecting any complex formed in step a); and c) correlating the absence, presence or amount of complex detected in step b) with the presence, absence or amount of anti-CEA antibody in the sample.

27. A method for determining the presence, absence or amount of anti-CEA antibody in a sample, comprising the steps of a) contacting a sample with the antibody of claim 6 under conditions that permit the formation of stable antibody-antigen complex;

b) detecting any complex formed in step a); and c) correlating the absence, presence or amount of complex detected in step b) with the presence, absence or amount of anti-CEA antibody in the sample.

28. A method for producing antibody 3H1, comprising growing the hybridoma cell line or progeny thereof of claim 4, and producing antibody 3H1.

29. A method for purifying anti-CEA antibody from a sample, comprising the steps of forming a complex between the anti-CEA antibody in the sample and the antibody of claim 6 to form a complex, separating the complex from other components of the sample, and recovering the anti-CEA antibody from the complex.

* * * * *

UNITED STATES PATENT AND TRADEMARK OFFICE
CERTIFICATE OF CORRECTION

PATENT NO.    : 5,977,315
DATED         : November 2, 1999
INVENTOR(S)   : Malaya Chatterjee et al.

It is certified that error appears in the above-identified patent and that said Letters Patent is hereby corrected as shown below:

<u>Column 52,</u>
Line 36, please replace "5" with -- 6 --.

Signed and Sealed this

Eleventh Day of February, 2003

JAMES E. ROGAN
*Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 447 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 22..447

(xi) SEQUENCE DESCRIPTION: SEQ ID NO:1:

```
TCATATGGAT TACTAGTCGA C ATG GTA TCC ACA GCT CAG TTC CTT GGT ATC        51
                        Met Val Ser Thr Ala Gln Phe Leu Gly Ile
                         1               5                  10

TTG TTG CTC TGG TTT CCA GGT ATC AAA TCT GAC ATC AAG ATG ACC CAG        99
Leu Leu Leu Trp Phe Pro Gly Ile Lys Ser Asp Ile Lys Met Thr Gln
             15                  20                  25

TCT CCA TCT TCC ATG TAT GCA TCT CTA GGA GAG AGA GTC ACG ATC ACT       147
Ser Pro Ser Ser Met Tyr Ala Ser Leu Gly Glu Arg Val Thr Ile Thr
             30                  35                  40

TGC AAG GCG AGT CAG GAC ATT AAT GGT TAT TTA AAT TGG TTC CAA CAA       195
Cys Lys Ala Ser Gln Asp Ile Asn Gly Tyr Leu Asn Trp Phe Gln Gln
             45                  50                  55

GAA CCA GGG AAA TCT CCT AAG ACC CTG ATC TAT CGT GCA AAT AGA TTG       243
Glu Pro Gly Lys Ser Pro Lys Thr Leu Ile Tyr Arg Ala Asn Arg Leu
     60                  65                  70

ATA GAT GGG GTC CCA TCA AGG TTC AGT GGC AGT GGA TCT GGG CAA GTT       291
Ile Asp Gly Val Pro Ser Arg Phe Ser Gly Ser Gly Ser Gly Gln Val
 75                  80                  85                  90

TAC TCT CTC ACC ATC AGC AGC CTG GAA TAT GAA GAT ATG GGA ACT TAT       339
Tyr Ser Leu Thr Ile Ser Ser Leu Glu Tyr Glu Asp Met Gly Thr Tyr
                 95                 100                 105

TAT TGT CTA CAG TTT GAT GAG TTT CCG TGG ATG TTC GGT GGA GGC ACC       387
Tyr Cys Leu Gln Phe Asp Glu Phe Pro Trp Met Phe Gly Gly Gly Thr
            110                 115                 120

AAG CTG GAA ATC AAA CGG GCT GAT GCT GCA CCA ACT GTC TCC ATC TTC       435
Lys Leu Glu Ile Lys Arg Ala Asp Ala Ala Pro Thr Val Ser Ile Phe
            125                 130                 135

CCA CCA TCC AGT                                                       447
Pro Pro Ser Ser
        140
```

(2) INFORMATION FOR SEQ ID NO:2:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Ser Thr Ala Gln Phe Leu Gly Ile Leu Leu Leu Trp Phe Pro
 1               5                  10                  15

Gly Ile Lys Ser Asp Ile Lys Met Thr Gln Ser Pro Ser Ser Met Tyr
             20                  25                  30
```

```
Ala Ser Leu Gly Glu Arg Val Thr Ile Thr Cys Lys Ala Ser Gln Asp
         35                  40                  45

Ile Asn Gly Tyr Leu Asn Trp Phe Gln Gln Glu Pro Gly Lys Ser Pro
     50                  55                  60

Lys Thr Leu Ile Tyr Arg Ala Asn Arg Leu Ile Asp Gly Val Pro Ser
 65                  70                  75                  80

Arg Phe Ser Gly Ser Gly Ser Gly Gln Val Tyr Ser Leu Thr Ile Ser
                 85                  90                  95

Ser Leu Glu Tyr Glu Asp Met Gly Thr Tyr Tyr Cys Leu Gln Phe Asp
                100                 105                 110

Glu Phe Pro Trp Met Phe Gly Gly Gly Thr Lys Leu Glu Ile Lys Arg
            115                 120                 125

Ala Asp Ala Ala Pro Thr Val Ser Ile Phe Pro Pro Ser Ser
130                 135                 140
```

(2) INFORMATION FOR SEQ ID NO:3:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 22..462

(xi) SEQUENCE DESCRIPTION: SEQ ID NO:3:

```
AGTCATATGG ATTGGGAATT C ATG GAA TGG AGC TGG GTC ATT CTC TTC CTC      51
                       Met Glu Trp Ser Trp Val Ile Leu Phe Leu
                                   145                 150

CTG TCA GGA ACT GCA GGT GTC CAC TCT GAG GTC CAG CTG CAA CAG TCT      99
Leu Ser Gly Thr Ala Gly Val His Ser Glu Val Gln Leu Gln Gln Ser
            155                 160                 165

GGA CCT GAG CTG GTG AAG CCT GGA GCT TCA CTG AAG ATT TCC TGC GAG     147
Gly Pro Glu Leu Val Lys Pro Gly Ala Ser Leu Lys Ile Ser Cys Glu
170                 175                 180

GCT TCT GGT TAC TCA CTC ACT GCC TAC ACC ATG AAC TGG GTG AAG CAG     195
Ala Ser Gly Tyr Ser Leu Thr Ala Tyr Thr Met Asn Trp Val Lys Gln
185                 190                 195                 200

AGC CAT GGA AAG AGC CTT GAG TGG GTT GGG CTG ATT AAT CCT TTC AGT     243
Ser His Gly Lys Ser Leu Glu Trp Val Gly Leu Ile Asn Pro Phe Ser
                205                 210                 215

GGT GAT ACT AAC TAC AGC CAG AAA TTC ACG GGC AAG GCC ACA TTA ACT     291
Gly Asp Thr Asn Tyr Ser Gln Lys Phe Thr Gly Lys Ala Thr Leu Thr
            220                 225                 230

GTA GAC AGG TCA TCC AGC ACA GCC TAC ATG GAG CTC CTC AGT CTG ACA     339
Val Asp Arg Ser Ser Ser Thr Ala Tyr Met Glu Leu Leu Ser Leu Thr
            235                 240                 245

TCT GAG GAC TCT GCA GTC TAT TAC TGT GTC ATT ACT CCG GTT CCC TAC     387
Ser Glu Asp Ser Ala Val Tyr Tyr Cys Val Ile Thr Pro Val Pro Tyr
250                 255                 260

TGG TAC TTC GAT GTC TGG GGC GCA GGG ACC ACG GTC ACC GTC TCC TCA     435
Trp Tyr Phe Asp Val Trp Gly Ala Gly Thr Thr Val Thr Val Ser Ser
265                 270                 275                 280

GCC AAA ACG ACA CCC CCA TCC GTC TAT                                 462
Ala Lys Thr Thr Pro Pro Ser Val Tyr
                285
```

(2) INFORMATION FOR SEQ ID NO:4:

(i) SEQUENCE CHARACTERISTICS:

(A) LENGTH: 147 amino acids
       (B) TYPE: amino acid
       (D) TOPOLOGY: linear (ii) MOLECULE TYPE: protein (xi) SEQUENCE DESCRIPTION: SEQ ID NO:4:

Met Glu Trp Ser Trp Val Ile Leu Phe Leu Leu Ser Gly Thr Ala Gly
 1               5                  10                  15

Val His Ser Glu Val Gln Leu Gln Gln Ser Gly Pro Glu Leu Val Lys
                20                  25                  30

Pro Gly Ala Ser Leu Lys Ile Ser Cys Glu Ala Ser Gly Tyr Ser Leu
            35                  40                  45

Thr Ala Tyr Thr Met Asn Trp Val Lys Gln Ser His Gly Lys Ser Leu
50                  55                  60

Glu Trp Val Gly Leu Ile Asn Pro Phe Ser Gly Asp Thr Asn Tyr Ser
65                  70                  75                  80

Gln Lys Phe Thr Gly Lys Ala Thr Leu Thr Val Asp Arg Ser Ser Ser
                85                  90                  95

Thr Ala Tyr Met Glu Leu Leu Ser Leu Thr Ser Glu Asp Ser Ala Val
            100                 105                 110

Tyr Tyr Cys Val Ile Thr Pro Val Pro Tyr Trp Tyr Phe Asp Val Trp
        115                 120                 125

Gly Ala Gly Thr Thr Val Thr Val Ser Ser Ala Lys Thr Thr Pro Pro
130                 135                 140

Ser Val Tyr
145

(2) INFORMATION FOR SEQ ID NO:5:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (xi) SEQUENCE DESCRIPTION: SEQ ID NO:5:

TGTGTGTCTG TATATAACAT AACTGTTTAC ACATAATACA CTGAAATGGA GCCCTTCCTT        60

GTTACTTCAT ACCATCCTCT GTGCTTCCTT CCTCAGGGGC TGATGCTGCA CCAACTGTAT       120

CCATCTTCCC ACCATCCAGT GAGCAGTTAA CATCTGGAGG TGCCTCAGTC GTGTGCTTCT       180

TGAACAACTT CTACCCCAAA GACATCAATG TCAAGTGGAA GATTGATGGC AGTGAACGAC       240

AAAATGGCGT CCTGAACAGT TGGACTGATC AGGACAGCAA AGACAGCACC TACAGCATGA       300

GCAGCACCCT CACGTTGACC AAGGACGAGT ATGAACGACA TAACAGCTAT ACCTGTGAGG       360

CCACTCACAA GACATCAACT TCACCCATTG TCAAGAGCTT CAACAGGAAT GAGTGTTAGA       420

GACAAAGGTC CTGAGACGCC ACCACCAGCT CCCCAGCTCC ATCCTATCTT CC               472

(2) INFORMATION FOR SEQ ID NO:6:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(99..389, 746..784, 883..1203, 1325..1645)

(xi) SEQUENCE DESCRIPTION: SEQ ID NO:6:

```
TCGGGGACAT GGGAAGGGTG CAAAAGTAGC GGCCTTCTAG AAGGTTTGGA CCTGTCCTGT          60

CCTGTCCGAC AGTGTAATCA CATATACTTT TTCTTGTA GCC AAA ACG ACA CCC             113
                                           Ala Lys Thr Thr Pro
                                            1               5

CCA TCT GTC TAT CCA CTG GCC CCT GGA TCT GCT GCC CAA ACT AAC TCC          161
Pro Ser Val Tyr Pro Leu Ala Pro Gly Ser Ala Ala Gln Thr Asn Ser
             10                  15                  20

ATG GTG ACC CTG GGA TGC CTG GTC AAG GGC TAT TTC CCT GAG CCA GTG          209
Met Val Thr Leu Gly Cys Leu Val Lys Gly Tyr Phe Pro Glu Pro Val
                 25                  30                  35

ACA GTG ACC TGG AAC TCT GGA TCC CTG TCC AGC GGT GTG CAC ACC TTC          257
Thr Val Thr Trp Asn Ser Gly Ser Leu Ser Ser Gly Val His Thr Phe
             40                  45                  50

CCA GCT GTC CTG CAG TCT GAC CTC TAC ACT CTG AGC AGC TCA GTG ACT          305
Pro Ala Val Leu Gln Ser Asp Leu Tyr Thr Leu Ser Ser Ser Val Thr
         55                  60                  65

GTC CCC TCC AGC CCT CGG CCC AGC GAG ACC GTC ACC TGC AAC GTT GCC          353
Val Pro Ser Ser Pro Arg Pro Ser Glu Thr Val Thr Cys Asn Val Ala
 70                  75                  80                  85

CAC CCG GCC AGC AGC ACC AAG GTG GAC AAG AAA ATT GGTGAGAGGA               399
His Pro Ala Ser Ser Thr Lys Val Asp Lys Lys Ile
                 90                  95

CATATAGGGA GGAGGGGTTC ACTAGAAGTG AGGCTCAAGC CATTAGCCTG CCTAAACCAA         459

CCAGGCTGGA CAGCCAACCA ACCAGGAAAT GGATCTCAGC CCAGAAGATC AAAAGTTGTT         519

CTTCTCCCTT CTGGAGATTT CTATGTCCTT TACAACTCAA TTGGTTAATA TCCTGGGTTG         579

GAGTCCCACA CATCTTGACA AACAGAGACA AATTTGAGTA TCACCAGCCA AAAGTCATAC         639

CCAAAAACAG CCTGGCATGA CCACACACCA GACTCAAACT TACCCTACCT TTATCCTGGT         699

GGCTTCTCAT CTCCAGACCC CAGTAACACA TAGCTTTCTC TCCACA GTG CCC AGG           754
                                                   Val Pro Arg
                                                               100

GAT TGT GGT TGT AAG CCT TGC ATA TGT ACA GGTAAGTCAG TGGCCTTCAC            804
Asp Cys Gly Cys Lys Pro Cys Ile Cys Thr
                105                 110

CTGACCCAGA TGCAACAAGT GGCAATGTTG GAGGGTGGCC AGGTATTGAC CTATTTCCAC         864

CTTTCTTCTT CATCCTTA GTC CCA GAA GTA TCA TCT GTC TTC ATC TTC CCC          915
                    Val Pro Glu Val Ser Ser Val Phe Ile Phe Pro
                                115                 120

CCA AAG CCC AAG GAT GTG CTC ACC ATT ACT CTG ACT CCT AAG GTC ACG          963
Pro Lys Pro Lys Asp Val Leu Thr Ile Thr Leu Thr Pro Lys Val Thr
             125                 130                 135

TGT GTT GTG GTA GAC ATC AGC AAG GAT GAT CCC GAG GTC CAG TTC AGC         1011
Cys Val Val Val Asp Ile Ser Lys Asp Asp Pro Glu Val Gln Phe Ser
             140                 145                 150

TGG TTT GTA GAT GAT GTG GAG GTG CAC ACA GCT CAG ACG CAA CCC CGG         1059
Trp Phe Val Asp Asp Val Glu Val His Thr Ala Gln Thr Gln Pro Arg
155                 160                 165

GAG GAG CAG TTC AAC AGC ACT TTC CGC TCA GTC AGT GAA CTT CCC ATC         1107
Glu Glu Gln Phe Asn Ser Thr Phe Arg Ser Val Ser Glu Leu Pro Ile
170                 175                 180                 185

ATG CAC CAG GAC TGG CTC AAT GGC AAG GAG TTC AAA TGC AGG GTC AAC         1155
Met His Gln Asp Trp Leu Asn Gly Lys Glu Phe Lys Cys Arg Val Asn
                 190                 195                 200

AGT GCA GCT TTC CCT GCC CCC ATC GAG AAA ACC ATC TCC AAA ACC AAA         1203
Ser Ala Ala Phe Pro Ala Pro Ile Glu Lys Thr Ile Ser Lys Thr Lys
             205                 210                 215

GGTGAGAGCT GCAGTGTGTG ACATAGAAGC TGCAATAGTC AGTCCATAGA CAGAGCTTGG        1263
```

```
CATAACAGAC CCCTGCCCTG TTCGTGACCT CTGTGCTGAC CAATCTCTTT ACCCACCCAC    1323

A GGC AGA CCG AAG GCT CCA CAG GTG TAC ACC ATT CCA CCT CCC AAG        1369
  Gly Arg Pro Lys Ala Pro Gln Val Tyr Thr Ile Pro Pro Pro Lys
      220                 225                 230

GAG CAG ATG GCC AAG GAT AAA GTC AGT CTG ACC TGC ATG ATA ACA GAC      1417
Glu Gln Met Ala Lys Asp Lys Val Ser Leu Thr Cys Met Ile Thr Asp
            235                 240                 245

TTC TTC CCT GAA GAC ATT ACT GTG GAG TGG CAG TGG AAT GGG CAG CCA      1465
Phe Phe Pro Glu Asp Ile Thr Val Glu Trp Gln Trp Asn Gly Gln Pro
        250                 255                 260

GCG GAG AAC TAC AAG AAC ACT CAG CCC ATC ATG AAC ACG AAT GGC TCT      1513
Ala Glu Asn Tyr Lys Asn Thr Gln Pro Ile Met Asn Thr Asn Gly Ser
265                 270                 275                 280

TAC TTC GTC TAC AGC AAG CTC AAT GTG CAG AAG AGC AAC TGG GAG GCA      1561
Tyr Phe Val Tyr Ser Lys Leu Asn Val Gln Lys Ser Asn Trp Glu Ala
                285                 290                 295

GGA AAT ACT TTC ACC TGC TCT GTG TTA CAT GAG GGC CTG CAC AAC CAC      1609
Gly Asn Thr Phe Thr Cys Ser Val Leu His Glu Gly Leu His Asn His
            300                 305                 310

CAT ACT GAG AAG AGC CTC TCC CAC TCT CCT GGT AAA TGATCCCAGT           1655
His Thr Glu Lys Ser Leu Ser His Ser Pro Gly Lys
        315                 320

GTCCTTGGAG CCCTCTGGTC CTACAGGACT CTGACACCTA CCTCCACCCC TCCCTGTATA    1715

AATAAAGCAC CCAGCACTGC CTTGGGACCC TGCAATAACG TCCTGGTGAT TTCTGAGATG    1775

TAGAGTCTAG CTAGGTCATG GAATG                                          1800

(2) INFORMATION FOR SEQ ID NO:7:

(i) SEQUENCE CHARACTERISTICS:
        (A) LENGTH: 324 amino acids
        (B) TYPE: amino acid
        (D) TOPOLOGY: linear (ii) MOLECULE TYPE: protein (xi) SEQUENCE DESCRIPTION: SEQ ID NO:7:

Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175
```

```
Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
            210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                    245                 250                 255

Glu Trp Gln Trp Asn Gly Gln Pro Ala Glu Asn Tyr Lys Asn Thr Gln
                260                 265                 270

Pro Ile Met Asn Thr Asn Gly Ser Tyr Phe Val Tyr Ser Lys Leu Asn
                275                 280                 285

Val Gln Lys Ser Asn Trp Glu Ala Gly Asn Thr Phe Thr Cys Ser Val
                290                 295                 300

Leu His Glu Gly Leu His Asn His His Thr Glu Lys Ser Leu Ser His
305                 310                 315                 320

Ser Pro Gly Lys (2) INFORMATION FOR SEQ ID NO:8:

(i) SEQUENCE CHARACTERISTICS:
        (A) LENGTH: 320 amino acids
        (B) TYPE: amino acid
        (C) STRANDEDNESS: single
        (D) TOPOLOGY: linear (xi) SEQUENCE DESCRIPTION: SEQ ID NO:8:

Ala Lys Thr Thr Pro Pro Thr Val Tyr Pro Leu Ala Pro Gly Ser Asn
1                   5                   10                  15

Ala Ala Ser Gln Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Lys Leu Tyr Thr Leu
50                  55                  60

Ser Ser Ser Val Ser Val Pro Thr Ser Pro Glu Thr Val Thr Cys Asn
65                  70                  75                  80

Val Ala His Ala Pro Ser Ser Thr Lys Val Asp Lys Lys Ile Val Pro
                85                  90                  95

Arg Asp Cys Gly Cys Lys Pro Cys Ile Cys Thr Val Pro Glu Val Ser
            100                 105                 110

Ser Val Phe Ile Phe Pro Pro Lys Pro Lys Asp Thr Leu Leu Ile Thr
            115                 120                 125

Val Thr Pro Lys Val Thr Cys Val Val Val Asp Ile Ser Lys Asp Asp
130                 135                 140

Pro Glu Val Gln Phe Ser Trp Phe Val Asp Asn Val Glu Val His Thr
145                 150                 155                 160

Ala Gln Thr Gln Pro Arg Glu Glu Gln Phe Asn Ser Thr Phe Arg Val
                165                 170                 175

Val Ser Ala Leu Pro Ile Met His Gln Asp Trp Leu Asn Gly Lys Glu
            180                 185                 190

Phe Lys Cys Arg Val Asn Ser Ala Ala Phe Pro Ala Pro Ile Glu Lys
            195                 200                 205
```

```
Thr Ile Ser Lys Thr Lys Gly Lys Pro Arg Ala Pro Gln Val Tyr Thr
    210                 215                 220
Ile Pro Pro Pro Lys Glu Gln Met Ala Lys Asp Lys Val Ser Leu Thr
225                 230                 235                 240
Cys Met Ile Thr Asp Phe Phe Pro Glu Asp Ile Thr Val Glu Trp Gln
                245                 250                 255
Ser Asp Gly Gln Ala Pro Glu Asn Tyr Lys Asn Thr Gln Pro Ile Met
                260                 265                 270
Asp Thr Asp Gly Ser Tyr Phe Val Tyr Ser Lys Leu Asn Val Gln Lys
            275                 280                 285
Ser Asn Trp Glu Ala Gly Asn Thr Phe Thr Cys Ser Val Leu His Glu
290                 295                 300
Gly Leu His Asn His His Thr Glu Lys Ser Leu Ser Met Ser Pro Gly
305                 310                 315                 320
```

(2) INFORMATION FOR SEQ ID NO:9:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (xi) SEQUENCE DESCRIPTION: SEQ ID NO:9:

GGGAATTCAT GRAATGSASC TGGGTYWTYC TCTT    34

(2) INFORMATION FOR SEQ ID NO:10:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ix) FEATURE:
    (A) NAME/KEY: misc_feature
    (B) LOCATION: 6
    (D) OTHER INFORMATION: /note= "N represents Inosine"

(xi) SEQUENCE DESCRIPTION: SEQ ID NO:10:

GGTRGNCARA TAGGKRACCR GGGACCTTCG AACCC    35

(2) INFORMATION FOR SEQ ID NO:11:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (xi) SEQUENCE DESCRIPTION: SEQ ID NO:11:

TAATACGACT CACTATAGGG    20

(2) INFORMATION FOR SEQ ID NO:12:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (xi) SEQUENCE DESCRIPTION: SEQ ID NO:12:

CTTTTCCCAG TCACGACGT    19

(2) INFORMATION FOR SEQ ID NO:13:

```
     (i) SEQUENCE CHARACTERISTICS:
          (A) LENGTH: 35 base pairs
          (B) TYPE: nucleic acid
          (C) STRANDEDNESS: single
          (D) TOPOLOGY: linear (xi) SEQUENCE DESCRIPTION: SEQ ID NO:13:

ACTAGTCGAC ATGGTRTCCW CASCTCAGTT CCTTG                              35

(2) INFORMATION FOR SEQ ID NO:14:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (xi) SEQUENCE DESCRIPTION: SEQ ID NO:14:

CCCAAGCTTA CTGGATGGTG GGAAGATGGA                                    30

(2) INFORMATION FOR SEQ ID NO:15:

(i) SEQUENCE CHARACTERISTICS:
          (A) LENGTH: 15 amino acids
          (B) TYPE: amino acid
          (C) STRANDEDNESS: single
          (D) TOPOLOGY: linear (xi) SEQUENCE DESCRIPTION: SEQ ID NO:15:

Xaa Val Gln Leu Gln Gln Ser Gly Pro Glu Leu Val Lys Pro Gly
1               5                   10                  15
```